United States Patent
Kimonis et al.

(10) Patent No.: US 10,093,932 B2
(45) Date of Patent: Oct. 9, 2018

(54) EXON SKIPPING TECHNOLOGY IN VCP DISEASE

(71) Applicant: The Regents of the University of California, Oakland, CA (US)

(72) Inventors: Virginia Kimonis, Irvine, CA (US); Angele Nalbandian, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/382,539

(22) Filed: Dec. 16, 2016

(65) Prior Publication Data

US 2017/0175126 A1  Jun. 22, 2017

Related U.S. Application Data

(60) Provisional application No. 62/268,271, filed on Dec. 16, 2015.

(51) Int. Cl.
- *A61K 48/00* (2006.01)
- *C12N 15/113* (2010.01)
- *A01K 67/027* (2006.01)

(52) U.S. Cl.
CPC ...... *C12N 15/1137* (2013.01); *A01K 67/0278* (2013.01); *A01K 2217/072* (2013.01); *A01K 2217/203* (2013.01); *A01K 2227/105* (2013.01); *A01K 2267/0318* (2013.01); *C12N 2310/11* (2013.01); *C12N 2310/14* (2013.01); *C12N 2310/141* (2013.01); *C12N 2310/313* (2013.01); *C12N 2310/315* (2013.01); *C12N 2310/3181* (2013.01); *C12N 2310/321* (2013.01); *C12N 2310/3231* (2013.01); *C12N 2310/3233* (2013.01); *C12N 2320/33* (2013.01)

(58) Field of Classification Search
CPC ................................................. A61K 48/00
See application file for complete search history.

(56) References Cited

PUBLICATIONS

Aoki, Y. et al. (Aug. 21, 2012, e-published Aug. 6, 2012). "Bodywide skipping of exons 45-55 in dystrophic mdx52 mice by systemic antisense delivery," *PNAS USA* 109(34):13763-13768.

Badadani, M. et al. (Oct. 5, 2010). "VCP associated inclusion body myopathy and paget disease of bone knock-in mouse model exhibits tissue pathology typical of human disease," *PLoS One* 5(10):e13183.

Goyenvalle, A. et al. (Jan. 2010, e-published Oct. 20, 2009). "Prevention of dystrophic pathology in severely affected dystrophin/utrophin-deficient mice by morpholino-oligomer-mediated exon-skipping," *Mol Ther* 18(1):198-205.

Kimonis, V.E. et al. (Jul.-Aug. 2000). "Clinical and molecular studies in a unique family with autosomal dominant limb-girdle muscular dystrophy and Paget disease of bone," *Genet Med* 2(4):232-241.

Kimonis, V.E. et al. (Mar. 15, 2008). "Clinical studies in familial VCP myopathy associated with Paget disease of bone and frontotemporal dementia," *Am J Med Genet A* 146A(6):745-757.

Kovach, M.J. et al. (Dec. 2001). "Clinical delineation and localization to chromosome 9p13.3-p12 of a unique dominant disorder in four families: hereditary inclusion body myopathy, Paget disease of bone, and frontotemporal dementia," *Mol Genet Metab* 74(4):458-475.

Nalbandian, A. et al. (Feb. 2013, e-published Nov. 21, 2012). "A progressive translational mouse model of human valosin-containing protein disease: the VCP(R155H/+) mouse," *Muscle Nerve* 47(2):260-270.

Shi, S. et al. (Jul. 4, 2013). "Antisense-oligonucleotide mediated exon skipping in activin-receptor-like kinase 2: inhibiting the receptor that is overactive in fibrodysplasia ossificans progressiva," *PLoS One* 8(7):e69096.

Watts, G.D. et al. (Sep. 2003). "Clinical and genetic heterogeneity in chromosome 9p associated hereditary inclusion body myopathy: exclusion of GNE and three other candidate genes," *Neuromuscul Disord* 13(7-8):559-567.

Watts, G.D. et al. (Apr. 2004, e-published Mar. 21, 2004). "Inclusion body myopathy associated with Paget disease of bone and frontotemporal dementia is caused by mutant valosin-containing protein," *Nat Genet* 36(4):377-381.

Yang, L. et al. (Apr. 26, 2013). "Effective exon skipping and dystrophin restoration by 2'-o-methoxyethyl antisense oligonucleotide in dystrophin-deficient mice," *PLoS One* 8(4):e61584.

Yokota, T. et al. (Oct. 2012, e-published Aug. 13, 2012). "Extensive and prolonged restoration of dystrophin expression with vivo-morpholino-mediated multiple exon skipping in dystrophic dogs," *Nucleic Acid Ther* 22(5):306-315.

*Primary Examiner* — Kimberly Chong

(74) *Attorney, Agent, or Firm* — Mintz Levin Cohn Ferris Glovsky and Popeo, P.C.

(57) ABSTRACT

Provided herein are methods, compositions and transgenic mice useful in treating and developing treatments for VCP-associated neurodegenerative diseases.

17 Claims, 15 Drawing Sheets

Specification includes a Sequence Listing.

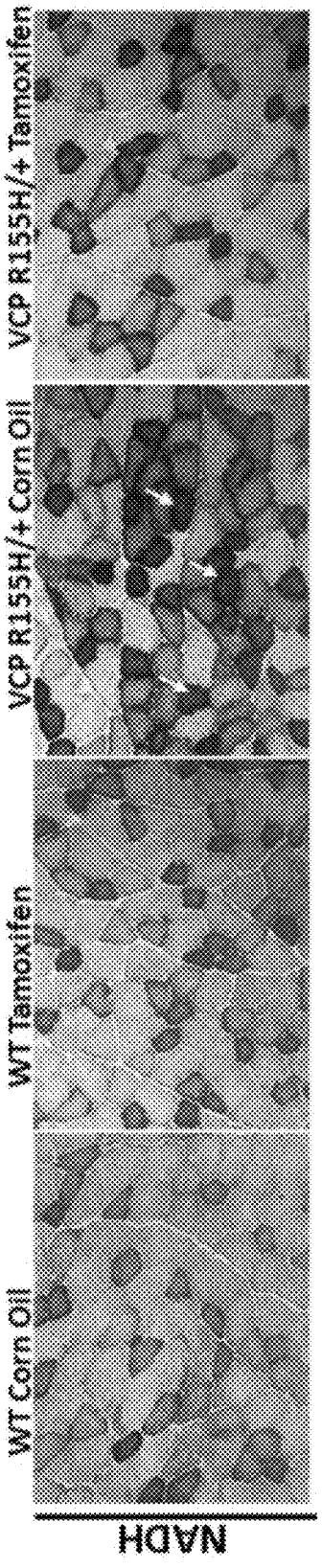
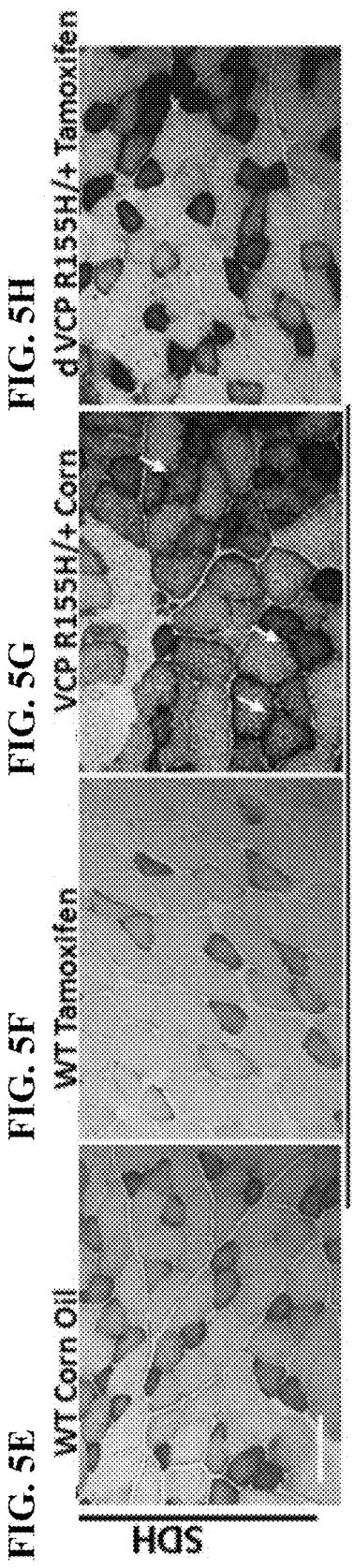
FIG. 5A  FIG. 5B  FIG. 5C  FIG. 5D
WT Corn Oil  WT Tamoxifen  VCP R155H/+ Corn Oil  VCP R155H/+ Tamoxifen
NADH
FIG. 5E  FIG. 5F  FIG. 5G  FIG. 5H
WT Corn Oil  WT Tamoxifen  VCP R155H/+ Corn Oil  VCP R155H/+ Tamoxifen
SDH FIG. 6E
FIG. 6F
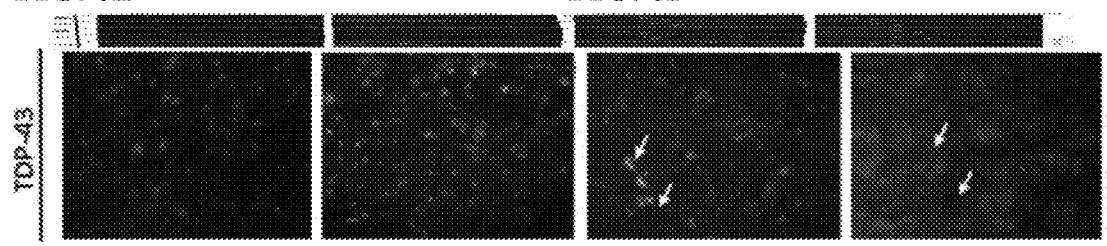
FIG. 6G
FIG. 6H
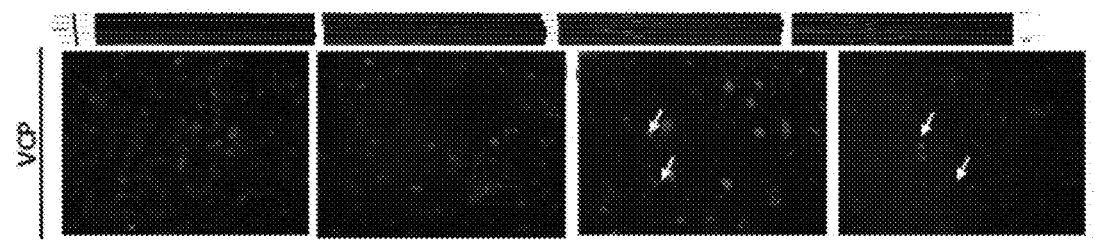
FIG. 6I
FIG. 6J
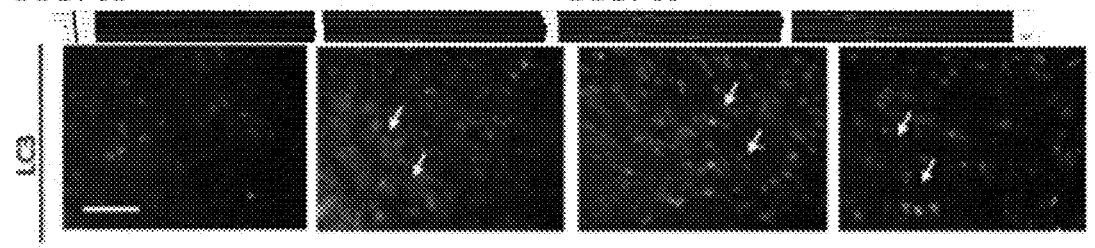

EXON SKIPPING TECHNOLOGY IN VCP DISEASE

CROSS-REFERENCES TO RELATED APPLICATIONS

This application claims priority to U.S. Provisional Patent Application No. 62/268,271, filed Dec. 16, 2015, the disclosure of which is incorporated by reference herein in their entirety and for all purposes.

REFERENCE TO A SEQUENCE LISTING, A TABLE OR A COMPUTER PROGRAM LISTING APPENDIX SUBMITTED AS AN ASCII TEXT FILE

The Sequence Listing written in file 48538-525001US_ST25.TXT, created on Dec. 28, 2016, 58,669 bytes, machine format IBM-PC, MS Windows operating system, is hereby incorporated by reference.

BACKGROUND OF THE INVENTION

Inclusion Body Myopathy (IBM) associated with Paget's disease of the bone (PDB) and Frontotemporal Dementia, (IBMPFD, OMIM 167320), was first reported in 2000 by Kimonis et al. [1], and mapped to the human chromosomal region 9p13.3-12[2],[3]. In 2004, the disease was attributed to mutations in the gene encoding Valosin-Containing Protein (VCP) [4]. Classic symptoms of VCP disease include weakness and atrophy of the pelvic and shoulder girdle muscles in 90% of individuals [1-3]. Affected individuals exhibit scapular winging and die from progressive muscle weakness and cardiac and respiratory failure typically in their 40s to 50s [1, 5]. Histologically, patients show the presence of rimmed vacuoles and TAR DNA-binding protein 43 (TDP-43)-positive ubiquitinated inclusion bodies in the muscles [1, 4, 5, 6]. The variable phenotype is often diagnosed as limb girdle muscular dystrophy (LGMD), amyotrophic lateral sclerosis (ALS), facioscapular muscular dystrophy (FSHD), or scapuloperoneal muscular dystrophy (SPMD) [5, 7, 8]. To date, 31 VCP mutations have been reported in families from several parts of the world including Germany [9, 10], France [11], Austria [12], Italy [13, 14], the UK [15], Australia [16], Brazil [17], Korea [18], Japan [19] and the US [20, 21]. VCP mutations have been noted in 2-3% of isolated familial amyotrophic lateral sclerosis (fALS) cases [22], and 10-15% of individuals with hereditary inclusion body myopathy have an ALS-like phenotype characterized as a progressive neurodegenerative disease involving both upper motor neurons (UMNs) and lower motor neurons (LMNs) [5]. In order to understand the cellular and molecular pathophysiological mechanism(s) underlying VCP-associated neurodegenerative diseases, Applicants generated a unique CRE-ER™-VCP$^{R155H/+}$ TAMOXIFEN™-inducible mouse model. This technology allows determination of the effects of targeted excision of exons 4 and 5, including the R155H mutation, in VCP disease. Applicants administered pregnant dams with 0.12 mg/g body weight TAMOXIFEN™ or corn oil by oral gavage and monitored their survival and muscle strength of the pups until 18 months of age. The TAMOXIFEN™-treated CRE-ER™-VCP$^{R155H/+}$ mice demonstrated improved muscle strength and quadriceps muscles fiber architecture, reduced expression of autophagy markers, reduced brain neuropathology, decreased apoptosis, and partially rescued Paget's disease of bone. Parallel studies using splice switching therapeutics, which exclude or promote retention of specific exons as necessary, have been used successfully in muscle degenerative diseases such as Duchenne muscular dystrophy (DMD-exon skipping) and spinal muscular atrophy (SMA-exon retention).

Recently, VCP has also shown to play a critical role in maintaining mitochondrial quality and dynamics in the PINK1/Parkin pathway, whereby pathogenic mutations in VCP lead to an impairment in proteasome-dependent degradation [23]. Other studies have demonstrated the autophagic mechanism of VCP regulation and function, an important process in mediating protein degradation for terminally differentiated cells. Autophagy is responsible for degrading defective organelles and the bulk of cytoplasm during starvation. Recent studies have shown that sequestosome 1 (p62/SQSTM1) interacts with the autophagic effector protein Light Chain 3 (LC3B-I/II) to mediate the autophagic uptake of aggregated proteins. VCP is important for the retro-translocation of misfolded endoplasmic reticulum (ER) proteins, and failure in this activity results in defective endoplasmic reticulum associated protein degradation (ERAD) and ER stress responses [24]. Interestingly, the SQSTM1 gene, which encodes p62/SQSTM1, is involved in autophagy, and apoptosis, and is responsible for approximately 10% of sporadic PDB and 50% of familial PDB and mutations in p62/SQSTM1 have now been associated with ALS. Autophagic degradation is also involved in Alzheimer's and Huntington's diseases, among other neurodegenerative diseases [25-29].

Generation of TAMOXIFEN™-inducible Cre models has become the gold standard for determining gene function in mice by allowing the phenotypic analyses for selected tissues during embryonic development, thus, providing a powerful platform to analyze the functions of genes and proteins physiologically in vivo. Recent studies based on novel gene, cell and drug therapies in patients have shown promising exon skipping strategies to treat muscular dystrophies such as Duchenne muscular dystrophy (DMD), Becker muscular dystrophy (BMD) [30, 31], and in another autosomal dominant disorder fibrodysplasia ossificans progressive (FOP) by reducing the excessive activin receptor-like kinase 2 (ACVR1/ALK2) in FOP patients [32].

There is disclosed herein a transgenic CRE-ER™-VCP$^{R155H/+}$ mouse model, with the targeted excision of the VCP R155H mutation that demonstrates amelioration of the typical phenotypic features observed in VCP-associated diseased patients.

BRIEF SUMMARY OF THE INVENTION

In a first aspect, there is provided a method of treating a VCP-associated neurodegenerative disease in a subject in need thereof. The method includes administering to the subject a therapeutically effective amount of an antisense VCP exon 4 nucleic acid or an antisense VCP exon 5 nucleic acid.

In another aspect, there is provided a transgenic mouse including a TAMOXIFEN™-inducible Cre recombinase excisable VCP exon 4 or a TAMOXIFEN™-inducible Cre recombinase excisable VCP exon 5.

BRIEF DESCRIPTION OF THE DRAWINGS

FIG. 1A: Schematic of exons 1-5 in the VCP gene with the R155H mutation flanked by loxp sites. FIG. 1B: PCR analysis with primers flanking the loxp sites, reveal 500 base pair product after Cre-loxp recombination in the CRE-ER™-VCP$^{R155H/+}$ 3 week-old pups from TAMOXIFEN™-treated Cre-ER™-VCP$_{R155H/+}$ pregnant mice. Lanes: M: molecular weight markers; 1: Wild type corn oil (CO)-treated (liver); 2: Wild type TAMOXIFEN™-treated (liver); 3: CRE-ER™-VCP$^{R155H/+}$ corn oiltreated (liver); 4: CRE-ER™-VCP$^{R155H/+}$ TAMOXIFEN™-treated (liver); 5: CRE-ER™-VCP$^{R155H/+}$ corn oil-treated (quadriceps); 6: CRE-ER™-VCP$^{R155H/+}$ TAMOXIFEN™-treated (quadriceps); 7: CRE-ER™-VCP$^{R155H/+}$ corn oil-treated (brain); 8: CRE-ER™-VCP$^{R155H/+}$ TAMOXIFEN™-treated (brain); 9: CRE-ER™-VCP$^{R155H/+}$ corn oil-treated (kidney); 10: CRE-ER™-VCP$^{R155H/+}$ TAMOXIFEN™-treated (kidney). The number of animals used was n=10/group.

FIG. 2A and FIG. 2B: Weight analysis (FIG. 2A) and grip strength (FIG. 2B) measurements of WT and Cre-ER™-VCP$^{R155H/+}$ TAMOXIFEN™-treated animals at 3, 9, 15, 18 months of age. FIG. 2C: Histological analysis by H&E in corn oil control or TM-treated WT and corn oil control and TM-treated Cre-ER™-VCP$^{R155H/+}$ mice. Black arrows indicate centralized nuclei (left) and degenerating fibers (right). Statistical significance is denoted by *p<0.05 and **p<0.005 with a Student's one-tailed t-test. The number of animals used was n=8-10/group.

FIG. 3A: Immunohistochemical analysis of ubiquitin, LC3I/II, p62/SQSTM1, VCP and TDP-43-specific autophagy markers in quadriceps from 18-month old WT and CRE-ER™-VCP$^{R155H/+}$ corn oil- and TAMOXIFEN™-treated animals, respectively. FIG. 3B: Western blot analysis of autophagy intermediates in 18-month old WT and CRE-ER™-VCP$^{R155H/+}$ mice TAMOXIFEN™-treated animals. Beta actin was used as loading controls. FIG. 3C: Densitometric analysis of Western blots. Statistical significance is denoted by *p<0.05 and **p<0.005 with a Student's one-tailed t-test. The number of animals used was n=8-10/group.

FIG. 4A: TUNEL staining of quadriceps muscles from corn oil (CO)-treated WT and CRE-ER™-VCP$^{R155H/+}$ mice, and TAMOXIFEN™ (TM)-treated WT and CRE-ER™-VCP$^{R155H/+}$ mice at 18-months of age (Magnification: 630×). FIG. 4B: Quantification of TUNEL+ cells in corn oil (vehicle)- and TAMOXIFEN™-treated CRE-ER™-VCP$^{R155H/+}$ mice. FIG. 4C: Western blot analysis of apoptosis markers, Bcl-2, BAX and PUMA in 18-month old WT and CRE-ER™-VCP$^{R155H/+}$ mice TAMOXIFEN™-treated animals. Beta actin was used as loading control. FIG. 4D: Densitometry analysis of the apoptosis marker western blot shown above. Statistical significance is denoted by *p<0.05 and **p<0.005 with a Student's one-tailed t-test. The number of animals used was n=8-10/group.

FIGS. 5A-5I. Mitochondrial enzyme analysis of CRE-ER™-VCP$^{R155H/+}$ mice. Staining with (FIGS. 5A-5D) NADH and (FIGS. 5E-5H) SDH in WT and CRE-ER™-VCP$^{R155H/+}$ corn oil control (vehicle) and TAMOXIFEN™-treated animals, respectively. FIG. 5I: Quantification of SDH and NADH oxidative fibers in WT and CRE-ER™-VCP$^{R155H/+}$ mice corn oil control (vehicle) and TAMOXIFEN™-treated animals. Statistical significance is denoted by *p<0.05 and **p<0.005 with a Student's one-tailed t-test. The number of animals used was n=8-10/group.

FIGS. 6A-6L. Neuropathological brain analysis of autophagy cascade in CRE-ER™-VCP$^{R155H/+}$ mice. Immunohistochemical analysis of (FIGS. 6A-6B) GFAP, (FIGS. 6C-6D) HT7, (FIGS. 6E-6F) TDP-43, (FIGS. 6G-6H) VCP and (FIGS. 6I-6J) LC3 protein expression levels in brains from 18-month old WT and CRE-ER™-VCP$^{R155H/+}$ corn oil and TAMOXIFEN™-treated animals (Magnification: 400×). FIG. 6K: Western blot analysis of autophagy cascade intermediates in 18-month old WT and CRE-ER™-VCP$^{R155H/+}$ brains from TAMOXIFEN™-treated animals. FIG. 6L: Densitometry analysis performed on the Western blot. Statistical significance is denoted by *p<0.05 and **p<0.005 with a Student's one-tailed t-test. Alpha tubulin was used as a loading control. The number of animals used was n=8-10/group.

FIG. 8A: VCP allele depicting oligomer binding sites resulting in the skipping of exon 5. FIG. 8B: PCR sequence analysis of RNA from patient fibroblasts demonstrating exon skipping (529 bp) and/or no exon skipping (660 bp).

FIG. 9A: Schematic of exons 1-5 in the VCP gene with the R155H mutation flanked by loxp sites. FIG. 9B: Immunohistochemical analysis with Cre antibody depicting nuclear translocation following TAMOXIFEN™ administration. FIG. 9C: PCR analysis with primers flanking the loxp sites, reveal 500 base pair product after Cre-loxp recombination in the CRE-ER™-VCP$^{R155H/+}$ TAMOXIFEN™-treated mice. Lanes: M: molecular weight markers; 1: Wild type corn oil (CO)-treated (liver); 2: Wild type TAMOXIFEN™-treated (liver); 3-4: CRE-ER™-VCP$^{R155H/+}$ liver; 5-6: CRE-ER™-VCP$^{R155H/+}$ quadriceps; 7-8: CRE-ER™-VCP$^{R155H/+}$ brain; 9-10: CRE-ER™-VCP$^{R155H/+}$ kidney corn oil and TAMOXIFEN™-treated, respectively.

DETAILED DESCRIPTION OF THE INVENTION

I. Definitions

Figure 1A:
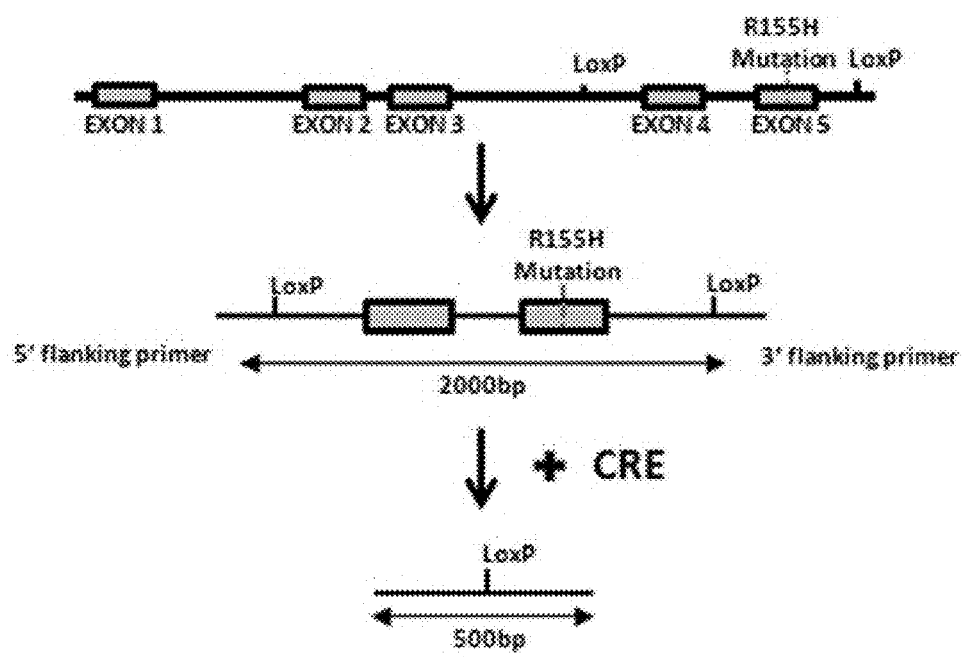
FIGS. 1A-1B. Cre-mediated recombination and functionality in CRE-ER™-VCP$^{R155H/+}$ mice.

The abbreviations used herein have their conventional meaning within the chemical and biological arts. The chemical structures and formulae set forth herein are constructed according to the standard rules of chemical valency known in the chemical arts.

"Nucleic acid" refers to deoxyribonucleotides or ribonucleotides and polymers thereof in either single- or double-stranded form, or complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, and 2-O-methyl ribonucleotides.

As used herein, a "phosphorothioate polymer backbone" is a chemical polymer with at least two phosphorothioate linkages (e.g. monothiophosphate) (e.g. linking together sugar subunits, cyclic subunits or alkyl subunits). The phosphorothioate polymer backbone may be a phosphorothioate sugar polymer, which is a phosphorothioate nucleic acid in which one or more (or all) of the chain of pentose sugars lack the bases (nucleobases) normally present in a nucleic acid. The phosphorothioate polymer backbone can include two or more phosphorothioate linkages. In embodiments, the modified nucleic acids include a phosphorothioate backbone.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length. The present invention includes polypeptides that are substantially identical to any of SEQ ID NOs: 1-6.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci.* USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross-reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

An "acceptor splice site" as used herein is a nucleic acid sequence that forms part of the 3' end of an intron sequence. The acceptor splice site may contain an AG nucleic acid sequence. A "donor splice site" as used is a nucleic acid sequence that forms part of the 5' end of an intron sequence. The donor splice site may contain a GU nucleic acid sequence. The acceptor splice site and the donor splice site serve as attachment points for the spliceosome (an RNA-protein complex), which interacts with the intron sequence and catalyzes its excision from the pre-mRNA sequence, thereby forming a mature-mRNA. In embodiments, the acceptor splice site forms part of SEQ ID NO:7. In embodiments, the donor splice site forms part of SEQ ID NO:7.

The term "intron" as provided herein is used according to its common meaning in the art and refers to both the nucleic acid sequence within a gene and the corresponding sequence in the unprocessed RNA transcript (pre-mRNA).

The term "exon" as provided herein is used according to its common meaning in the art and refers the nucleic acid sequence within a gene and the corresponding sequence in the unprocessed RNA transcript (pre-mRNA) or processed mature mRNA that encode for a protein.

The term "pre-mRNA" as provided herein refers to an unspliced mRNA nucleic acid sequence, which includes exon and intron sequences. During the process of splicing, the intron sequences are excised from the pre-mRNA sequence thereby forming a mature mRNA sequence which is subsequently translated into the protein encoded by the mature mRNA.

A "splice enhancer sequence", as provided herein, refers to an exon nucleic acid sequence (a nucleic acid sequence forming part of an exon), which directs and enhances binding of the spliceosome with the donor splice site and/or the acceptor splice site. In embodiments, the splice enhancer sequence forms part of SEQ ID NO:7.

The term "exon skipping" refers to the excision of faulty or misaligned sequences (e.g., exon sequences encoding a mutation) from a pre-mRNA through RNA splicing. The exon skipping technology relies on the binding of an antisense nucleic acid to a pre-mRNA exon and/or intron sequence, thereby causing it to be excised from the pre-mRNA through splicing. The excised sequences are not expressed and therefore exon skipping may be used to remove genetic mutations from a protein encoding mRNA resulting in the formation of a truncated but still functional protein despite the genetic mutation. The antisense nucleic acid provided herein including embodiments thereof may affect exon skipping of VCP exon 4 or VCP exon 5. Where the antisense nucleic acid provided herein affects exon skipping of VCP exon 4 or VCP exon 5, the antisense nucleic acid causes the removal of VCP exon 4 or VCP exon 5 from the pre-mRNA. Thus, the mature VCP RNA formed in the presence of the antisense nucleic acid provided herein including embodiments thereof may lack VCP exon 4 or VCP exon 5.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

The term "antisense nucleic acid" and the like, as used herein, refer to a nucleic acid molecule that has a nucleotide sequence complementary to the "sense strand" of DNA and that is transcribed into RNA (the "sense transcript") that may be translated into the protein product of a gene. The term "sense DNA" as used herein refers to a DNA molecule that has a nucleotide sequence complementary to the "antisense strand" of DNA. The term "antisense transcript" is used to mean an RNA transcript that is transcribed from a sense strand DNA. An antisense transcript is capable of hybridizing under stringent conditions with a sense strand DNA. In some embodiments, a sense transcript includes a portion of a specific gene transcript (e.g., 5' non-coding region, 3'non-translated sequence, intron, or exon) wherein the gene transcript is transcribed from the antisense strand of DNA, and wherein the exons of such gene transcript may be translated into a protein product of a gene. In some further embodiments, the antisense transcript does not include the complementary transcript to the sense transcript and may not be translated into a protein product of the gene; and the sense transcript and antisense transcript are each transcribed in opposite directions moving away from the same promoter region of DNA. In some embodiments, an antisense transcript may be complementary with any part of a specific gene transcript (sense transcript), i.e., at the 5' non-coding sequence, 3' non-translated sequence, introns, or the coding sequence.

A "siRNA," "small interfering RNA," "small RNA," or "RNAi" as provided herein refers to a nucleic acid that forms a double stranded RNA, which double stranded RNA has the ability to reduce or inhibit expression of a gene or target gene when expressed in the same cell as the gene or target gene. The complementary portions of the nucleic acid that hybridize to form the double stranded molecule typically have substantial or complete identity. In one embodiment, a siRNA or RNAi refers to a nucleic acid that has substantial or complete identity to a target gene and forms a double stranded siRNA. In embodiments, the siRNA inhibits gene expression by interacting with a complementary cellular mRNA thereby interfering with the expression of the complementary mRNA. Typically, the nucleic acid is at least about 15-50 nucleotides in length (e.g., each complementary sequence of the double stranded siRNA is 15-50 nucleotides in length, and the double stranded siRNA is about 15-50 base pairs in length). In other embodiments, the length is 20-30 base nucleotides, preferably about 20-25 or about 24-29 nucleotides in length, e.g., 20, 21, 22, 23, 24, 25, 26, 27, 28, 29, or 30 nucleotides in length. Non-limiting examples of siRNAs include ribozymes, RNA decoys, short hairpin RNAs (shRNA), micro RNAs (miRNA) and small nucleolar RNAs (snoRNA).

A "VCP gene" as referred to herein includes any of the recombinant or naturally-occurring forms of the gene encoding valosin-containing protein (VCP), homologs or variants thereof that maintain VCP activity (e.g. within at least 50%, 80%, 90%, 95%, 96%, 97%, 98%, 99% or 100% activity compared to VCP). In some aspects, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring VCP polypeptide. In embodiments, the VCP gene is substantially identical to the nucleic acid identified by the ENSEMBLE reference number ENSG00000165280 or a variant having substantial identity thereto. In embodiments, the VCP gene is identified as the nucleic acid identified by the NCBI reference number GI: 169881236. In embodiments, the VCP gene includes the sequence of SEQ ID NO:7. In embodiments, the VCP gene is the sequence of SEQ ID NO:7. In embodiments, VCP exon 4 corresponds to the sequence of nucleotide position 7,033 to 7,175 of SEQ ID NO: 7. In embodiments, VCP exon 5 corresponds to the sequence of nucleotide position 8,469 to 8,599 of SEQ ID NO: 7. In embodiments, VCP intron 4 corresponds to the sequence of nucleotide position 7,176 to 8,468 of SEQ ID NO: 7.

A "VCP pre-mRNA" as referred to herein includes any of the recombinant or naturally-occurring forms of an unspliced mRNA sequence that are translated from a VCP gene and coding for a VCP protein or fragment thereof. In embodiments, the VCP pre-mRNA includes the sequence of SEQ ID NO:8. In embodiments, the VCP pre-mRNA is the sequence of SEQ ID NO:8.

A "VCP protein" as referred to herein includes any of the recombinant or naturally-occurring forms of the valosin-containing protein (VCP) or variants or homologs thereof that maintain VCP protein activity (e.g. within at least 50%, 80%, 90%, 95%, 96%, 97%, 98%, 99% or 100% activity compared to VCP protein). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring VCP protein. In embodiments, the VCP protein is substantially identical to the protein identified by the NCBI reference number GI:6094447 or a variant or homolog having substantial identity thereto. In embodiments, the VCP protein is the protein identified by the UniProt reference number P55072 or a variant or homolog having substantial identity thereto. In embodiments, the VCP protein includes the sequences of SEQ ID NO:9. In embodiments, the VCP protein is the sequence of SEQ ID NO:9.

The terms "treating", or "treatment" refer to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; or improving a patient's physical or mental well-being. The treatment or amelioration of symptoms can be based on objective or subjective parameters, including the results of a physical examination, neuropsychiatric exams, and/or a psychiatric evaluation. The term "treating" and conjugations thereof, include prevention of an injury, pathology, condition, or disease.

An "effective amount" is an amount sufficient to accomplish a stated purpose (e.g., achieve the effect for which it is administered, treat a disease, reduce enzyme activity, increase enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the methods disclosed herein should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In embodiments, a control is the measurement of the activity of a protein in the absence of a compound as described herein (including embodiments and examples).

"Contacting" is used in accordance with its plain ordinary meaning and refers to the process of allowing at least two distinct species (e.g., chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme. Contacting may include allowing a compound described herein to interact with a protein or enzyme that is involved in a signaling pathway.

As defined herein, the term "inhibition", "inhibit", "inhibiting" and the like in reference to a protein-inhibitor or nucleic acid sequence-inhibitor interaction (e.g., an acceptor or donor splice site sequence and an antisense VCP exon 4 or VCP exon 5 nucleic acid provided herein) means negatively affecting (e.g., decreasing) the expression, activity or function of the protein or nucleic acid sequence relative to the expression, activity or function of the protein or nucleic acid sequence in the absence of the inhibitor (antisense VCP exon 4 or VCP exon 5 nucleic acid). Inhibition may refer to reduction of a disease or symptoms of disease. Inhibition may refer to a reduction in the activity of a particular protein or nucleic acid target. Inhibition may refer to a reduction in the expression of a particular protein or nucleic acid target or fragment thereof. Thus, inhibition includes, at least in part, partially or totally blocking stimulation, decreasing, preventing, or delaying activation, or inactivating, desensitizing, or down-regulating signal transduction or enzymatic activity or the amount of a protein. The inhibited expression or activity of VCP exon 4 or VCP exon 5 can be 10%, 20%, 30%, 40%, 50%, 60%, 70%, 80%, 90% or less than that in a control. In certain instances, the inhibition is 1.5-fold, 2-fold, 3-fold, 4-fold, 5-fold, 10-fold, or more in comparison to a control.

The term "modulator" refers to a composition that increases or decreases the level of a target molecule or the function of a target molecule or the physical state of the target of the molecule.

The term "modulate" is used in accordance with its plain ordinary meaning and refers to the act of changing or varying one or more properties. "Modulation" refers to the process of changing or varying one or more properties. For example, a modulator of a target protein changes by increasing or decreasing a property or function of the target molecule or the amount of the target molecule. A modulator of a disease decreases a symptom, cause, or characteristic of the targeted disease.

"Selective" or "selectivity" or the like of a compound refers to the compound's ability to discriminate between molecular targets. "Specific", "specifically", "specificity", or the like of a compound refers to the compound's ability to cause a particular action, such as inhibition, to a particular molecular target with minimal or no action to other proteins in the cell.

"Pharmaceutically acceptable excipient" and "pharmaceutically acceptable carrier" refer to a substance that aids the administration of an active agent to and absorption by a subject and can be included in the compositions disclosed herein without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds disclosed herein. One of skill in the art will recognize that other pharmaceutical excipients are useful in the compositions and methods disclosed herein.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions disclosed herein may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions disclosed herein can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions disclosed herein into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions can also be delivered as nanoparticles.

Pharmaceutical compositions may include compositions wherein the active ingredient (e.g., compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds disclosed herein. Adjustment and manipulation of established dosages (e.g., frequency and duration) are well within the ability of those skilled in the art.

The compounds described herein can be used in combination with one another, with other active drugs known to be useful in treating a disease (e.g., anti-cancer drugs) or with adjunctive agents that may not be effective alone, but may contribute to the efficacy of the active agent. Thus, the compounds described herein may be co-administered with one another or with other active drugs known to be useful in treating a disease.

By "co-administer" it is meant that a compound described herein is administered at the same time, just prior to, or just after the administration of one or more additional therapies, for example, an anticancer agent as described herein. The compounds described herein can be administered alone or can be co-administered to the patient. Co-administration is meant to include simultaneous or sequential administration of the compound individually or in combination (more than one compound or agent). Thus, the preparations can also be combined, when desired, with other active substances (e.g., anticancer agents).

Co-administration includes administering one active agent (e.g., a complex described herein) within 0.5, 1, 2, 4, 6, 8, 10, 12, 16, 20, or 24 hours of a second active agent (e.g., anti-cancer agents). Also contemplated herein, are embodiments, where co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. Co-administration can be accomplished by co-formulation, i.e., preparing a single pharmaceutical composition including both active agents. In other embodiments, the active agents can be formulated separately. The active and/or adjunctive agents may be linked or conjugated to one another. The compounds described herein may be combined with treatments for cancer such as chemotherapy or radiation therapy.

The term "associated" or "associated with" in the context of a substance or substance activity or function associated with a disease means that the disease is caused by (in whole or in part), a symptom of the disease is caused by (in whole or in part) the substance or substance activity or function, or a side-effect of the compound (e.g., toxicity) is caused by (in whole or in part) the substance or substance activity or function.

"Patient," "subject," "patient in need thereof," and "subject in need thereof" are herein used interchangeably and refer to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human. A "cancer-patient" is a patient suffering from, or prone to developing cancer.

"Disease," "disorder" or "condition" refer to a state of being or health status of a patient or subject capable of being treated with the compounds or methods provided herein. Disease as used herein may refer to cancer.

As used herein, the term "neurodegenerative disease" refers to a disease or condition in which the function of a subject's nervous system is affected. Non-limiting examples of neurodegenerative diseases that may be treated with a compound or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Straussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoffs disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, Tabes dorsalis, drug-induced Parkinsonism, progressive supranuclear palsy, corticobasal degeneration, multiple system atrophy, Idiopathic Parkinson's disease, Autosomal dominant Parkinson disease, Parkinson disease, familial, type 1 (PARK1), Parkinson disease 3, autosomal dominant Lewy body (PARK3), Parkinson disease 4, autosomal dominant Lewy body (PARK4), Parkinson disease 5 (PARK5), Parkinson disease 6, autosomal recessive early-onset (PARK6), Parkinson disease 2, autosomal recessive juvenile (PARK2), Parkinson disease 7, autosomal recessive early-onset (PARK7), Parkinson disease 8 (PARK8), Parkinson disease 9 (PARK9), Parkinson disease 10 (PARK10), Parkinson disease 11 (PARK11), Parkinson disease 12 (PARK12), or Parkinson disease 13 (PARK13).

In embodiments, the neurodegenerative disease is a VCP-associated neurodegenerative disease. A "VCP-associated" neurodegenerative disease as provided herein refers to a neurodegenerative disease caused by the function or activity of an aberrant VCP protein, aberrant VCP gene, fragments, variants or homologs thereof. The term "aberrant" as used herein refers to different from normal. When used to describe protein function (e.g., VCP protein function), aberrant refers to the function of VCP that is greater or less than a normal control or the average of normal non-diseased control samples. Aberrant activity may refer to an amount of activity (VCP activity) that results in a disease, wherein returning the aberrant activity to a normal or non-disease-associated amount (e.g. by using a method as described herein), results in reduction of the disease or one or more disease symptoms. Aberrant activity may further refer to an amount of gene expression (VCP gene expression) that results in a disease, wherein returning the aberrant activity to a normal or non-disease-associated amount (e.g. by using a method as described herein), results in reduction of the disease or one or more disease symptoms.

II. Methods and Compositions

The methods provided herein, including embodiments thereof, are, inter alia, useful for treating neurodegenerative disease caused by aberrant VCP protein function. In embodiments, the neurodegenerative disease is caused by a mutation in the VCP gene. In embodiments, the mutation is at a position corresponding to amino acid position 155 in the VCP protein. In embodiments, the mutation is at a position corresponding to amino acid position 155 in SEQ ID NO:9. In embodiments, amino acid residue corresponding to amino acid position 155 is histidine. The methods provided herein apply exon skipping methodology to excise the nucleic acid sequence encoding for aberrant VCP protein function (e.g., nucleic acid sequences encoding a mutation in the VCP gene), thereby treating the VCP-associated neurodegenerative disease. In particular, Applicants have shown that using antisense nucleic acids capable of binding VCP exon 4 and VCP exon 5 as well as adjacent intron sequences thereof, successfully inhibits expression of the nucleic acid sequence encoding for aberrant VCP protein function and thereby treats the VCP-associated neurodegenerative disease.

In one aspect, there is provided a method of treating a VCP-associated neurodegenerative disease in a subject in need thereof. The method includes administering to the subject a therapeutically effective amount of an antisense VCP exon 4 nucleic acid or an antisense VCP exon 5 nucleic acid.

In another aspect, there is provided a method of treating a VCP-associated neurodegenerative disease in a subject in need thereof. The method includes administering to the subject a therapeutically effective amount of an antisense VCP exon 4 nucleic acid.

In another aspect, there is provided a method of treating a VCP-associated neurodegenerative disease in a subject in need thereof. The method includes administering to the subject a therapeutically effective amount of an antisense VCP exon 5 nucleic acid.

An "antisense VCP exon 4 nucleic acid" as provided herein refers to an antisense nucleic acid capable of binding (hybridizing) to a VCP gene sequence or a VCP pre-mRNA. Thus, the antisense VCP exon 4 nucleic acid is complementary to the VCP gene sequence (e.g., SEQ ID NO:7) or the VCP pre-mRNA sequence (e.g, SEQ ID NO:8). The antisense VCP exon 4 nucleic acid provided herein is capable of binding (hybridizing) to nucleotides of exon 4 and/or intron 3 of the VCP gene or a fragment, homolog or variant thereof. Where the VCP exon 4 nucleic acid binds exon 4 and/or intron 3 it binds at least 5 nucleotides of exon 4 and/or intron 3.

In embodiments, the antisense VCP exon 4 nucleic acid binds to nucleotides of sequence of SEQ ID NO:7. The antisense VCP exon 4 nucleic acid may bind a continuous sequence of at least 10 nucleotides of SEQ ID NO:7. In embodiments, the antisense VCP exon 4 nucleic acid binds a continuous sequence of at least 11 nucleotides of SEQ ID NO:7. In embodiments, the antisense VCP exon 4 nucleic acid binds a continuous sequence of at least 12 nucleotides of SEQ ID NO:7. In embodiments, the antisense VCP exon 4 nucleic acid binds a continuous sequence of at least 13 nucleotides of SEQ ID NO:7. In embodiments, the antisense VCP exon 4 nucleic acid binds a continuous sequence of at least 14 nucleotides of SEQ ID NO:7. In embodiments, the antisense VCP exon 4 nucleic acid binds a continuous sequence of at least 15 nucleotides of SEQ ID NO:7. In embodiments, the antisense VCP exon 4 nucleic acid binds a continuous sequence of at least 16 nucleotides of SEQ ID NO:7. In embodiments, the antisense VCP exon 4 nucleic acid binds a continuous sequence of at least 17 nucleotides of SEQ ID NO:7. In embodiments, the antisense VCP exon 4 nucleic acid binds a continuous sequence of at least 18 nucleotides of SEQ ID NO:7. In embodiments, the antisense VCP exon 4 nucleic acid binds a continuous sequence of at least 19 nucleotides of SEQ ID NO:7. In embodiments, the antisense VCP exon 4 nucleic acid binds a continuous sequence of at least 20 nucleotides of SEQ ID NO:7. In embodiments, the antisense VCP exon 4 nucleic acid binds a continuous sequence of at least 21 nucleotides of SEQ ID NO:7. In embodiments, the antisense VCP exon 4 nucleic acid binds a continuous sequence of at least 22 nucleotides of SEQ ID NO:7. In embodiments, the antisense VCP exon 4 nucleic acid binds a continuous sequence of at least 23 nucleotides of SEQ ID NO:7. In embodiments, the antisense VCP exon 4 nucleic acid binds a continuous sequence of at least 24 nucleotides of SEQ ID NO:7. In embodiments, the antisense VCP exon 4 nucleic acid binds a continuous sequence of at least 25 nucleotides of SEQ ID NO:7. In embodiments, the antisense VCP exon 4 nucleic acid binds a continuous sequence of at least 26 nucleotides of SEQ ID NO:7. In embodiments, the antisense VCP exon 4 nucleic acid binds a continuous sequence of at least 27 nucleotides of SEQ ID NO:7. In embodiments, the antisense VCP exon 4 nucleic acid binds a continuous sequence of at least 28 nucleotides of SEQ ID NO:7. In embodiments, the antisense VCP exon 4 nucleic acid binds a continuous sequence of at least 29 nucleotides of SEQ ID NO:7. In embodiments, the antisense VCP exon 4 nucleic acid binds a continuous sequence of at least 30 nucleotides of SEQ ID NO:7. In embodiments, the antisense VCP exon 4 nucleic acid binds a continuous sequence of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides of SEQ ID NO:7. In further embodiments, the antisense VCP exon 4 nucleic acid has a sequence identity of at least 80%, 85%, 90%, 91%, 92%, 93%, 94%, 95%, 96%, 97%, 98% or 99% to the continuous sequence. In embodiments, the antisense VCP exon 4 nucleic acid binds a continuous sequence of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides of the sequence corresponding to nucleotide position 7033 to 8599 of SEQ ID NO:7.

The antisense VCP exon 4 nucleic acid may bind a continuous sequence of about 10 nucleotides of SEQ ID NO:7. In embodiments, the antisense VCP exon 4 nucleic acid binds a continuous sequence of about 11 nucleotides of SEQ ID NO:7. In embodiments, the antisense VCP exon 4 nucleic acid binds a continuous sequence of about 12 nucleotides of SEQ ID NO:7. In embodiments, the antisense VCP exon 4 nucleic acid binds a continuous sequence of about 13 nucleotides of SEQ ID NO:7. In embodiments, the antisense VCP exon 4 nucleic acid binds a continuous sequence of about 14 nucleotides of SEQ ID NO:7. In embodiments, the antisense VCP exon 4 nucleic acid binds a continuous sequence of about 15 nucleotides of SEQ ID NO:7. In embodiments, the antisense VCP exon 4 nucleic acid binds a continuous sequence of about 16 nucleotides of SEQ ID NO:7. In embodiments, the antisense VCP exon 4 nucleic acid binds a continuous sequence of about 17 nucleotides of SEQ ID NO:7. In embodiments, the antisense VCP exon 4 nucleic acid binds a continuous sequence of about 18 nucleotides of SEQ ID NO:7. In embodiments, the antisense VCP exon 4 nucleic acid binds a continuous sequence of about 19 nucleotides of SEQ ID NO:7. In embodiments, the antisense VCP exon 4 nucleic acid binds a continuous sequence of about 20 nucleotides of SEQ ID NO:7. In embodiments, the antisense VCP exon 4 nucleic acid binds a continuous sequence of about 21 nucleotides of SEQ ID NO:7. In embodiments, the antisense VCP exon 4 nucleic acid binds a continuous sequence of about 22 nucleotides of SEQ ID NO:7. In embodiments, the antisense VCP exon 4 nucleic acid binds a continuous sequence of about 23 nucleotides of SEQ ID NO:7. In embodiments, the antisense VCP exon 4 nucleic acid binds a continuous sequence of about 24 nucleotides of SEQ ID NO:7. In embodiments, the antisense VCP exon 4 nucleic acid binds a continuous sequence of about 25 nucleotides of SEQ ID NO:7. In embodiments, the antisense VCP exon 4 nucleic acid binds a continuous sequence of about 26 nucleotides of SEQ ID NO:7. In embodiments, the antisense VCP exon 4 nucleic acid binds a continuous sequence of about 27 nucleotides of SEQ ID NO:7. In embodiments, the antisense VCP exon 4 nucleic acid binds a continuous sequence of about 28 nucleotides of SEQ ID NO:7. In embodiments, the antisense VCP exon 4 nucleic acid binds a continuous sequence of about 29 nucleotides of SEQ ID NO:7. In embodiments, the antisense VCP exon 4 nucleic acid binds a continuous sequence of about 30 nucleotides of SEQ ID NO:7. In embodiments, the antisense VCP exon 4 nucleic acid binds a continuous sequence of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides of SEQ ID NO:7. In further embodiments, the antisense VCP exon 4 nucleic acid has a sequence identity of at least 80%, 85%, 90%, 91%, 92%, 93%, 94%, 95%, 96%, 97%, 98% or 99% to the continuous sequence. In embodiments, the antisense VCP exon 4 nucleic acid has at least 80%, 85%, 90%, 95%, 96%, 97%, 98%, 99% or 100% sequence identity across 10, 15, 20, 25, 26, 27, or 28 continuous nucleotides of SEQ ID NO:7.

In embodiments, the antisense VCP exon 4 nucleic acid has at least 80% sequence identity across 10, 15, 20, 25, 26, 27, or 28 continuous nucleotides of SEQ ID NO:7. In embodiments, the antisense VCP exon 4 nucleic acid has at least 85% sequence identity across 10, 15, 20, 25, 26, 27, or 28 continuous nucleotides of SEQ ID NO:7. In embodiments, the antisense VCP exon 4 nucleic acid has at least 90% sequence identity across 10, 15, 20, 25, 26, 27, or 28 continuous nucleotides of SEQ ID NO:7. In embodiments, the antisense VCP exon 4 nucleic acid has at least 91% sequence identity across 10, 15, 20, 25, 26, 27, or 28 continuous nucleotides of SEQ ID NO:7. In embodiments, the antisense VCP exon 4 nucleic acid has at least 92% sequence identity across 10, 15, 20, 25, 26, 27, or 28 continuous nucleotides of SEQ ID NO:7. In embodiments, the antisense VCP exon 4 nucleic acid has at least 93% sequence identity across 10, 15, 20, 25, 26, 27, or 28 continuous nucleotides of SEQ ID NO:7. In embodiments, the antisense VCP exon 4 nucleic acid has at least 94% sequence identity across 10, 15, 20, 25, 26, 27, or 28 continuous nucleotides of SEQ ID NO:7. In embodiments, the antisense VCP exon 4 nucleic acid has at least 95% sequence identity across 10, 15, 20, 25, 26, 27, or 28 continuous nucleotides of SEQ ID NO:7. In embodiments, the antisense VCP exon 4 nucleic acid has at least 96% sequence identity across 10, 15, 20, 25, 26, 27, or 28 continuous nucleotides of SEQ ID NO:7. In embodiments, the antisense VCP exon 4 nucleic acid has at least 97% sequence identity across 10, 15, 20, 25, 26, 27, or 28 continuous nucleotides of SEQ ID NO:7. In embodiments, the antisense VCP exon 4 nucleic acid has at least 98% sequence identity across 10, 15, 20, 25, 26, 27, or 28 continuous nucleotides of SEQ ID NO:7. In embodiments, the antisense VCP exon 4 nucleic acid has at least 99% sequence identity across 10, 15, 20, 25, 26, 27, or 28 continuous nucleotides of SEQ ID NO:7. The antisense VCP exon 4 nucleic acid may bind a continuous sequence of about 10 nucleotides of SEQ ID NO: 10. In embodiments, the antisense VCP exon 4 nucleic acid binds a continuous sequence of about 11 nucleotides of SEQ ID NO: 10. In embodiments, the antisense VCP exon 4 nucleic acid binds a continuous sequence of about 12 nucleotides of SEQ ID NO: 10. In embodiments, the antisense VCP exon 4 nucleic acid binds a continuous sequence of about 13 nucleotides of SEQ ID NO: 10. In embodiments, the antisense VCP exon 4 nucleic acid binds a continuous sequence of about 14 nucleotides of SEQ ID NO: 10. In embodiments, the antisense VCP exon 4 nucleic acid binds a continuous sequence of about 15 nucleotides of SEQ ID NO:10. In embodiments, the antisense VCP exon 4 nucleic acid binds a continuous sequence of about 16 nucleotides of SEQ ID NO: 10. In embodiments, the antisense VCP exon 4 nucleic acid binds a continuous sequence of about 17 nucleotides of SEQ ID NO: 10. In embodiments, the antisense VCP exon 4 nucleic acid binds a continuous sequence of about 18 nucleotides of SEQ ID NO: 10. In embodiments, the antisense VCP exon 4 nucleic acid binds a continuous sequence of about 19 nucleotides of SEQ ID NO: 10. In embodiments, the antisense VCP exon 4 nucleic acid binds a continuous sequence of about 20 nucleotides of SEQ ID NO: 10. In embodiments, the antisense VCP exon 4 nucleic acid binds a continuous sequence of about 21 nucleotides of SEQ ID NO: 10. In embodiments, the antisense VCP exon 4 nucleic acid binds a continuous sequence of about 22 nucleotides of SEQ ID NO: 10. In embodiments, the antisense VCP exon 4 nucleic acid binds a continuous sequence of about 23 nucleotides of SEQ ID NO: 10. In embodiments, the antisense VCP exon 4 nucleic acid binds a continuous sequence of about 24 nucleotides of SEQ ID NO: 10. In embodiments, the antisense VCP exon 4 nucleic acid binds a continuous sequence of about 25 nucleotides of SEQ ID NO: 10. In embodiments, the antisense VCP exon 4 nucleic acid binds a continuous sequence of about 26 nucleotides of SEQ ID NO: 10. In embodiments, the antisense VCP exon 4 nucleic acid binds a continuous sequence of about 27 nucleotides of SEQ ID NO: 10. In embodiments, the antisense VCP exon 4 nucleic acid binds a continuous sequence of about 28 nucleotides of SEQ ID NO: 10. In embodiments, the antisense VCP exon 4 nucleic acid binds a continuous sequence of about 29 nucleotides of SEQ ID NO: 10. In embodiments, the antisense VCP exon 4 nucleic acid binds a continuous sequence of about 30 nucleotides of SEQ ID NO: 10. In embodiments, the antisense VCP exon 4 nucleic acid binds a continuous sequence of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides of SEQ ID NO: 10. In further embodiments, the antisense VCP exon 4 nucleic acid has a sequence identity of at least 80%, 85%, 90%, 91%, 92%, 93%, 94%, 95%, 96%, 97%, 98% or 99% to the continuous sequence. In embodiments, the antisense VCP exon 4 nucleic acid has at least 80%, 85%, 90%, 95%, 96%, 97%, 98%, 99% or 100% sequence identity across 10, 15, 20, 25, 26, 27, or 28 continuous nucleotides of SEQ ID NO: 10.

An "antisense VCP exon 5 nucleic acid" as provided herein refers to an antisense nucleic acid capable of binding (hybridizing) to a VCP gene sequence or a VCP pre-mRNA. Thus, the antisense VCP exon 5 nucleic acid is complementary to the VCP gene sequence (e.g., SEQ ID NO:7) or the VCP pre-mRNA sequence. The antisense VCP exon 5 nucleic acid provided herein is capable of binding (hybridizing) to nucleotides of exon 5 and/or intron 4 of the VCP gene or a fragment, homolog or variant thereof. Where the VCP exon 4 nucleic acid binds exon 5 and/or intron 4 it binds at least 5 nucleotides of exon 5 and/or intron 4.

In embodiments, the antisense VCP exon 5 nucleic acid binds to nucleotides of sequence of SEQ ID NO:7. The antisense VCP exon 5 nucleic acid may bind a continuous sequence of at least 10 nucleotides of SEQ ID NO:7. In embodiments, the antisense VCP exon 5 nucleic acid binds a continuous sequence of at least 11 nucleotides of SEQ ID NO:7. In embodiments, the antisense VCP exon 5 nucleic acid binds a continuous sequence of at least 12 nucleotides of SEQ ID NO:7. In embodiments, the antisense VCP exon 5 nucleic acid binds a continuous sequence of at least 13 nucleotides of SEQ ID NO:7. In embodiments, the antisense VCP exon 5 nucleic acid binds a continuous sequence of at least 14 nucleotides of SEQ ID NO:7. In embodiments, the antisense VCP exon 5 nucleic acid binds a continuous sequence of at least 15 nucleotides of SEQ ID NO:7. In embodiments, the antisense VCP exon 5 nucleic acid binds a continuous sequence of at least 16 nucleotides of SEQ ID NO:7. In embodiments, the antisense VCP exon 5 nucleic acid binds a continuous sequence of at least 17 nucleotides of SEQ ID NO:7. In embodiments, the antisense VCP exon 5 nucleic acid binds a continuous sequence of at least 18 nucleotides of SEQ ID NO:7. In embodiments, the antisense VCP exon 5 nucleic acid binds a continuous sequence of at least 19 nucleotides of SEQ ID NO:7. In embodiments, the antisense VCP exon 5 nucleic acid binds a continuous sequence of at least 20 nucleotides of SEQ ID NO:7. In embodiments, the antisense VCP exon 5 nucleic acid binds a continuous sequence of at least 21 nucleotides of SEQ ID NO:7. In embodiments, the antisense VCP exon 5 nucleic acid binds a continuous sequence of at least 22 nucleotides of SEQ ID NO:7. In embodiments, the antisense VCP exon 5 nucleic acid binds a continuous sequence of at least 23 nucleotides of SEQ ID NO:7. In embodiments, the antisense VCP exon 5 nucleic acid binds a continuous sequence of at least 24 nucleotides of SEQ ID NO:7. In embodiments, the antisense VCP exon 5 nucleic acid binds a continuous sequence of at least 25 nucleotides of SEQ ID NO:7. In embodiments, the antisense VCP exon 5 nucleic acid binds a continuous sequence of at least 26 nucleotides of SEQ ID NO:7. In embodiments, the antisense VCP exon 5 nucleic acid binds a continuous sequence of at least 27 nucleotides of SEQ ID NO:7. In embodiments, the antisense VCP exon 5 nucleic acid binds a continuous sequence of at least 28 nucleotides of SEQ ID NO:7. In embodiments, the antisense VCP exon 5 nucleic acid binds a continuous sequence of at least 29 nucleotides of SEQ ID NO:7. In embodiments, the antisense VCP exon 5 nucleic acid binds a continuous sequence of at least 30 nucleotides of SEQ ID NO:7. In embodiments, the antisense VCP exon 5 nucleic acid binds a continuous sequence of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides of SEQ ID NO:7. In further embodiments, the antisense VCP exon 5 nucleic acid has a sequence identity of at least 80%, 85%, 90%, 91%, 92%, 93%, 94%, 95%, 96%, 97%, 98% or 99% to the continuous sequence. In one further embodiment, the pre-mRNA has a sequence identity of at least 80%, 85%, 90%, 91%, 92%, 93%, 94%, 95%, 96%, 97%, 98%, 99% or 100% to the sequence of SEQ ID NO:7. In embodiments, the antisense VCP exon 4 nucleic acid binds a continuous sequence of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides of the sequence corresponding to nucleotide position 7033 to 8599 of SEQ ID NO:7.

In embodiments, the antisense VCP exon 5 nucleic acid binds a continuous sequence of about 11 nucleotides of SEQ ID NO:7. In embodiments, the antisense VCP exon 5 nucleic acid binds a continuous sequence of about 12 nucleotides of SEQ ID NO:7. In embodiments, the antisense VCP exon 5 nucleic acid binds a continuous sequence of about 13 nucleotides of SEQ ID NO:7. In embodiments, the antisense VCP exon 5 nucleic acid binds a continuous sequence of about 14 nucleotides of SEQ ID NO:7. In embodiments, the antisense VCP exon 5 nucleic acid binds a continuous sequence of about 15 nucleotides of SEQ ID NO:7. In embodiments, the antisense VCP exon 5 nucleic acid binds a continuous sequence of about 16 nucleotides of SEQ ID NO:7. In embodiments, the antisense VCP exon 5 nucleic acid binds a continuous sequence of about 17 nucleotides of SEQ ID NO:7. In embodiments, the antisense VCP exon 5 nucleic acid binds a continuous sequence of about 18 nucleotides of SEQ ID NO:7. In embodiments, the antisense VCP exon 5 nucleic acid binds a continuous sequence of about 19 nucleotides of SEQ ID NO:7. In embodiments, the antisense VCP exon 5 nucleic acid binds a continuous sequence of about 20 nucleotides of SEQ ID NO:7. In embodiments, the antisense VCP exon 5 nucleic acid binds a continuous sequence of about 21 nucleotides of SEQ ID NO:7. In embodiments, the antisense VCP exon 5 nucleic acid binds a continuous sequence of about 22 nucleotides of SEQ ID NO:7. In embodiments, the antisense VCP exon 5 nucleic acid binds a continuous sequence of about 23 nucleotides of SEQ ID NO:7. In embodiments, the antisense VCP exon 5 nucleic acid binds a continuous sequence of about 24 nucleotides of SEQ ID NO:7. In embodiments, the antisense VCP exon 5 nucleic acid binds a continuous sequence of about 25 nucleotides of SEQ ID NO:7. In embodiments, the antisense VCP exon 5 nucleic acid binds a continuous sequence of about 26 nucleotides of SEQ ID NO:7. In embodiments, the antisense VCP exon 5 nucleic acid binds a continuous sequence of about 27 nucleotides of SEQ ID NO:7. In embodiments, the antisense VCP exon 5 nucleic acid binds a continuous sequence of about 28 nucleotides of SEQ ID NO:7. In embodiments, the antisense VCP exon 5 nucleic acid binds a continuous sequence of about 29 nucleotides of SEQ ID NO:7. In embodiments, the antisense VCP exon 5 nucleic acid binds a continuous sequence of about 30 nucleotides of SEQ ID NO:7. In embodiments, the antisense VCP exon 5 nucleic acid binds a continuous sequence of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides of SEQ ID NO:7. In further embodiments, the antisense VCP exon 5 nucleic acid has a sequence identity of at least 80%, 85%, 90%, 91%, 92%, 93%, 94%, 95%, 96%, 97%, 98% or 99% to the continuous sequence. In one further embodiment, the pre-mRNA has a sequence identity of at least 80%, 85%, 90%, 91%, 92%, 93%, 94%, 95%, 96%, 97%, 98%, 99% or 100% to the sequence of SEQ ID NO:7. In embodiments, the antisense VCP exon 5 nucleic acid has at least 80%, 85%, 90%, 95%, 96%, 97%, 98%, 99% or 100% sequence identity across 10, 15, 20, 25, 26, 27, or 28 continuous nucleotides of SEQ ID NO:7.

The antisense VCP exon 5 nucleic acid may bind a continuous sequence of about 10 nucleotides of SEQ ID NO: 10. In embodiments, the antisense VCP exon 5 nucleic acid binds a continuous sequence of about 11 nucleotides of SEQ ID NO: 10. In embodiments, the antisense VCP exon 5 nucleic acid binds a continuous sequence of about 12 nucleotides of SEQ ID NO: 10. In embodiments, the antisense VCP exon 5 nucleic acid binds a continuous sequence of about 13 nucleotides of SEQ ID NO: 10. In embodiments, the antisense VCP exon 5 nucleic acid binds a continuous sequence of about 14 nucleotides of SEQ ID NO: 10. In embodiments, the antisense VCP exon 5 nucleic acid binds a continuous sequence of about 15 nucleotides of SEQ ID NO:10. In embodiments, the antisense VCP exon 5 nucleic acid binds a continuous sequence of about 16 nucleotides of SEQ ID NO: 10. In embodiments, the antisense VCP exon 5 nucleic acid binds a continuous sequence of about 17 nucleotides of SEQ ID NO:10. In embodiments, the antisense VCP exon 5 nucleic acid binds a continuous sequence of about 18 nucleotides of SEQ ID NO:10. In embodiments, the antisense VCP exon 5 nucleic acid binds a continuous sequence of about 19 nucleotides of SEQ ID NO: 10. In embodiments, the antisense VCP exon 5 nucleic acid binds a continuous sequence of about 20 nucleotides of SEQ ID NO: 10. In embodiments, the antisense VCP exon 5 nucleic acid binds a continuous sequence of about 21 nucleotides of SEQ ID NO: 10. In embodiments, the antisense VCP exon 5 nucleic acid binds a continuous sequence of about 22 nucleotides of SEQ ID NO: 10. In embodiments, the antisense VCP exon 5 nucleic acid binds a continuous sequence of about 23 nucleotides of SEQ ID NO: 10. In embodiments, the antisense VCP exon 5 nucleic acid binds a continuous sequence of about 24 nucleotides of SEQ ID NO: 10. In embodiments, the antisense VCP exon 5 nucleic acid binds a continuous sequence of about 25 nucleotides of SEQ ID NO: 10. In embodiments, the antisense VCP exon 5 nucleic acid binds a continuous sequence of about 26 nucleotides of SEQ ID NO: 10. In embodiments, the antisense VCP exon 5 nucleic acid binds a continuous sequence of about 27 nucleotides of SEQ ID NO: 10. In embodiments, the antisense VCP exon 5 nucleic acid binds a continuous sequence of about 28 nucleotides of SEQ ID NO: 10. In embodiments, the antisense VCP exon 5 nucleic acid binds a continuous sequence of about 29 nucleotides of SEQ ID NO: 10. In embodiments, the antisense VCP exon 5 nucleic acid binds a continuous sequence of about 30 nucleotides of SEQ ID NO: 10. In embodiments, the antisense VCP exon 5 nucleic acid binds a continuous sequence of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides of SEQ ID NO: 10. In further embodiments, the antisense VCP exon 5 nucleic acid has a sequence identity of at least 80%, 85%, 90%, 91%, 92%, 93%, 94%, 95%, 96%, 97%, 98% or 99% to the continuous sequence. In embodiments, the antisense VCP exon 5 nucleic acid has at least 80%, 85%, 90%, 95%, 96%, 97%, 98%, 99% or 100% sequence identity across 10, 15, 20, 25, 26, 27, or 28 continuous nucleotides of SEQ ID NO: 10.

In embodiments, the antisense VCP exon 5 nucleic acid has at least 80% sequence identity across 10, 15, 20, 25, 26, 27, or 28 continuous nucleotides of SEQ ID NO:7. In embodiments, the antisense VCP exon 5 nucleic acid has at least 85% sequence identity across 10, 15, 20, 25, 26, 27, or 28 continuous nucleotides of SEQ ID NO:7. In embodiments, the antisense VCP exon 5 nucleic acid has at least 90% sequence identity across 10, 15, 20, 25, 26, 27, or 28 continuous nucleotides of SEQ ID NO:7. In embodiments, the antisense VCP exon 5 nucleic acid has at least 91% sequence identity across 10, 15, 20, 25, 26, 27, or 28 continuous nucleotides of SEQ ID NO:7. In embodiments, the antisense VCP exon 5 nucleic acid has at least 92% sequence identity across 10, 15, 20, 25, 26, 27, or 28 continuous nucleotides of SEQ ID NO:7. In embodiments, the antisense VCP exon 5 nucleic acid has at least 93% sequence identity across 10, 15, 20, 25, 26, 27, or 28 continuous nucleotides of SEQ ID NO:7. In embodiments, the antisense VCP exon 5 nucleic acid has at least 94% sequence identity across 10, 15, 20, 25, 26, 27, or 28 continuous nucleotides of SEQ ID NO:7. In embodiments, the antisense VCP exon 5 nucleic acid has at least 95% sequence identity across 10, 15, 20, 25, 26, 27, or 28 continuous nucleotides of SEQ ID NO:7. In embodiments, the antisense VCP exon 5 nucleic acid has at least 96% sequence identity across 10, 15, 20, 25, 26, 27, or 28 continuous nucleotides of SEQ ID NO:7. In embodiments, the antisense VCP exon 5 nucleic acid has at least 97% sequence identity across 10, 15, 20, 25, 26, 27, or 28 continuous nucleotides of SEQ ID NO:7. In embodiments, the antisense VCP exon 5 nucleic acid has at least 98% sequence identity across 10, 15, 20, 25, 26, 27, or 28 continuous nucleotides of SEQ ID NO:7. In embodiments, the antisense VCP exon 5 nucleic acid has at least 99% sequence identity across 10, 15, 20, 25, 26, 27, or 28 continuous nucleotides of SEQ ID NO:7.

In embodiments, the antisense VCP exon 4 nucleic acid sequence is about 10 nucleotides in length. In embodiments, the antisense VCP exon 4 nucleic acid sequence about is 12 nucleotides in length. In embodiments, the antisense VCP exon 4 nucleic acid sequence is about 14 nucleotides in length. In embodiments, the antisense VCP exon 4 nucleic acid sequence is about 16 nucleotides in length. In embodiments, the antisense VCP exon 4 nucleic acid sequence is about 18 nucleotides in length. In embodiments, the antisense VCP exon 4 nucleic acid sequence is about 20 nucleotides in length. In embodiments, the antisense VCP exon 4 nucleic acid sequence is about 22 nucleotides in length. In embodiments, the antisense VCP exon 4 nucleic acid sequence is about 24 nucleotides in length. In embodiments, the antisense VCP exon 4 nucleic acid sequence is about 26 nucleotides in length. In embodiments, the antisense VCP exon 4 nucleic acid sequence is about 28 nucleotides in length. In embodiments, the antisense VCP exon 4 nucleic acid sequence is about 30 nucleotides in length. In embodiments, the antisense VCP exon 4 nucleic acid sequence is about 32 nucleotides in length. In embodiments, the antisense VCP exon 4 nucleic acid sequence is about 34 nucleotides in length. In embodiments, the antisense VCP exon 4 nucleic acid sequence is about 36 nucleotides in length. In embodiments, the antisense VCP exon 4 nucleic acid sequence is about 38 nucleotides in length. In embodiments, the antisense VCP exon 4 nucleic acid sequence is about 40 nucleotides in length.

In embodiments, the antisense VCP exon 5 nucleic acid sequence is about 10 nucleotides in length. In embodiments, the antisense VCP exon 5 nucleic acid sequence about is 12 nucleotides in length. In embodiments, the antisense VCP exon 5 nucleic acid sequence is about 14 nucleotides in length. In embodiments, the antisense VCP exon 5 nucleic acid sequence is about 16 nucleotides in length. In embodiments, the antisense VCP exon 5 nucleic acid sequence is about 18 nucleotides in length. In embodiments, the antisense VCP exon 5 nucleic acid sequence is about 20 nucleotides in length. In embodiments, the antisense VCP exon 5 nucleic acid sequence is about 22 nucleotides in length. In embodiments, the antisense VCP exon 5 nucleic acid sequence is about 24 nucleotides in length. In embodiments, the antisense VCP exon 5 nucleic acid sequence is about 26 nucleotides in length. In embodiments, the antisense VCP exon 5 nucleic acid sequence is about 28 nucleotides in length. In embodiments, the antisense VCP exon 5 nucleic acid sequence is about 30 nucleotides in length. In embodiments, the antisense VCP exon 5 nucleic acid sequence is about 32 nucleotides in length. In embodiments, the antisense VCP exon 5 nucleic acid sequence is about 34 nucleotides in length. In embodiments, the antisense VCP exon 5 nucleic acid sequence is about 36 nucleotides in length. In embodiments, the antisense VCP exon 5 nucleic acid sequence is about 38 nucleotides in length. In embodiments, the antisense VCP exon 5 nucleic acid sequence is about 40 nucleotides in length.

In embodiments, the antisense VCP exon 5 nucleic acid has at least 80% sequence identity to SEQ ID NO: 1. In embodiments, the antisense VCP exon 5 nucleic acid has at least 85% sequence identity to SEQ ID NO: 1. In embodiments, the antisense VCP exon 5 nucleic acid has at least 90% sequence identity to SEQ ID NO: 1. In embodiments, the antisense VCP exon 5 nucleic acid has at least 91% sequence identity to SEQ ID NO:1. In embodiments, the antisense VCP exon 5 nucleic acid has at least 92% sequence identity to SEQ ID NO:1. In embodiments, the antisense VCP exon 5 nucleic acid has at least 93% sequence identity to SEQ ID NO: 1. In embodiments, the antisense VCP exon 5 nucleic acid has at least 94% sequence identity to SEQ ID NO: 1. In embodiments, the antisense VCP exon 5 nucleic acid has at least 95% sequence identity to SEQ ID NO: 1. In embodiments, the antisense VCP exon 5 nucleic acid has at least 96% sequence identity to SEQ ID NO: 1. In embodiments, the antisense VCP exon 5 nucleic acid has at least 97% sequence identity to SEQ ID NO: 1. In embodiments, the antisense VCP exon 5 nucleic acid has at least 98% sequence identity to SEQ ID NO:1. In embodiments, the antisense VCP exon 5 nucleic acid has at least 99% sequence identity to SEQ ID NO: 1. In embodiments, the antisense VCP exon 5 nucleic acid has at least 80%, 85%, 90%, 95%, 96%, 97%, 98%, 99% or 100% sequence identity across the whole sequence of to SEQ ID NO:1. In embodiments, the antisense VCP exon 5 nucleic acid has at least 80%, 85%, 90%, 95%, 96%, 97%, 98%, 99% or 100% sequence identity across 10, 15, 20, 25, 26, 27, or 28 continuous nucleotides of SEQ ID NO: 1.

In embodiments, the antisense VCP exon 5 nucleic acid has at least 80% sequence identity to SEQ ID NO:2. In embodiments, the antisense VCP exon 5 nucleic acid has at least 85% sequence identity to SEQ ID NO:2. In embodiments, the antisense VCP exon 5 nucleic acid has at least 90% sequence identity to SEQ ID NO:2. In embodiments, the antisense VCP exon 5 nucleic acid has at least 91% sequence identity to SEQ ID NO:2. In embodiments, the antisense VCP exon 5 nucleic acid has at least 92% sequence identity to SEQ ID NO:2. In embodiments, the antisense VCP exon 5 nucleic acid has at least 93% sequence identity to SEQ ID NO:2. In embodiments, the antisense VCP exon 5 nucleic acid has at least 94% sequence identity to SEQ ID NO:2. In embodiments, the antisense VCP exon 5 nucleic acid has at least 95% sequence identity to SEQ ID NO:2. In embodiments, the antisense VCP exon 5 nucleic acid has at least 96% sequence identity to SEQ ID NO:2. In embodiments, the antisense VCP exon 5 nucleic acid has at least 97% sequence identity to SEQ ID NO:2. In embodiments, the antisense VCP exon 5 nucleic acid has at least 98% sequence identity to SEQ ID NO:2. In embodiments, the antisense VCP exon 5 nucleic acid has at least 99% sequence identity to SEQ ID NO:2. In embodiments, the antisense VCP exon 5 nucleic acid has at least 80%, 85%, 90%, 95%, 96%, 97%, 98%, 99% or 100% sequence identity across the whole sequence of to SEQ ID NO:2. In embodiments, the antisense VCP exon 5 nucleic acid has at least 80%, 85%, 90%, 95%, 96%, 97%, 98%, 99% or 100% sequence identity across 10, 15, 20, 25, 26, 27, or 28 continuous nucleotides of SEQ ID NO:2.

In embodiments, the antisense VCP exon 5 nucleic acid has at least 80% sequence identity to SEQ ID NO:3. In embodiments, the antisense VCP exon 5 nucleic acid has at least 85% sequence identity to SEQ ID NO:3. In embodiments, the antisense VCP exon 5 nucleic acid has at least 90% sequence identity to SEQ ID NO:3. In embodiments, the antisense VCP exon 5 nucleic acid has at least 91% sequence identity to SEQ ID NO:3. In embodiments, the antisense VCP exon 5 nucleic acid has at least 92% sequence identity to SEQ ID NO:3. In embodiments, the antisense VCP exon 5 nucleic acid has at least 93% sequence identity to SEQ ID NO:3. In embodiments, the antisense VCP exon 5 nucleic acid has at least 94% sequence identity to SEQ ID NO:3. In embodiments, the antisense VCP exon 5 nucleic acid has at least 95% sequence identity to SEQ ID NO:3. In embodiments, the antisense VCP exon 5 nucleic acid has at least 96% sequence identity to SEQ ID NO:3. In embodiments, the antisense VCP exon 5 nucleic acid has at least 97% sequence identity to SEQ ID NO:3. In embodiments, the antisense VCP exon 5 nucleic acid has at least 98% sequence identity to SEQ ID NO:3. In embodiments, the antisense VCP exon 5 nucleic acid has at least 99% sequence identity to SEQ ID NO:3. In embodiments, the antisense VCP exon 5 nucleic acid has at least 80%, 85%, 90%, 95%, 96%, 97%, 98%, 99% or 100% sequence identity across the whole sequence of to SEQ ID NO:3. In embodiments, the antisense VCP exon 5 nucleic acid has at least 80%, 85%, 90%, 95%, 96%, 97%, 98%, 99% or 100% sequence identity across 10, 15, 20, 25, 26, 27, or 28 continuous nucleotides of SEQ ID NO:3.

In embodiments, the antisense VCP exon 5 nucleic acid has at least 80% sequence identity to SEQ ID NO:4. In embodiments, the antisense VCP exon 5 nucleic acid has at least 85% sequence identity to SEQ ID NO:4. In embodiments, the antisense VCP exon 5 nucleic acid has at least 90% sequence identity to SEQ ID NO:4. In embodiments, the antisense VCP exon 5 nucleic acid has at least 91% sequence identity to SEQ ID NO:4. In embodiments, the antisense VCP exon 5 nucleic acid has at least 92% sequence identity to SEQ ID NO:4. In embodiments, the antisense VCP exon 5 nucleic acid has at least 93% sequence identity to SEQ ID NO:4. In embodiments, the antisense VCP exon 5 nucleic acid has at least 94% sequence identity to SEQ ID NO:4. In embodiments, the antisense VCP exon 5 nucleic acid has at least 95% sequence identity to SEQ ID NO:4. In embodiments, the antisense VCP exon 5 nucleic acid has at least 96% sequence identity to SEQ ID NO:4. In embodiments, the antisense VCP exon 5 nucleic acid has at least 97% sequence identity to SEQ ID NO:4. In embodiments, the antisense VCP exon 5 nucleic acid has at least 98% sequence identity to SEQ ID NO:4. In embodiments, the antisense VCP exon 5 nucleic acid has at least 99% sequence identity to SEQ ID NO:4. In embodiments, the antisense VCP exon 5 nucleic acid has at least 80%, 85%, 90%, 95%, 96%, 97%, 98%, 99% or 100% sequence identity across the whole sequence of to SEQ ID NO:4. In embodiments, the antisense VCP exon 5 nucleic acid has at least 80%, 85%, 90%, 95%, 96%, 97%, 98%, 99% or 100% sequence identity across 10, 15, 20, 25, 26, 27, or 28 continuous nucleotides of SEQ ID NO:4.

In embodiments, the antisense VCP exon 5 nucleic acid has at least 80% sequence identity to SEQ ID NO:5. In embodiments, the antisense VCP exon 5 nucleic acid has at least 85% sequence identity to SEQ ID NO:5. In embodiments, the antisense VCP exon 5 nucleic acid has at least 90% sequence identity to SEQ ID NO:5. In embodiments, the antisense VCP exon 5 nucleic acid has at least 91% sequence identity to SEQ ID NO:5. In embodiments, the antisense VCP exon 5 nucleic acid has at least 92% sequence identity to SEQ ID NO:5. In embodiments, the antisense VCP exon 5 nucleic acid has at least 93% sequence identity to SEQ ID NO:5. In embodiments, the antisense VCP exon 5 nucleic acid has at least 94% sequence identity to SEQ ID NO:5. In embodiments, the antisense VCP exon 5 nucleic acid has at least 95% sequence identity to SEQ ID NO:5. In embodiments, the antisense VCP exon 5 nucleic acid has at least 96% sequence identity to SEQ ID NO:5. In embodiments, the antisense VCP exon 5 nucleic acid has at least 97% sequence identity to SEQ ID NO:5. In embodiments, the antisense VCP exon 5 nucleic acid has at least 98% sequence identity to SEQ ID NO:5. In embodiments, the antisense VCP exon 5 nucleic acid has at least 99% sequence identity to SEQ ID NO:5. In embodiments, the antisense VCP exon 5 nucleic acid has at least 80%, 85%, 90%, 95%, 96%, 97%, 98%, 99% or 100% sequence identity across the whole sequence of to SEQ ID NO:5. In embodiments, the antisense VCP exon 5 nucleic acid has at least 80%, 85%, 90%, 95%, 96%, 97%, 98%, 99% or 100% sequence identity across 10, 15, 20, 25, 26, 27, or 28 continuous nucleotides of SEQ ID NO:5.

In embodiments, the antisense VCP exon 5 nucleic acid has at least 80% sequence identity to SEQ ID NO:6. In embodiments, the antisense VCP exon 5 nucleic acid has at least 85% sequence identity to SEQ ID NO:6. In embodiments, the antisense VCP exon 5 nucleic acid has at least 90% sequence identity to SEQ ID NO:6. In embodiments, the antisense VCP exon 5 nucleic acid has at least 91% sequence identity to SEQ ID NO:6. In embodiments, the antisense VCP exon 5 nucleic acid has at least 92% sequence identity to SEQ ID NO:6. In embodiments, the antisense VCP exon 5 nucleic acid has at least 93% sequence identity to SEQ ID NO:6. In embodiments, the antisense VCP exon 5 nucleic acid has at least 94% sequence identity to SEQ ID NO:6. In embodiments, the antisense VCP exon 5 nucleic acid has at least 95% sequence identity to SEQ ID NO:6. In embodiments, the antisense VCP exon 5 nucleic acid has at least 96% sequence identity to SEQ ID NO:6. In embodiments, the antisense VCP exon 5 nucleic acid has at least 97% sequence identity to SEQ ID NO:6. In embodiments, the antisense VCP exon 5 nucleic acid has at least 98% sequence identity to SEQ ID NO:6. In embodiments, the antisense VCP exon 5 nucleic acid has at least 99% sequence identity to SEQ ID NO:6. In embodiments, the antisense VCP exon 5 nucleic acid has at least 80%, 85%, 90%, 95%, 96%, 97%, 98%, 99% or 100% sequence identity across the whole sequence of to SEQ ID NO:6. In embodiments, the antisense VCP exon 5 nucleic acid has at least 80%, 85%, 90%, 95%, 96%, 97%, 98%, 99% or 100% sequence identity across 10, 15, 20, 25, 26, 27, or 28 continuous nucleotides of SEQ ID NO:6.

In embodiments, the antisense VCP exon 5 nucleic acid has at least 80%, 85%, 90%, 95%, 96%, 97%, 98%, 99% or 100% sequence identity across 10, 15, 20, 25, 26, 27, or 28 continuous nucleotides of SEQ ID NO: 10.

In embodiments, the antisense VCP exon 4 nucleic acid or the antisense VCP exon 5 nucleic acid effects exon skipping of VCP exon 4 or VCP exon 5 in the subject, respectively. In embodiments, the antisense VCP exon 4 nucleic acid effects exon skipping of VCP exon 4 in the subject. Where the antisense VCP exon 4 nucleic acid effects exon skipping of VCP exon 4, the frequency of VCP exon 4 expression is decreased relative to the absence of the antisense VCP exon 4 nucleic acid. In embodiments, the antisense VCP exon 5 nucleic acid effects exon skipping of VCP exon 5 in the subject. Where the antisense VCP exon 5 nucleic acid effects exon skipping of VCP exon 5, the frequency of VCP exon 5 expression is decreased relative to the absence of the antisense VCP exon 5 nucleic acid.

In embodiments, the antisense VCP exon 4 nucleic acid or an antisense VCP exon 5 nucleic acid binds to an acceptor or donor splice site of VCP exon 4 or an acceptor or donor splice site of VCP exon 5 in the subject, respectively. In embodiments, the antisense VCP exon 4 nucleic acid binds to an acceptor or donor splice site of VCP exon 4 in the subject. In embodiments, the antisense VCP exon 4 nucleic acid binds to an acceptor splice site of VCP exon 4 in the subject. In embodiments, the antisense VCP exon 4 nucleic acid binds to a donor splice site of VCP exon 4 in the subject. In embodiments, the antisense VCP exon 5 nucleic acid binds to an acceptor or donor splice site of VCP exon 5 in the subject. In embodiments, the antisense VCP exon 5 nucleic acid binds to an acceptor splice site of VCP exon 5 in the subject. In embodiments, the antisense VCP exon 5 nucleic acid binds to a donor splice site of VCP exon 5 in the subject.

In embodiments, the antisense VCP exon 4 nucleic acid or the antisense VCP exon 5 nucleic acid binds to an intronic sequence flanking VCP exon 4 or an intronic sequence flanking VCP exon 5, respectively. An intronic sequence flanking VCP exon 4 is an intron sequence located adjacent to the sequence of VCP exon 4.

In embodiments, the antisense VCP exon 4 nucleic acid binds to an intronic sequence flanking VCP exon 4. In embodiments, the antisense VCP exon 5 nucleic acid binds to an intronic sequence flanking VCP exon 5. An intronic sequence flanking VCP exon 5 is an intron sequence located adjacent to the sequence of VCP exon 5.

In embodiments, the antisense VCP exon 4 nucleic acid or the antisense VCP exon 5 nucleic acid binds to a VCP exon 4 splice enhancer sequence or a VCP exon 5 splice enhancer sequence, respectively. In embodiments, the antisense VCP exon 4 nucleic acid binds to a VCP exon 4 splice enhancer sequence. In embodiments, the antisense VCP exon 5 nucleic acid binds to a VCP exon 5 splice enhancer sequence.

Further to any aspect or embodiment disclosed above, in embodiments the method includes administering an antisense VCP exon 5 nucleic acid.

In embodiments, the antisense VCP exon 5 nucleic acid binds to a VCP Exon 5A sequence. In embodiments, the VCP Exon 5A sequence is the sequence of SEQ ID NO: 1, SEQ ID NO:2, SEQ ID NO:3, SEQ ID NO:4, SEQ ID NO:5 or SEQ ID NO:6.

In embodiments, the antisense VCP exon 5 nucleic acid includes a sequence set forth in Table 1 disclosed below. In embodiments, the antisense VCP exon 5 nucleic acid includes the sequence of SEQ ID NO: 1. In embodiments, the antisense VCP exon 5 nucleic acid includes the sequence of SEQ ID NO:2. In embodiments, the antisense VCP exon 5 nucleic acid includes the sequence of SEQ ID NO:3. In embodiments, the antisense VCP exon 5 nucleic acid includes the sequence of SEQ ID NO:4. In embodiments, the antisense VCP exon 5 nucleic acid includes the sequence of SEQ ID NO:5. In embodiments, the antisense VCP exon 5 nucleic acid includes the sequence of SEQ ID NO:6. In embodiments, the antisense VCP exon 5 nucleic acid is the sequence of SEQ ID NO: 1. In embodiments, the antisense VCP exon 5 nucleic acid is the sequence of SEQ ID NO:2. In embodiments, the antisense VCP exon 5 nucleic acid is the sequence of SEQ ID NO:3. In embodiments, the antisense VCP exon 5 nucleic acid is the sequence of SEQ ID NO:4. In embodiments, the antisense VCP exon 5 nucleic acid is the sequence of SEQ ID NO:5. In embodiments, the antisense VCP exon 5 nucleic acid is the sequence of SEQ ID NO:6.

In embodiments, the subject has an R155H mutation in VCP exon 5. Where the subject has an R155H mutation in VCP exon 5, the VCP gene of the subject includes a histidine at a position corresponding to amino acid positon 155 of SEQ ID NO:7. In embodiments, the antisense VCP exon 5 nucleic acid binds to a VCP exon 5 sequence including the R155H mutation.

Further to any aspect or embodiments disclosed above, in embodiments the antisense VCP exon 4 nucleic acid and the antisense VCP exon 5 nucleic acid are modified nucleic acids. In embodiments, the antisense VCP exon 4 nucleic acid is a modified nucleic acid. In embodiments, the antisense VCP exon 5 nucleic acid is a modified nucleic acid. The term "modified nucleic acid" and the like refer, in the usual and customary sense, to nucleic acids which are chemically modified with respect to naturally occurring nucleic acids. In embodiments, the modified nucleic acids are phosphorodiamidate morpholino oligomers (PMO), peptide nucleic acids (PNA), locked nucleic acids (LNA), ethylene bridged nucleic acids (ENA) or 2'-O-methyl modified nucleic acids.

In embodiments, the modified nucleic acids are phosphorodiamidate morpholino oligomers (PMO). In embodiments, the modified nucleic acids are peptide nucleic acids (PNA). In embodiments, the modified nucleic acids are locked nucleic acids (LNA). In embodiments, the modified nucleic acids are ethylene bridged nucleic acids (ENA). In embodiments, the modified nucleic acids are 2'-O-methyl modified nucleic acids.

In embodiments, the modified nucleic acids include a phosphodiester backbone, phosphorothioate backbone, phosphorodithioate backbone or boranophosphate backbone. In embodiments, the modified nucleic acids include a phosphodiester backbone. In embodiments, the modified nucleic acids include a phosphorodithioate backbone. In embodiments, the modified nucleic acids include a boranophosphate backbone.

In embodiments, the modified nucleic acids are 2'-O-methyl modified nucleic acids including a phosphorothioate backbone.

Further to any aspect or embodiments disclosed above, in embodiments the antisense VCP exon 4 nucleic acid and the antisense VCP exon 5 nucleic acid are administered systemically as cationic lipoplexes. In embodiments, the antisense VCP exon 4 nucleic acid is administered systemically as cationic lipoplexes. In embodiments, the antisense VCP exon 5 nucleic acid is administered systemically as cationic lipoplexes.

Yet further to any aspect or embodiments disclosed above, in embodiments the VCP-associated neurodegenerative disease is Paget's disease, Frontotemporal Dementia (IBMPFD), inclusion body myopathy (IBM), limb girdle muscular dystrophy (LGMD), amyotrophic lateral sclerosis (ALS), facioscapular muscular dystrophy (FSHD), or scapuloperoneal muscular dystrophy (SPMD). In embodiments, the VCP-associated neurodegenerative disease is Paget's disease, Frontotemporal Dementia (IBMPFD), inclusion body myopathy (IBM), limb girdle muscular dystrophy (LGMD), amyotrophic lateral sclerosis (ALS), facioscapular muscular dystrophy (FSHD), or scapuloperoneal muscular dystrophy (SPMD). In embodiments, the VCP-associated neurodegenerative disease is Paget's disease. In embodiments, the VCP-associated neurodegenerative disease is Frontotemporal Dementia (IBMPFD). In embodiments, the VCP-associated neurodegenerative disease is inclusion body myopathy (IBM). In embodiments, the VCP-associated neurodegenerative disease is limb girdle muscular dystrophy (LGMD). In embodiments, the VCP-associated neurodegenerative disease is amyotrophic lateral sclerosis (ALS). In embodiments, the VCP-associated neurodegenerative disease is facioscapular muscular dystrophy (FSHD). In embodiments, the VCP-associated neurodegenerative disease is scapuloperoneal muscular dystrophy (SPMD).

III. Transgenic Mouse

In another aspect, there is provided a transgenic mouse including a drug-inducible Cre recombinase excisable VCP exon 4 or a drug-inducible Cre recombinase excisable VCP exon 5. In embodiments, the drug is a cancer drug. In embodiments, the drug is a breast cancer drug. In embodiments, the drug is tamoxifen. "Tamoxifen" as provided herein refers to the chemical compound ethanamine, 2-[4-[(1Z)-1,2-diphenyl-1-butenyl]phenoxy]-N,N-dimethyl. In a customary sense tamoxifen refers to CAS Registry No. 10540-29-1. In embodiments, the mouse includes a tamoxifen-inducible Cre recombinase excisable VCP exon 4 or a tamoxifen-inducible Cre recombinase excisable VCP exon 5.

In another aspect, there is provided a transgenic mouse including a tamoxifen-inducible Cre recombinase excisable VCP exon 4 or a tamoxifen-inducible Cre recombinase excisable VCP exon 5.

In another aspect, there is provided a transgenic mouse including a drug-inducible Cre recombinase excisable VCP exon 4. In another aspect, there is provided a transgenic mouse including a tamoxifen-inducible Cre recombinase excisable VCP exon 4. In another aspect, there is provided a transgenic mouse including a drug-inducible Cre recombinase excisable VCP exon 5. In another aspect, there is provided a transgenic mouse including a tamoxifen-inducible Cre recombinase excisable VCP exon 5. In embodiments, the transgenic mouse includes a VCP R155H mutation.

IV. Pharmaceutical Compositions

In another aspect, there is provided a pharmaceutical composition including a pharmaceutically acceptable excipient in combination with an antisense VCP exon 4 nucleic acid or an antisense VCP exon 5 nucleic acid.

1. Formulations

The compositions described herein can be prepared and administered in a wide variety of oral, parenteral, and topical dosage forms. Thus, the compounds described herein can be administered by injection (e.g., intravenously, intramuscularly, intracutaneously, subcutaneously, intraduodenally, or intraperitoneally). Also, the compounds described herein can be administered by inhalation, for example, intranasally. Additionally, the compounds described herein can be administered transdermally. It is also envisioned that multiple routes of administration (e.g., intramuscular, oral, transdermal) can be used to administer the compounds described herein. Accordingly, pharmaceutical compositions comprising a pharmaceutically acceptable carrier or excipient and one or more compounds are contemplated.

For preparing pharmaceutical compositions, pharmaceutically acceptable carriers can be either solid or liquid. Solid form preparations include powders, tablets, pills, capsules, cachets, suppositories, and dispersible granules. A solid carrier can be one or more substances that may also act as diluents, flavoring agents, binders, preservatives, tablet disintegrating agents, or an encapsulating material.

In powders, the carrier is a finely divided solid in a mixture with the finely divided active component. In tablets, the active component is mixed with the carrier having the necessary binding properties in suitable proportions and compacted in the shape and size desired.

Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compositions with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures are injectable, sterile solutions, preferably oily or aqueous solutions, as well as suspensions, emulsions, or implants, including suppositories. In particular, carriers for parenteral administration include aqueous solutions of dextrose, cyclodextrins, saline, pure water, ethanol, glycerol, propylene glycol, peanut oil, sesame oil, polyoxyethylene-block polymers, and the like. Ampoules are convenient unit dosages. The compositions described herein can also be incorporated into liposomes or administered via transdermal pumps or patches. Pharmaceutical admixtures suitable for use include those described, for example, in PHARMACEUTICAL SCIENCES (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and/or thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation can be in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. In embodiments, the pre-filled applicator can be filled with a pharmaceutical composition in the form of a cream, a gel or an ointment that contains a compound described herein.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103;

cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

2. Effective Dosages

Pharmaceutical compositions include compositions wherein the active ingredient is contained in a therapeutically effective amount, i.e., in an amount effective to achieve its intended purpose. The actual amount effective for a particular application will depend, inter alia, on the condition being treated, as judged by a practioner in the medical or verterinary arts. For example, when administered in methods to treat cancer, such compositions will contain an amount of active ingredient effective to achieve the desired result (e.g., decreasing the number of cancer cells in a subject).

The dosage and frequency (single or multiple doses) of compound administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds described herein.

Dosages may be varied depending upon the requirements of the patient and the compound being employed. The dose administered to a patient should be sufficient to effect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

3. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compositions that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g., Fingl et al., In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the compound is used.

EXAMPLES

Example 1. Targeted Excision of VCP R155H Mutation by Cre-LoxP Technology as a Promising Therapeutic Strategy for VCP Disease Inclusion Body Myopathy associated with Paget's disease of the bone and Frontotemporal Dementia, (IBMPFD, OMIM 167320) is attributed to mutations in the Valosin Containing Protein (VCP) gene, mapped to chromosomal region 9p13.3-12. Affected individuals exhibit scapular winging and die from progressive muscle weakness and cardiac and respiratory failure in their 40's to 50's. Mutations in the VCP gene have also been associated with amyotrophic lateral sclerosis (ALS) in 10-15% of individuals with hereditary inclusion body myopathy (hIBM) and 2-3% of isolated familial amyotrophic lateral sclerosis (fALS). Applicants generated the CRE-ER™-VCP$^{R155H/+}$ TAMOXIFEN™-inducible model. Applicants administered the pregnant dams with 0.12 mg/g body weight TAMOXIFEN™ or corn oil (vehicle) by oral gavage and monitored the survival and muscle strength of the pups until 18 months of age. The CRE-ER™-VCP$^{R155H/+}$ treated mice demonstrated improved muscle strength and quadriceps fiber architecture, reduced expression of autophagy markers, reduced brain neuropathology, decreased apoptosis, and improvement of the Paget-like bone changes.

Inclusion Body Myopathy (IBM) associated with Paget's disease of the bone (PDB) and Frontotemporal Dementia, (IBMPFD, OMIM 167320), was first reported in 2000 by Kimonis et al. (1) and mapped to the human chromosomal region 9p13.3-12 (2) (3). In 2004, the disease was attributed to being caused by mutations in the gene encoding Valosin-Containing Protein (VCP) (4). Classic symptoms of VCP disease include weakness and atrophy of the skeletal muscles of the pelvic and shoulder girdle muscles in 90% of individuals (1-3). Affected individuals exhibit scapular winging and die from progressive muscle weakness, and cardiac and respiratory failure, typically in their 40's to 50's (1, 5). Histologically, patients show the presence of rimmed vacuoles and TAR DNA-binding protein 43 (TDP-43)-positive large ubiquitinated inclusion bodies in the muscles (1, 4, 5, 6). The variable phenotype is often diagnosed as limb girdle muscular dystrophy (LGMD), amyotrophic lateral sclerosis (ALS), facioscapular muscular dystrophy (FSHD), or scapuloperoneal muscular dystrophy (SPMD) (5, 7, 8). To date, 31 VCP mutations have been reported in families from several parts of the world including Germany (9, 10), France (11), Austria (12), Italy (13, 14), the UK (15), Australia (16), Brazil (17), Korea (18), Japan (19) and the US (20, 21). VCP mutations have been noted in 2-3% of isolated familial amyotrophic lateral sclerosis (fALS) cases (22), and 10-15% of individuals with hereditary inclusion body myopathy have an ALS-like phenotype characterized as a progressive neurodegenerative disease involving both upper motor neurons (UMNs) and lower motor neurons (LMNs) (5).

Recently, VCP has also shown a critical role in maintaining mitochondrial quality and dynamics in the PINK1/Parkin pathway, whereby pathogenic mutations in VCP lead to an impairment in proteasome-dependent degradation (23). Other studies have demonstrated the 4 autophagic mechanism of VCP regulation and function, an important process in mediating protein degradation for terminally differentiated cells. Autophagy is responsible for degrading defective organelles and the bulk of cytoplasm during starvation. Recent studies have shown that sequestosome 1 (p62/SQSTM1) interacts with the autophagic effector protein Light Chain 3 (LC3) to mediate the autophagic uptake of aggregated proteins. VCP is important for the retrotranslocation of misfolded endoplasmic reticulum (ER) proteins, and failure in this activity results in defective endoplasmic reticulum associated protein degradation (ERAD) and ER stress responses (24). Interestingly, the SQSTM1 gene, which encodes p62/SQSTM1, is involved in autophagy, and apoptosis, and is responsible for approximately 10% of sporadic PDB and 50% of familial PDB and mutations in p62/SQSTM1 have now been associated with ALS. Autophagic degradation is also involved in Alzheimer's and Huntington's diseases, as well as in other neurodegenerative diseases (25-29).

Generation of TAMOXIFEN™-inducible Cre models has become the gold standard for determining gene function in mice by allowing the phenotypic analyses for selected tissues during embryonic development. Inducible transgenesis provides a powerful platform to analyze the functions of genes and proteins physiologically in vivo. Recent studies based on novel gene, cell and drug therapies in patients have shown promising exon skipping strategies to treat muscular dystrophies such as Duchenne muscular dystrophy (DMD), Becker muscular dystrophy (BMD) (30, 31) and in another autosomal dominant disorder fibrodysplasia ossificans progressive (FOP) by reducing the excessive activin receptor-like kinase 2 (ACVR1/ALK2) in FOP patients (32). Applicants generated a transgenic CRE-ER™-VCP$^{R155H/+}$ mouse model, with the targeted excision of the VCP R155H mutation that demonstrates amelioration of the typical phenotypic features of VCP-associated diseased patients.

The VCP$^{R155H/+}$ heterozygous mouse was created with two loxp sites, placed on either side of the R155H mutation in exons 4 and 5, allowing the possibility of deleting this region with Cre-loxP technology. In this investigation, Applicants crossed their VCP$^{R155H/+}$ mice with a mouse line containing the CRE-ER™ hybrid recombinase transgene (FIG. 1A), ubiquitously expressed in all tissues, driven by the endogenous mouse ROSA promoter, thereby generating a unique Cre-ER™-VCP$^{R155H/+}$ mouse model.

Applicants evaluated the effects of inducing Cre-mediated recombination during early postnatal development. The pregnant CRE-ER™-VCP$^{R155H/+}$ dams were oral gavaged once with TAMOXIFEN™ (0.12 mg/g body weight) at E6.75, anticipating that the TAMOXIFEN™ would be transferred to the pups though the placenta. Upon birth, the pups were monitored for weight and muscle strength measurements. Recombination was confirmed by PCR analysis. Prenatal treatment is preferred as this allows Applicants to follow the effects of mutation excision from an early age of development. Additionally, TAMOXIFEN™ treatment in young pups is lethal.

Figure 1B:
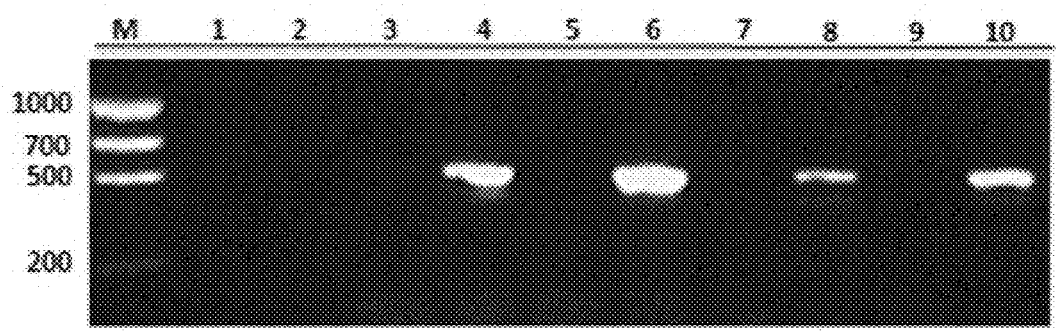
Figure 2A:
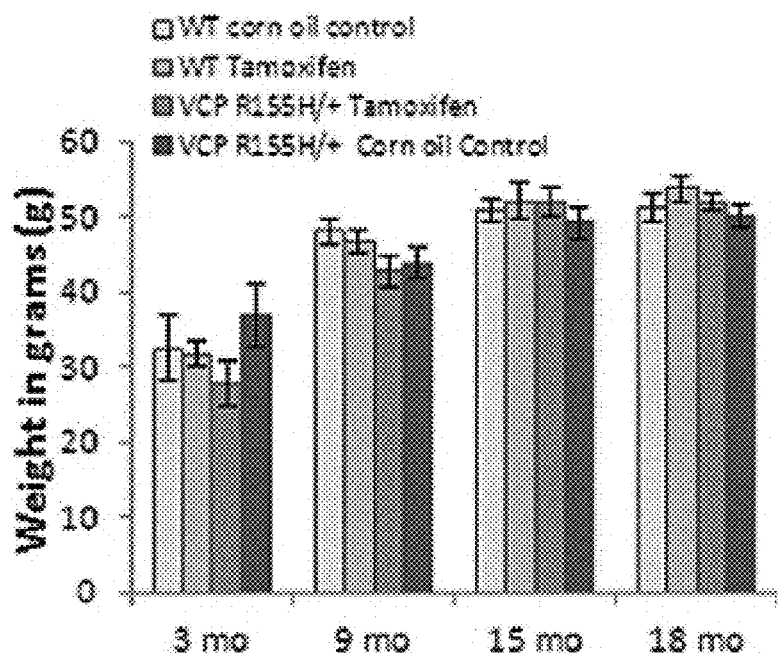
FIGS. 2A-2C. Weight, grip strength and histological analyses of Cre-mediated recombination in Cre-ER™-VCP$^{R155H/+}$ mice.
Figure 2B:
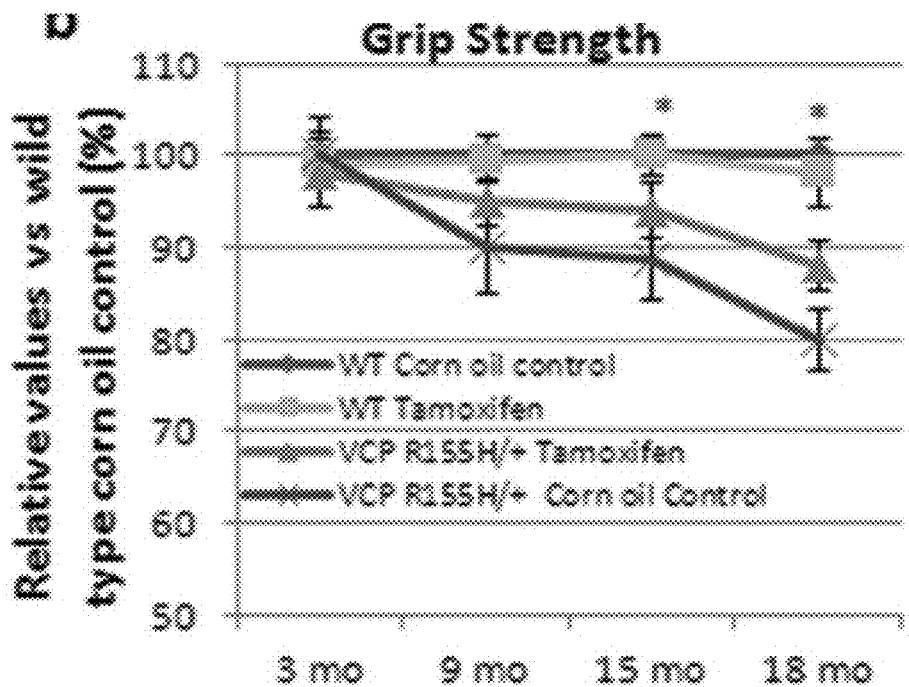

Applicants assessed the efficiency and functionality of Cre recombination in the pups of the TM-treated pregnant VCP$^{R155H/+}$ mice. The CRE-ER™ hybrid recombinase is trapped in the cellular cytoplasm and is unable to mediate recombination of the DNA region flanked by loxP sites until its activation with TAMOXIFEN™. Once TAMOXIFEN™ is administered and binds to the murine Estrogen Receptor (mER), Cre protein translocates to the nucleus to induce site specific recombination (33, 34). PCR primers flanking the loxp sites give rise to a 500 base pair PCR product when the region is deleted, confirming efficient Cre-mediated recombination of the VCP gene in the Cre-ER™-VCP$^{R155H/+}$ pups in skeletal muscle, liver, kidney, and brain samples (FIG. 1B). Muscle strength and histology in CRE-ER™-VCP$^{R155H/+}$ mice VCP$^{R155H/+}$ mice have an equal life span to wild type littermates (35, 36). Survival did not differ between the monitored TAMOXIFEN™-treated and untreated CRE-ER™-VCP$^{R155H/+}$ mice. Weight measurements at 3-, 9-, 15-, and 18-months of age in TAMOXIFEN™-treated and untreated WT and VCP$^{R155H/+}$ pups did not show any significant differences (FIG. 2A). Next, Applicants performed grip strength measurements to examine the effects of TAMOXIFEN™-induced Cre-mediated recombination on the muscle strength of CRE-ER™-VCP$^{R155H/+}$ transgenic mice. There was significant improvement in the muscle strength measurements in TAMOXIFEN™-treated CRE-ER™-VCP$^{R155H/+}$ mice when compared to their control littermates at 15- and 18-months of age (p<0.05) (FIG. 2B). Specifically, grip strength analyses in TAMOXIFEN™-treated CRE-ER™-VCP$^{R155H/+}$ mice showed a 50% improvement in muscle strength at 15 months (SD±3.1) and 40% improvement at 18 months of age (SD±2.6) compared to the control corn oil VCP$^{R155H/+}$ heterozygotes.

Figure 2C:
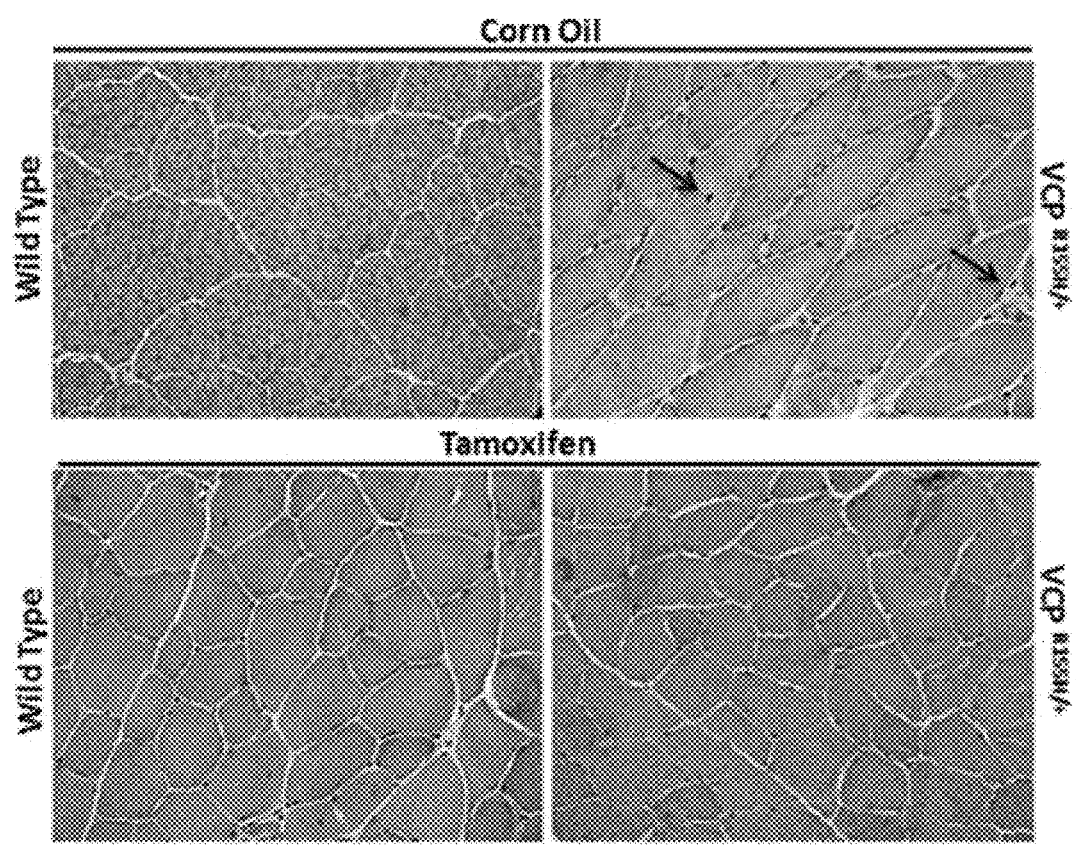

Applicants evaluated the effects of inducing Cre-mediated recombination in the quadriceps of CRE-ER™-VCP$^{R155H/+}$ mice and control littermates by histology. The changes in histology in the TAMOXIFEN™-treated CRE-ER™-VCP$^{R155H/+}$ animals included an improvement in the organization of the muscle fibers at 18-months of age (FIG. 2C), reduced centrally localized nuclei, decreased endomysial space, and a decrease in neurodegenerative fibers.

Figure 3A:
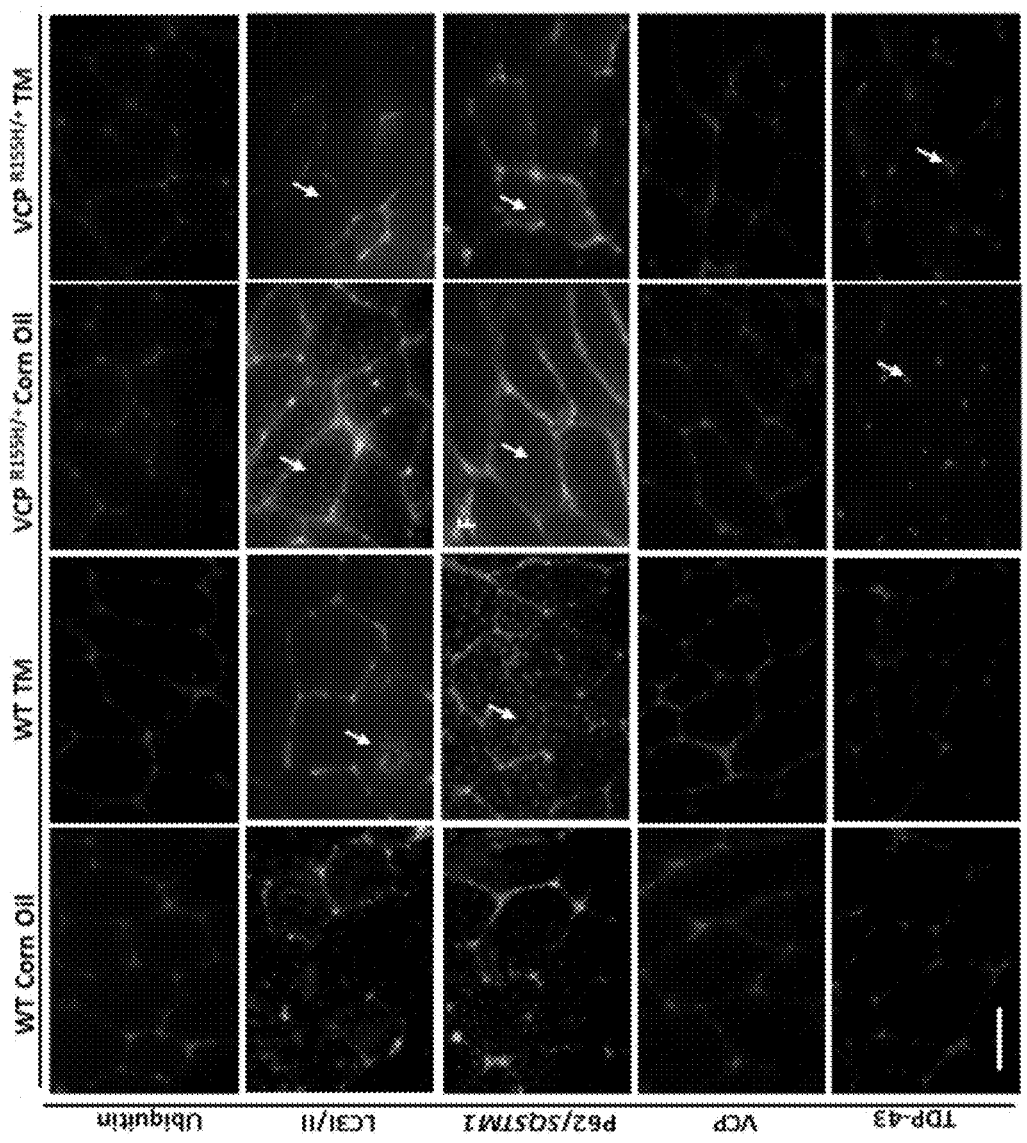
FIGS. 3A-3C. Analysis of autophagy cascade in the quadriceps of CRE-ER™-VCP$^{R155H/+}$ mice.
Figure 3B:
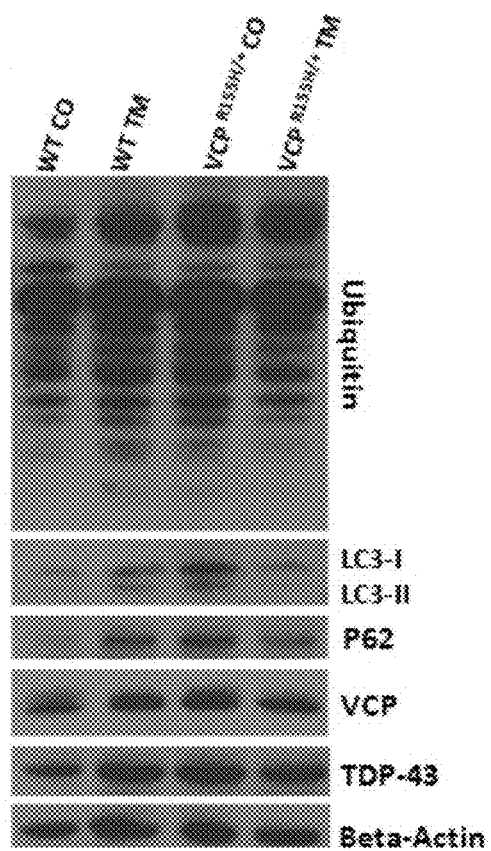
Figure 3C:
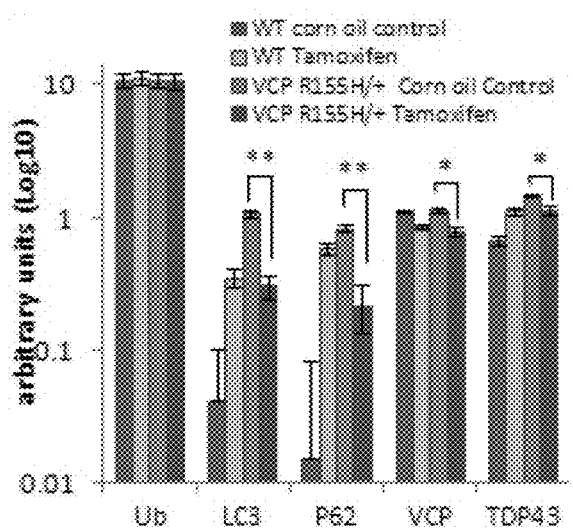

CRE-ER™-VCP$^{R155H/+}$ mice exhibit improvement of the autophagic cascade in quadriceps. The autophagy cascade whereby long-lived proteins are degraded is of critical importance in understanding one of the possible underlying mechanisms in VCP disease. Applicants have previously shown that the autophagy pathway is disrupted in patients myoblasts and our VCP$^{R155H/+}$ mouse model (35-37). To determine whether autophagic processes were altered in the quadriceps muscles in the CRE-ER™-VCP$^{R155H/+}$ and WT mice, Applicants analyzed levels of autophagy markers including ubiquitin, VCP, LC3-I/II, and p62/SQSTM1 by immunohistochemistry (FIG. 3A) and Western blotting (FIGS. 3B and 3C). CRE-ER™-VCP$^{R155H/+}$ TAMOXIFEN™-treated mice revealed decreased protein expression levels of the autophagic markers LC3-I/II, and P62/SQSTM1, thereby suggesting correction of the autophagic cascade, compared to corn oil (vehicle)-treated control CRE-ER™-VCP$^{R155H/+}$ mice (FIGS. 3A-3C). However, ubiquitin was not significantly changed. TAMOXIFEN™ has been shown to be an autophagy and apoptosis inducer (38), and thus levels of LC3-I/II and p62/SQSTM1 autophagy markers were marginally increased in WT mice treated with TAMOXIFEN™ (FIG. 3B).

Figure 4B:
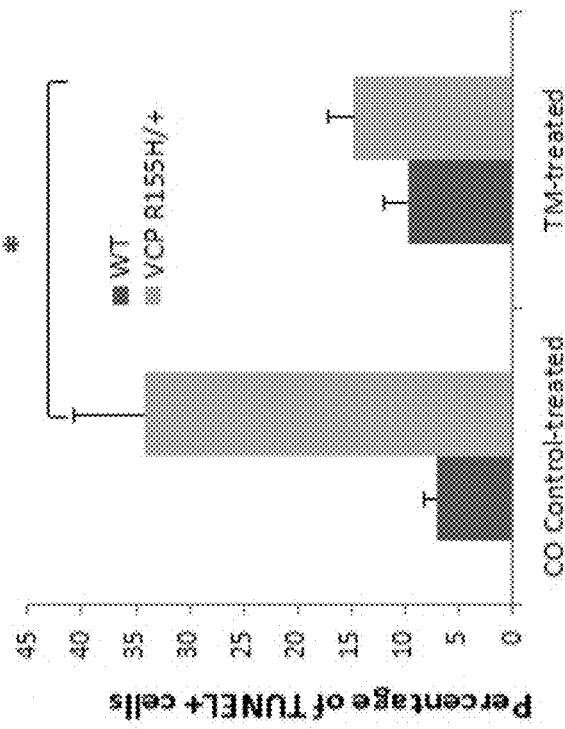
FIGS. 4A-4D. TUNEL analyses of quadriceps of Cre-mediated recombination in CRE-ER™-VCP$^{R155H/+}$ mice.
Figure 4A:
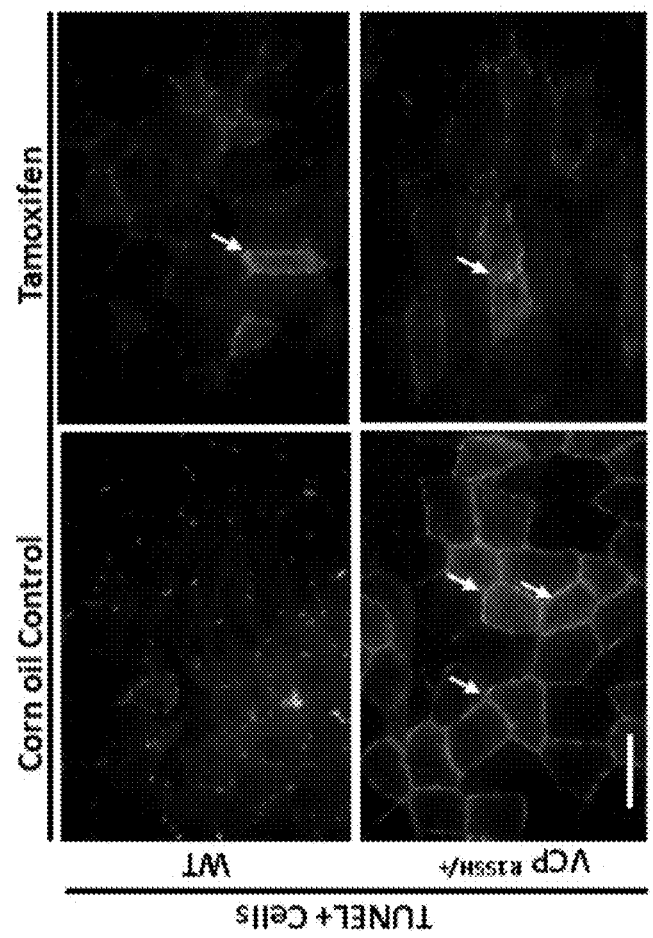
Figure 4C:
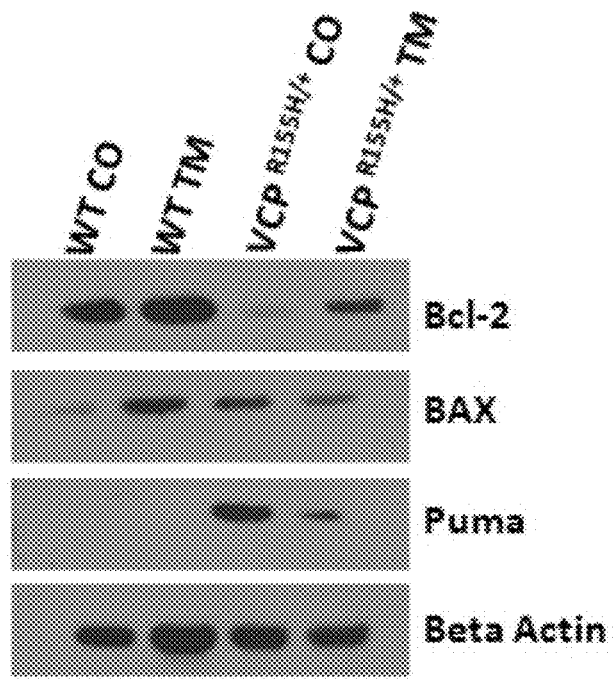
Figure 4D:
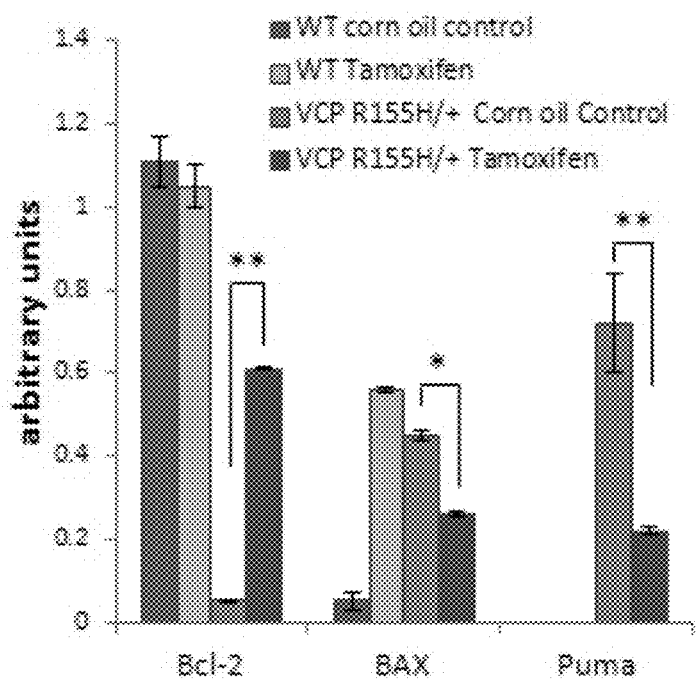

Mutations in the VCP gene have been shown to trigger cell death with apoptosis. TUNEL analysis of the quadriceps muscles from the TAMOXIFEN™-treated Cre-ER™-VCP$^{R155H/+}$ depicted a significant decrease in TUNEL+ cells, suggesting significant differences in apoptotic levels as compared to the corn oil (vehicle) control Cre-ER™-VCP$^{R155H/+}$ mice (FIGS. 4A and 4B). To further explore the apoptotic cascade, Applicants analyzed three anti- and pro-apoptotic markers, namely Bcl-2, BAX, and PUMA. There was an increased expression in pro-apoptotic protein Bcl-2 between the TAMOXIFEN™-treated Cre-ER™-VCP$^{R155H/+}$ mice versus corn oil (vehicle)-treated Cre-ER™-VCP$^{R155H/+}$ mice (FIG. 4C). There was decreased expression of Bcl-2-associated X protein, BAX and PUMA in the TM-treated Cre-ER™-VCP$^{R155H/+}$ mice versus the corn oil (vehicle) mice (FIG. 4C). The western blots analyzed by densitometry confirmed these results (FIG. 4D). Additionally, in TAMOXIFEN™-treated Cre-ER™-VCP$^{R155H/+}$ animals, protein levels of autophagy modifiers, LC3III and p62/SQSTM1 and apoptosis inducers Bcl-2-associated X protein (BAX) and p53 upregulated modulator of apoptosis (PUMA) depicted decreased levels and increased Bcl-2 expression when compared to corn oil control (vehicle)-treated Cre-ER™-VCP$^{R155H/+}$ mice.

Figure 5I:
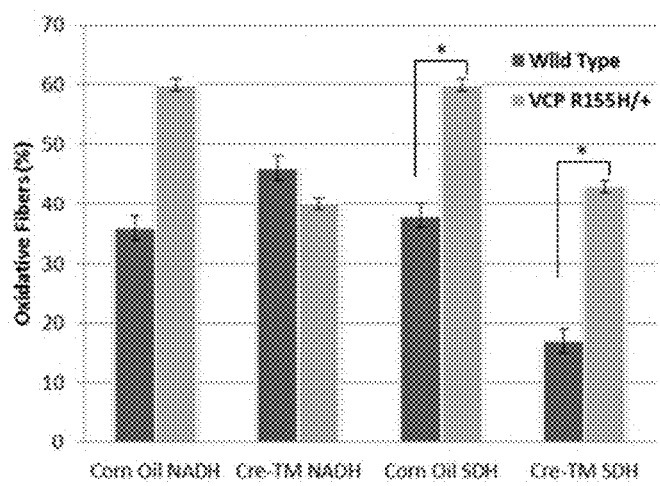
Figures 6A, 6B:
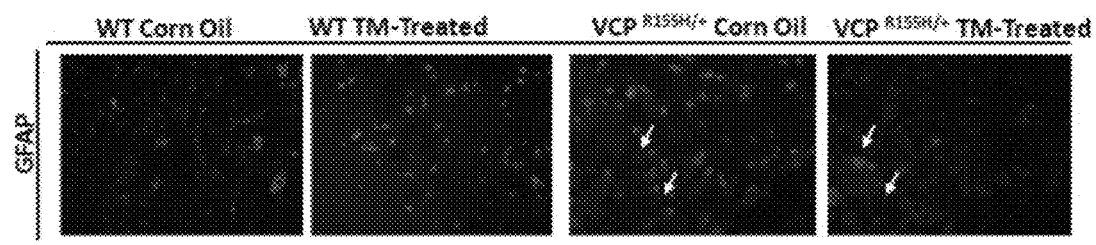
Figures 6C, 6D:
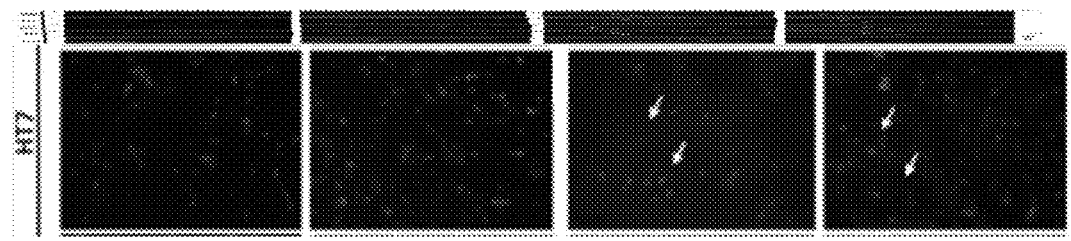
Figure 6L:
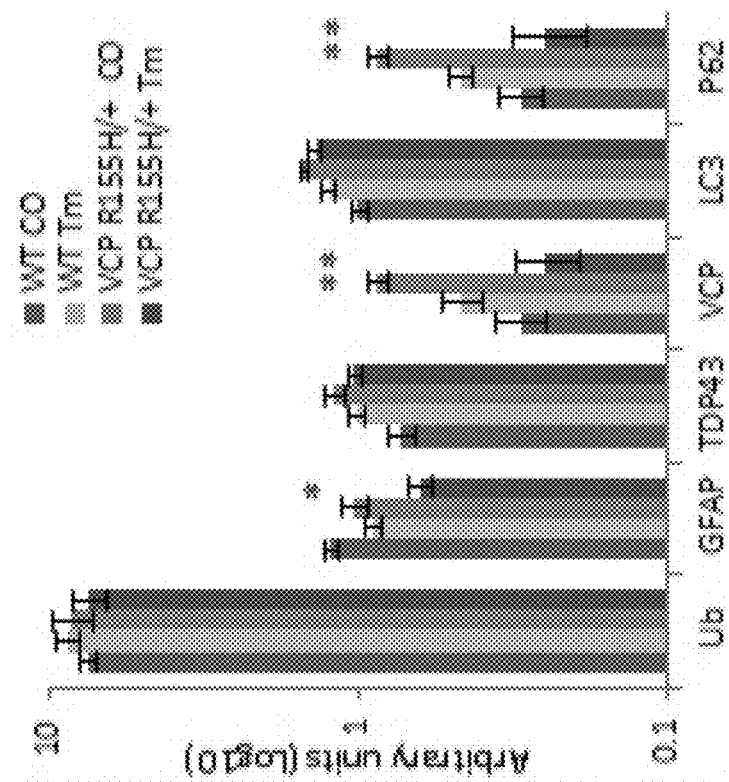
Figure 6K:
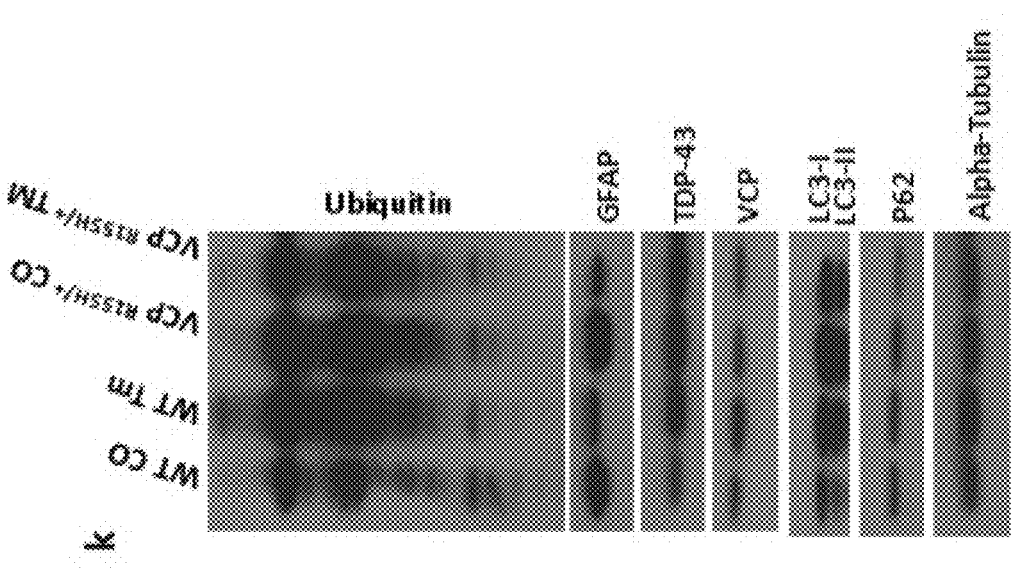

To analyze the effects of TAMOXIFEN™-induced Cre recombinase activity on the mitochondrial complexes of Cre-ER™-VCP$^{R155H/+}$ and WT animals, Applicants performed mitochondrial enzyme assays using succinic dehydrogenase (SDH) and nicotinamide adenine dinucleotide (NADH) stains. Identification of oxidative and non-oxidative fibers by SDH staining is used in assessing mitochondrial pathology where increased mitochondrial proliferation is indicative of mitochondrial dysfunction, as mitochondrial-rich type I fibers stain darker than anaerobic type II fibers. Cre-ER™-VCP$^{R155H/+}$ 18-month old animals treated with corn oil showed dark stained angular-shaped atrophic Type I fibers compared to TAMOXIFEN™ treated WT littermates which depicted a normal "checkered" pattern with NADH and SDH staining (FIGS. 5A-5H). In contrast, TAMOXIFEN™-treated Cre-ER™-VCP$^{R155H/+}$ animals demonstrated a decrease in Type I fibers, suggestive of a reduction in mitochondrial pathology (FIGS. 5D and 5H). Quantification of NADH and SDH oxidative fibers in control and TAMOXIFEN™-treated WT and Cre-ER™-VCP$^{R155H/+}$ animals confirmed these findings (p<0.05) (FIG. 5I).

Applicants evaluated the autophagy cascade in the brain samples from TAMOXIFEN™-treated and control corn oil (vehicle) WT and VCP$^{R155H/+}$ heterozygote mice by immunohistochemistry and Western blotting. Glial Fibrillary Acidic Protein (GFAP) (FIGS. 6A-6B and FIG. 6K), a marker of astrocyte proliferation and HT7 (tau) (FIGS. 6C-D and FIG. 6K), a marker of neurodegeneration protein expression levels were decreased in the TAMOXIFEN™-treated Cre-ER™-VCP$^{R155/+}$ brains compared to their littermates. The Cre-ER™-VCP$^{R155H/+}$ TAMOXIFEN™-treated mouse brains depicted decreased protein expression levels of VCP, p62/SQSTM1, LC3-I/II and TDP-43 compared to Cre Cre-ER™-VCP$^{R155H/+}$ corn oil-treated mice. Indeed, the expression levels of LC3-I/II and TDP-43 in the TAMOXIFEN™-treated Cre-ER™-VCP$^{R155H/+}$ heterozygote approached that of the control corn oil WT mice (FIG. 6A-6K). Ubiquitin levels in the brain remained comparable between treated and untreated Cre-ER™-VCP$^{R155H/+}$ mice.

Figure 7A:
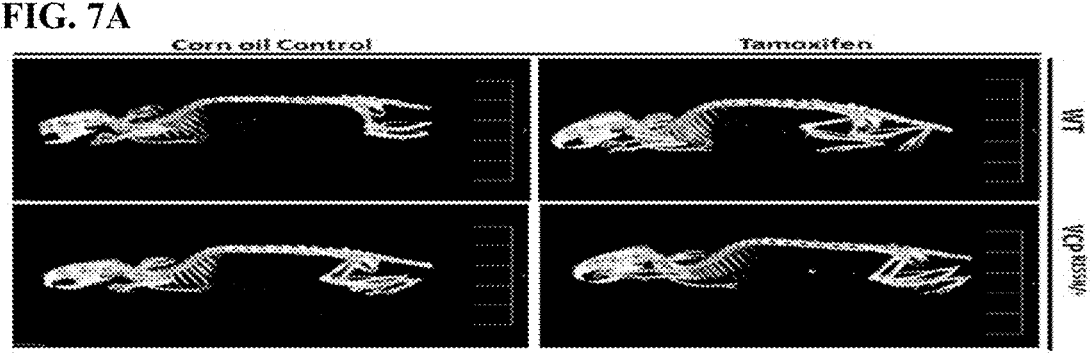
FIGS. 7A-7D. MicroCT analysis of hind limb bones in CRE-ER™-VCP$^{R155H/+}$ mice. Gross microCT images (FIGS. 7A-7B) and (FIGS. 7C-7D) hind limb bones in WT and CRE-ER™-VCP$^{R155H/+}$ mice. The number of animals used was n=5group. Arrow in FIG. 7D showing Paget like lytic lesion in VCP$^{R155H/+}$ control mouse on the left. Image on the right in the TAMOXIFEN™-treated VCP$^{R155H/+}$ mouse showing no lesion.
Figure 7B:
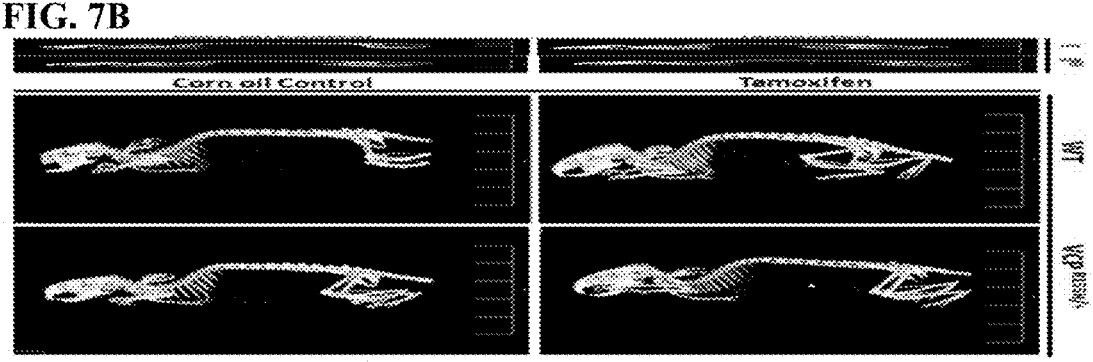
Figure 7C:
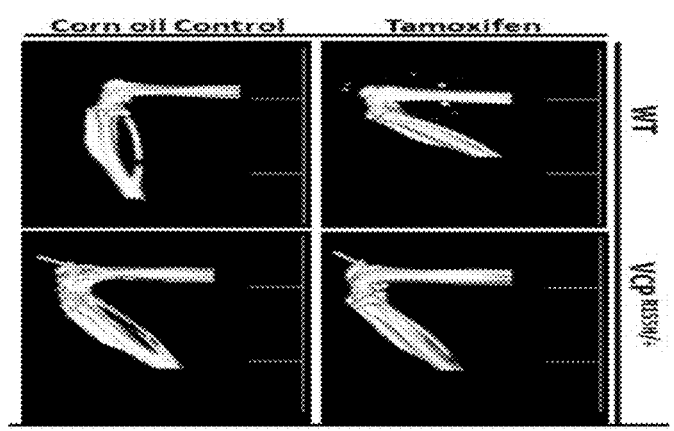
Figure 7D:
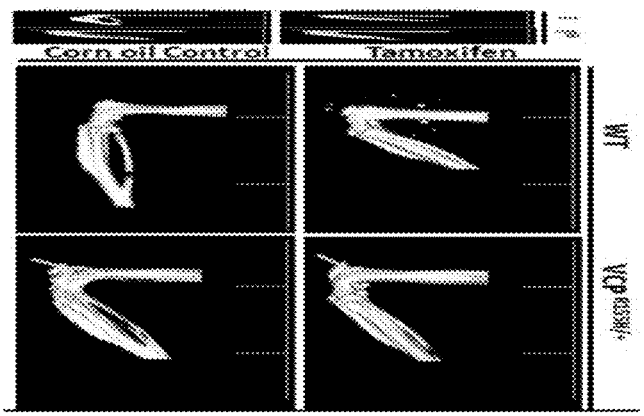

Applicants characterized the bone pathology in the TAMOXIFEN™-treated and corn oil control Cre-ER™-VCP$^{R155H/+}$ and WT mice at 18-months of age by microtomography (microCT) imaging and histology. Gross microCT images showed no significant skeletal differences in the corn oil control or TAMOXIFEN™-treated Cre-ER™-VCP$^{R155/+}$ mice (FIGS. 7A and 7B) however, close inspection of the hind limb bones in the TAMOXIFEN™-treated Cre-ER™-VCP$^{R155H/+}$ mice at 18-months of age demonstrated reduced formation of PDB-like lytic lesions (FIGS. 7C and 7D). Of the five animals analyzed, four out of five corn oil treated CRE-ER™-VCP$^{R155H/+}$ mice had PDB-like lytic lesions and one out of five TAMOXIFEN™-treated CRE-ER™-VCP$^{R155H/+}$ mice showed lytic lesions, suggesting amelioration of the PDB-like phenotype in these mice.

Specific disease mechanisms and novel therapeutic advancements underlying VCP-associated myopathies and neurodegenerative disorders remain elusive and are under further investigation. Evolutionally, VCP is highly conserved and plays a significant role in several cellular processes in both unicellular and multicellular organisms. The knock-in VCP$^{R155H/+}$ mouse model exhibits progressive muscle weakness, and histological changes including inclusions and vacuoles in the muscle fibers, Paget-like bone changes and brain and spinal cord pathology of the human VCP disease, thereby providing a useful experimental platform to further investigate the mechanisms responsible for these VCP-associated disorders. Generation of conditional TAMOXIFEN™-inducible Cre-loxP mouse models have been utilized in a number of neuromuscular and degenerative diseases including inducible androgen receptor knock-out models, spinal muscular atrophy (SMA), muscular dystrophies including Duchenne muscular dystrophy (DMD), Alzheimer's disease (AD), and amyotropic lateral sclerosis (ALS) (39). Recently, exon skipping as a therapeutic platform has demonstrated successful treatment in DMD mice and patients (40-42). Here, Applicants describe their novel TAMOXIFEN™-inducible Cre-ER™-VCP$^{R155H/+}$ mouse model and show that targeted excision of the R155H mutation in exons 4 and 5 ameliorates the phenotype observed in VCP-associated disease.

In particular, when compared to the control corn oil (vehicle) Cre-ER™-VCP$^{R155H/+}$ mice, Applicants discovered a significant improvement in muscle strength measurements by grip strength assays and partial amelioration of the typical pathology of VCP-associated disease. Impaired autophagy has been observed in several human diseases including myopathies and lysosomal storage disorders. Autophagy is a highly conserved mechanism, which is necessary for the maintenance of cellular homeostasis and orchestration of stress responses upregulated by oxidative stress, starvation or other harmful conditions. Applicants found that TAMOXIFEN™-treated Cre-ER™-VCP$^{R155H/+}$ animals had an improvement in the autophagy cascade by the decrease observed in the p62/SQSTM1, LC3I/II, ubiquitin, and TDP-43 expression levels, a decrease in apoptotic cells and a decrease in the mitochondrial enzymes NADH and SDH in Type I fibers, demonstrating a reduction in mitochondrial myopathy.

Frontotemporal dementia primarily affects the frontal and anterior temporal lobes of the brain with abnormalities of behavior and personality and language impairments variants. Applicants observed decreased accumulation of TDP-43-, ubiquitin-, HT7-(tau), and GFAP-positive inclusions in the brains of 18-month old CRE-ER™-VCP$^{R155H/+}$ TAMOXIFEN™-treated versus corn oil control mice. Also the TDP-43-positive inclusions in the control corn oil (vehicle) CRE-ER™-VCP$^{R155H/+}$ mice were cytoplasmic, in contrast to the nuclear localization in the cortex and hippocampus of TAMOXIFEN™-treated CRE-ER™-VCP$^{R155H/+}$ mice.

Paget disease of bone is usually characterized by osteoclastic lesions, abnormal bone remodeling, bone deformities, and pathologic fractures. The osteoclastic activity leads to resorption of bone and shortly thereafter by hyperactivity of the osteoblasts, leading to a disordered deposition of new bone resulting in Pagetic lesions. The lesions become sclerotic in the later stages of PDB and bone marrow is replaced with fibrous tissue and increased bone thickness. Studies have shown that 10% patients with sporadic PDB and 50% familial PDB have gene mutations of Sequestosome 1 (SQSTM1). Studies have shown that P62/SQSTM1 plays an important role in the autophagic cascade and knockout mouse models have demonstrated focal osteolytic lesions on the hind limbs. Close inspection of the long hind limb bones by microCT reveals lucencies of the proximal tibias of 18-months old corn oil-Cre-ER™-VCP$^{R155H/+}$ suggestive of PDB. Applicants' studies suggest that the Cre-loxP technology excision of the R155H mutation from the VCP gene results in a partial amelioration of PDB-like changes.

This is the first report of the CRE-ER™-VCPR$^{155H/+}$ mice using the ROSA version of the recombinase of the human estrogen receptor and crossing it with the VCP$^{R155H/+}$ mice to generate a novel excised R155H DNA segment flanked by loxP sites. TAMOXIFEN™-treated CRE-ER™-VCP$^{R155H/+}$ mice show improvements in the typical pathology observed in the heterozygote mice carrying the R155H mutation. Although exon skipping has been used successfully in X-linked disorders such as Duchenne muscular dystrophy to produce a smaller functional protein, it has only rarely been utilized in autosomal dominant disorders by knockdown of the disease allele as reported in fibrodysplasia ossificans progressiva (FOP) (32, 40, 42, 43). Thus, the CRE-ER™-VCP$^{R155H/+}$ mouse serves as a valuable model for novel therapeutic strategies such as allele silencing for the human VCP-disease and other neurodegenerative genetic disorders.

All experiments were done with the approval of the Institutional Animal Care and Use Committee (IACUC) of the University of California, Irvine (UCI) (Protocol #2007-2716-2), and in accordance with the guidelines established by the National Institutes of Health (NIH). Animals were housed in the animal facility and were maintained under constant temperature (22° C.) and humidity with a controlled 12:12-hour light-dark cycle. Animals were observed throughout the entire experimental process in order to ameliorate any pain and suffering. Mice were euthanized by $CO_2$ inhalation followed by cervical dislocation.

In order to generate a VCP disease mouse model, genomic VCP fragments with 7.9 kb of upstream homology sequence and 2.1 kb of downstream homology sequence were subcloned into a targeting vector. Site-directed mutagenesis using the Quick-Change XL Site-Directed Mutagenesis Kit (Stratagene, La Jolla, Calif.) was used to introduce the R to H mutation at amino acid position 155. The knock-in mouse model with the R155H VCP mutation was generated at InGenious Targeting Laboratory, Inc. (Ronkonkoma, N.Y.) through a neomycin cassette insertion using 129/SvEv mice. The expression of mutant VCP was confirmed by RT-PCR using the following primers in the PCR reactions: Forward-5'-CACGGTGTTGCTAAAAGGAAAGAAAAG; Reverse-3'-CTGAAGAATCTCCAAACGTCCTGTAGC, after the RT reactions with the reverse primer. These mice were backcrossed more than 10 times with the C57BL/6 strain before experiments were done to make sure that the majority (>98%) of the genetic background of generated mice was of C57BL/6 origin. The neomycin cassette was deleted by crossing with the Flp deletion mouse model. Male R26Cre-ER transgenic mice (Jackson Laboratories, Bar Harbor, Me. Strain #004847) were kindly obtained as a kind gift from Edward Monuki (University of California-Irvine, Irvine, Calif.) and crossed to females carrying the VCP gene mutation R155H. These R26CreER mutant mice have a TAMOXIFEN™-inducible Cre-mediated recombination system driven by the endogenous mouse ROSA promoter. When crossed with a strain containing a loxP site flanked sequence of interest, this mutant is useful for generating TAMOXIFEN™-induced, Cre-mediated targeted deletions. The expression of Cre was confirmed by RT-PCR using the following primers in the PCR reactions: Forward-Cre 5'-GCACTGATTTCGACCAGGTT; Reverse-Cre 3'-GCTAACCAGCGTTTTCGTTC, after the RT reactions with the reverse primer (Transnetyx Inc., Cordova, Tenn.) and results were analyzed by our laboratory. Age-matched and sex-matched littermates (n=8-10) were used in every experiment.

To promote the induction of Cre activity with TAMOXIFEN™, TAMOXIFEN™ (T5648, Sigma, St. Louis, Mo.) was dissolved in 5 ml of corn oil (Sigma) in a scintillation vial at 42° C. for 30 minutes. TAMOXIFEN™ administration induces Cre recombination in the developing embryos of treated mouse dams hence, pregnant Cre-ER™-VCP$^{R155H/+}$ females were treated with TAMOXIFEN™ at 0.12 mg/g body weight or corn oil control by oral gavage (22-gauge feeding needle) at E6.75 once. Pups were monitored on a weekly basis and weight and grip strength measurements were recorded as described previously (35).

Cre-Recombinase activity was confirmed by harvesting quadriceps, liver, kidney, and brain samples from the WT and Cre-ER™-VCP$^{R155H/+}$ mice to assess recombination following TAMOXIFEN™ administration by Polymerase Chain Reaction (PCR). Cre-mediated recombination was determined by PCR using the primers flanking the loxP sites: Forward: 5'-AGTTAGGTATGAGGCTTCCAG and Reverse: 5'-TGATTGGCACTGAGTGTGGT. The PCR conditions were as follows: Step 1: 95° for 2 min; Step 2: 95° for 30 seconds; Step 3: 55° for 30 seconds; Step 4: 72° for 1 min; then repeat Step 2-4 for 35 cycles and finally keep at 72° for 5 min.

Histological analysis was conducted on quadriceps muscles that were flash frozen in isopentane cooled in liquid nitrogen, and brains from 18-month old Cre-ER™-VCP$^{R155H/+}$ mice that were harvested and embedded in OCT compound cryo-sectioning mounting media (Electron Microscopy Sciences, Hatfield, Pa.) and stored at −80° C. before sectioning 10 m sections. For brain and spinal cord harvesting, Cre-ER™-VCP$^{R155H/+}$ mice were perfused with 4% paraformaldehyde (PFA) and sequentially transferred through several sucrose gradients, embedded, and sectioned. For immunohistochemical analyses, quadriceps and/or brain sections were incubated with anti-TDP-43, Ubiquitin, GFAP, HT7 (tau), VCP, p62/SQSTM1 and LC3-I/II-specific antibodies overnight in a humidified chamber. All antibodies were purchased from Abcam (Cambridge, Mass.). Subsequently, sections were washed with TBST (0.5%) and incubated with fluorescein-conjugated secondary antibodies (Sigma-Aldrich, St. Louis, Mo.) for 1 hour at room temperature and mounted with DAPI-containing mounting media (Vector Laboratories, Inc., Burlingame, Calif.). Sections were analyzed by fluorescence microscopy using an AxioVision image capture system (Carl Zeiss, Thornwood, N.Y.). The number of animals used in each group was n=8-10/group.

For protein expression studies, quadriceps muscle samples from 18-month old TAMOXIFEN™-treated or corn oil (vehicle)-treated WT and Cre-ER™-VCP$^{R155H/+}$ mice were harvested and extracted using the NE-PER Nuclear and Cytoplasmic Extraction Kit (Thermo Scientific, Rockford, Ill.). Protein concentrations were determined using the Nanodrop according to the manufacturer's protocols. Equal amount of proteins were separated on Bis-Tris 4-12% NuPAGE gels using the Novex Mini Cell (Invitrogen Life Technologies, Carlsbad, Calif.) according to manufacturer's protocols. The expression levels of proteins were analyzed by Western blotting using TDP-43, P62/SQSTM1, LC3-I/II, ubiquitin, GFAP, BAX, Bcl-2, and PUMA-specific antibodies. Equal protein loading was confirmed by β actin antibody (Santa Cruz Biotechnology, Santa Cruz, Calif.) staining. These experiments are representative of triplicates. Densitometry was performed to quantitate the Western blot bands using Image J Program (National Institutes of Health, Bethesda, Md.).

To assess oxidative mitochondrial markers, histochemical analyses and activity levels with succinic dehydrogenase (SDH) (Sigma-Aldrich) and nicotinamide adenine dinucleotide (NADH) (Sigma-Aldrich) were performed on quadriceps muscles from the Cre-ER™-VCP$^{R155H/+}$ and WT mice. Quadriceps cross-sections were incubated with SDH or NADH for 2 hours in the incubator at 37° C. Following incubation, slides were cooled off for 5 minutes at room temperature and mounted with Aquamount (Thermo Scientific). The staining intensity was evaluated using light microscopy.

To measure apoptosis after 24 hours, TUNEL assay (Promega, Madison, Wis.) was performed per manufacturer's instructions. Briefly, slides were fixed in 4% paraformaldehyde for 15 minutes, washed in PBS for 5 minutes and permeabilized with 20 µg/ml Proteinase K solution for 10 minutes at room temperature. Cells were then washed in PBS for 5 minutes and 100 µl of equilibration buffer was added for 10 minutes. The cells were labeled with 50 µl of TdT reaction mix and incubated for 60 minutes at 37° C. in a humidified chamber. Stop reaction was added for 15 minutes after which the cells were washed, counterstained, and prepared for analysis. The percentage of TUNEL positive cells was calculated by counting all cells per slide. These experiments are representative of triplicates.

MicroCT scans were performed by scanning the WT and Cre-ER™-VCP$^{R155H/+}$ mice with a large area CT camera. The reconstructed microCT images were analyzed and trabecular structural parameters were determined using the Inveon Multi-modality 3D Visualization software.

Means were used as summary statistics for all experiments. Applicants compared the above studies-including muscle grip strength measurements, immunohistological, TUNEL studies, and densitometries-among TAMOXIFEN™- and corn oil control (vehicle)-treated WT and Cre-ER™-VCP$^{R155H/+}$ mice using mixed model analysis of variance and pair-wise t-tests.

The number of animals used in each group was n=8-10.

Example 2. Exon Skipping Therapeutics in VCP Disease

Inclusion Body Myopathy (IBM) associated with Paget's disease of the bone (PDB) and Frontotemporal Dementia, (IBMPFD, OMIM 167320), was first reported in 2000 by Kimonis et al. [1] and mapped to the human chromosomal region 9p13.3-12 [2],[3]. In 2004, the disease was attributed to being caused by mutations in the gene encoding Valosin-Containing Protein (VCP) [4]. Classic symptoms of VCP disease include weakness and atrophy of the pelvic and shoulder girdle muscles in 90% of individuals [1-3]. Affected individuals exhibit scapular winging and die from progressive muscle weakness, and cardiac and respiratory failure, typically in their 40s to 50s [1, 5]. Histologically, patients show the presence of rimmed vacuoles and TAR DNA-binding protein 43 (TDP-43)-positive ubiquitinated inclusion bodies in the muscles [1, 4, 5, 6]. The variable phenotype is often diagnosed as limb girdle muscular dystrophy (LGMD), amyotrophic lateral sclerosis (ALS), facioscapular muscular dystrophy (FSHD), or scapuloperoneal muscular dystrophy (SPMD) [5, 7, 8]. To date, 31 VCP mutations have been reported in families from several parts of the world including Germany [9, 10], France [11], Austria [12], Italy [13, 14], the UK [15], Australia [16], Brazil [17], Korea [18], Japan [19] and the US [20, 21]. VCP mutations have been noted in 2-3% of isolated familial amyotrophic lateral sclerosis (fALS) cases [22], and 10-15% of individuals with hereditary inclusion body myopathy have an ALS-like phenotype characterized as a progressive neurodegenerative disease involving both upper motor neurons (UMNs) and lower motor neurons (LMNs)[5]. In order to understand the cellular and molecular pathophysiological mechanism(s) underlying VCP-associated neurodegenerative diseases, Applicants generated a unique Cre-ER™-VCP$^{R155H/+}$ TAMOXIFEN™-inducible mouse model. This technology allows determination of the effects of targeted excision of exons 4 and 5, including the R155H mutation, in VCP disease. Applicants administered pregnant dams with 0.12 mg/g body weight TAMOXIFEN™ or corn oil by oral gavage and monitored their survival and muscle strength of the pups until 18 months of age. The TAMOXIFEN™-treated Cre-ER™-VCP$^{R155H/+}$ mice demonstrated improved muscle strength and quadriceps muscles fiber architecture, reduced expression of autophagy markers, reduced brain neuropathology, decreased apoptosis, and partially rescued Paget's disease of bone. Parallel studies using splice switching therapeutics, which exclude or promote retention of specific exons as necessary, have been used successfully in muscle degenerative diseases such as Duchenne muscular dystrophy (DMD-exon skipping) and spinal muscular atrophy (SMA-exon retention). Applicants will develop, optimize and characterize exon skipping oligonucleotide therapeutics in VCP disease patient myoblasts in vitro, and subsequently successful oligonucleotides will be tested in the VCP$^{R155H/+}$ heterozygote mouse model.

Recently, VCP has also shown to play a critical role in maintaining mitochondrial quality and dynamics in the PINK1/Parkin pathway, whereby pathogenic mutations in VCP lead to an impairment in proteasome-dependent degradation [23]. Other studies have demonstrated the autophagic mechanism of VCP regulation and function, an important process in mediating protein degradation for terminally differentiated cells. Autophagy is responsible for degrading defective organelles and the bulk of cytoplasm during starvation. Recent studies have shown that sequestosome 1 (p62/SQSTM1) interacts with the autophagic effector protein Light Chain 3 (LC3B-I/II) to mediate the autophagic uptake of aggregated proteins. VCP is important for the retro-translocation of misfolded endoplasmic reticulum (ER) proteins, and failure in this activity results in defective endoplasmic reticulum associated protein degradation (ERAD) and ER stress responses [24]. Interestingly, the SQSTM1 gene, which encodes p62/SQSTM1, is involved in autophagy, and apoptosis, and is responsible for approximately 10% of sporadic PDB and 50% of familial PDB and mutations in p62/SQSTM1 have now been associated with ALS. Autophagic degradation is also involved in Alzheimer's and Huntington's diseases, among other neurodegenerative diseases [25-29].

Generation of TAMOXIFEN™-inducible Cre models has become the gold standard for determining gene function in mice by allowing the phenotypic analyses for selected tissues during embryonic development, thus, providing a powerful platform to analyze the functions of genes and proteins physiologically in vivo. Recent studies based on novel gene, cell and drug therapies in patients have shown promising exon skipping strategies to treat muscular dystrophies such as Duchenne muscular dystrophy (DMD), Becker muscular dystrophy (BMD) [30, 31], and in another autosomal dominant disorder fibrodysplasia ossificans progressive (FOP) by reducing the excessive activin receptor-like kinase 2 (ACVR1/ALK2) in FOP patients [32]. Applicants generated a transgenic Cre-ER™-VCP$^{R155H/+}$ mouse model, with the targeted excision of the VCP R155H mutation that demonstrates amelioration of the typical phenotypic features observed in VCP-associated diseased patients.

Some of the most promising experimental approaches to treat muscular dystrophies such as Duchenne muscular dystrophy (DMD) are based on exon skipping strategies that convert the DMD gene processing to make the milder Becker muscular dystrophy (BMD)-like dystrophin gene transcript [2-4]. DMD mutations disrupt the open reading frame and result in premature termination of translation. The truncated polypeptide is unstable and cannot form the stabilizing link between the actin cytoskeleton and the dystroglycan complex in the sarcolemma. This leads to major destabilization of the sarcolemma and weakness of muscle fibers that undergo constant damage due to stress forces generated by the working muscle [29]. The consequential loss of functional dystrophin results in muscle fibers with compromised, "leaky" membranes that disintegrate more rapidly than they can regenerate. This is in contrast to Becker muscular dystrophy (BMD), a milder form of the disease in which deletions preserve the reading frame. The resulting internally-truncated dystrophin is still expressed and partially functional, allowing BMD patients to retain some muscle function [30-32]. In consequence, BMD is milder and the average lifespan of the patient is longer, in some cases close to normal.

Pharmacological and gene therapies include exon skipping drugs such as synthetic nucleic acid analogues called antisense oligonucleotides (AONs). Studies using cell penetrating peptide conjugated PMO-targeting dystrophin exon 23 in the dko (utrophin:dystrophin deficient) mouse which typically dies 12-14 weeks after birth show a rescued phenotype, improved histopathology, and an overall normal appearance at 1 year of age [33]. Previous studies using 2'-O-methyl-phosphorothioates (2'O-MPs) antisense oligonucleotides, which were designed to excise several human DMD exons, were successful in DMD patient-derived myotubes [31]. A phase I/II clinical trial has shown that this AON is reasonably tolerated in DMD patients and thus, a phase III study was initiated to explore this promising treatment [34]. The results from the Prosensa/GSK2402968 clinical study showed no substantial increase in dystrophin expression after the GSK drug Drisapersen was administered to trial participants and subsequently no significant differences using the 6-minute walk test (6MWT) as the primary endpoint were observed. However, Sarepta Therapeutics' lead exon skipping drug, Eteplirsen, which uses the phosphorodiamidate morpholino (PMO) to excise dystrophin exon 51, has been shown to induce substantial levels of dystrophin [35]. Eteplirsen was originally designed as a 2'OMeAO, based on in vitro studies by Stephen Wilton's group [36] and has stabilized ambulation as assessed in their 6 minute walk test [4]. In patients, reports have demonstrated that Eteplirsen, administered once weekly at either 30 mg/kg or 50 mg/kg for 48 weeks resulted in a statistically significant increase (p<0.001) in dystrophin-positive fibers to 47.0% of normal. The placebo or delayed treatment cohort, which had received 24 weeks of Eteplirsen at either 30 mg/kg or 50 mg/kg following 24 weeks of placebo (n=4), also showed a statistically significant increase in dystrophin-positive fibers to 38.3% of normal (p<0.009) (Sarepta Therapeutics News Release). Although exon skipping has been used successfully in X-linked disorders such as Duchenne muscular dystrophy to produce a smaller functional protein, it has only rarely been utilized in autosomal dominant disorders by knockdown of the disease allele as reported in fibrodysplasia ossificans progressiva (FOP). FOP is associated with the common R206H mutation in exon 8 of the ALK2 gene, which results in elevated BMP signaling. By using AONs to target exon 8 of ALK2, the reading frame is disrupted and the resulting mRNA is degraded by nonsense mediated decay due to the introduction of a stop codon [37]. Applicants' preliminary studies with Cre-ER™-VCP$^{R155H/+}$ mouse model show a promising avenue for therapeutic strategies such as allele decay by exon skipping for the human VCP-disease and potentially other genetic neurodegenerative disorders such as facioscapulohumeral muscular dystrophy.

Although having been recognized as a distinct syndrome in 2000, hereditary inclusion body myopathy (h-IBM), Paget disease of bone (PDB) and/or frontotemporal dementia (FTD), caused by dominantly inherited mutations in the Valosin Containing Protein (VCP) gene is an important disorder because it has led to many breakthroughs in understanding of the molecular pathogenesis of common disorders such as ALS. Histologically, patients show the presence of rimmed vacuoles and TDP-43 positive large ubiquitinated inclusion bodies in the muscles [8,11, 12, 13]. Kimonis et al. (2005, 2007, 2008) summarized findings in VCP myopathy and the various diagnoses provided by their physicians as limb girdle muscular dystrophy (LGMD), facioscapular muscular dystrophy, scapuloperoneal muscular dystrophy, or amyotrophic lateral sclerosis (ALS) [11, 14, 15].

Applicants' preliminary results from the generation of the Cre-ER™-VCP$^{R155H/+}$ mouse system have shown TAMOXIFEN™-inducible Cre recombinase excision of exons 4 and 5, resulting in an out-of-frame construct and a stop codon after exon 4. Applicants have characterized these mice and have discovered increased muscle strength and found improvements in muscle histology and in the autophagy transduction pathway (Nalbandian et al., 2013, in press, Appendix) [1]. Thus, Applicants now propose to study the effects of exon skipping drugs (antisense oligomers), to skip exon 5, in VCP$^{R155H/+}$ and IBMPFD patients' myoblasts in the initial phase of the study and subsequently in vivo in the knock-in VCP$^{R155H/+}$ animals. This pharmacological approach has great advantage because of a good safety record. The innovation lies in determining and optimizing the therapeutic potential of 2'O-Methyl phosphorothioate oligonucleotides in vitro as they are ideal research reagents for screening potential sequences which can be delivered systemically as cationic lipoplexes. Upon finding suitable candidate sequences for skipping, phosphorodiamidate morpholino oligomers (PMOs) or other oligonucleotide chemistries including peptide nucleic acids (PNA), locked nucleic acids (LNA), ethylene bridged nucleic acids (ENA) with phosphodiester or phosphorothioate or other backbones will be designed for in vivo testing in the VCP$^{R155H/+}$ mouse model and ultimately translated to human clinical trials. PMOs are ideal and have shown reduced side effects compared to 2'O-Methyl phosphorothioate oligonucleotides. This technology can potentially be used to treat muscles that are typically affected in VCP-associated musculoskeletal disease, thus providing the first effective treatment for VCP disease.

There are currently no treatments for VCP-associated neurodegenerative diseases and patients are dying early from respiratory failure related to muscle weakness. Recently, exon skipping therapies to cure Duchenne muscular dystrophy (DMD) have been used in mice, dystrophic dogs, and patients [4, 25, 50].

Specific disease mechanisms and novel therapeutic advancements underlying VCP-associated myopathies and neurodegenerative disorders are under further investigation. Evolutionarily, VCP is highly conserved and plays a significant role in several cellular processes in both unicellular and multicellular organisms. The knock-in VCP$^{R155H/+}$ mouse model exhibits progressive muscle weakness, and histological changes including inclusions and vacuoles in the muscle fibers, Paget-like bone changes and brain and spinal cord pathology of the human VCP disease, thereby providing a useful experimental platform to further investigate the mechanisms responsible for these VCP-associated disorders. Generation of conditional TAMOXIFEN™-inducible Cre-loxP mouse models have been utilized in a number of neuromuscular and degenerative diseases including inducible androgen receptor knockout models, spinal muscular atrophy (SMA), muscular dystrophies including Duchenne muscular dystrophy (DMD), Alzheimer's disease (AD), and amyotropic lateral sclerosis (ALS) [40]. Recently, exon skipping as a therapeutic platform has demonstrated successful treatment in DMD mice and patients [41-43]. Here, Applicants describe their novel TAMOXIFEN™-inducible Cre-ER-VCP$^{R155H/+}$ mouse line as a powerful tool and show that targeted excision of the R155H mutation in exons 4 and 5 ameliorates the phenotype typically observed in patients with VCP-associated disease.

In particular, when compared to the control corn oil (vehicle) Cre-ER™-VCP$^{R155H/+}$ mice, Applicants discovered a significant improvement in muscle strength measurements by the grip strength test and partial amelioration of the typical pathology of VCP-associated disease. Furthermore, impaired autophagy has been observed in several human diseases including myopathies and lysosomal storage disorders. Autophagy is a highly conserved mechanism, which is necessary for the maintenance of cellular homeostasis and orchestration of stress responses upregulated by oxidative stress, starvation or other harmful conditions. Applicants found that Cre-ER™-VCP$^{R155H/+}$ animals had an improvement in the autophagy cascade by the decrease observed in the p62/SQSTM1, LC3I/II, ubiquitin, and TDP-43 expression levels, a decrease in apoptotic cells and a decrease in the mitochondrial enzymes NADH and SDH in type I fibers, demonstrating a reduction in mitochondrial myopathy.

Frontotemporal dementia primarily affects the frontal and anterior temporal lobes of the brain with abnormalities in behavior, personality and language. Applicants observed decreased accumulation of TDP-43-, ubiquitin-, HT7(tau)-, and GFAP-positive inclusions in the brains of 18-month old Cre-ER™-VCP$^{R155H/+}$ TAMOXIFEN™-treated versus corn oil control mice. Also, the TDP-43-positive inclusions in the control corn oil (vehicle) VCP$^{R155H/+}$ mice were cytoplasmic, in contrast to the nuclear localization in the cortex and hippocampus of Cre-ER™-VCP$^{R155H/+}$ mice.

Paget disease of bone is usually characterized by osteoclastic lesions, abnormal bone remodeling bone deformities, and pathologic fractures. The osteoclastic activity leads to resorption of bone and shortly thereafter by hyperactivity of the osteoblasts, leading to a disordered deposition of new bone resulting in Pagetic-like lesions. The lesions become sclerotic in the later stages of PDB and bone marrow is replaced with fibrous tissue and increased bone thickness. Studies have shown that 10% patients with sporadic PDB and 50% familial PDB have gene mutations of Sequestosome 1 (SQSTM1). Studies have shown that P62/SQSTM1 plays an important role in the autophagic cascade and knockout mouse models have demonstrated focal osteolytic lesions on the hind limbs. Close inspection of the long hind limb bones by microCT reveals lucencies of the proximal tibias of 18-months old corn oil-treated Cre-ER™-VCP$^{R155H/+}$ suggestive of PDB. Applicants' studies suggest that the Cre-loxP technology excision of the R155H mutation from the VCP gene results in a partial amelioration of PDB-like changes.

This is the first report of the Cre-ERW™-VCP$^{R155H/+}$ mice using the ROSA version of the recombinase of the human estrogen receptor and crossing it with the VCP$^{R155H/+}$ mice to generate a novel excised R155H DNA segment flanked by loxP sites. There are several novel techniques currently available which are being used in other diseases that could make this translational to VCP-associated disease patients. This paper provides insight into exon splicing/skipping strategies in VCP-associated diseases and its translational therapeutic value for VCP patients. Cre-ER™-VCP$^{R155H/+}$ mice show improvements in the typical muscle pathology observed in the heterozygote mice carrying the R155H mutation. Although exon skipping has been used successfully in X-linked disorders such as Duchenne muscular dystrophy to produce a smaller functional protein, it has only rarely been utilized in autosomal dominant disorders by knockdown of the disease allele as reported in fibrodysplasia ossificans progressiva (FOP) [32, 41, 43, 44]. Thus, the Cre-ER™-VCP$^{R155H/+}$ mouse conclusively serves as a highly valuable model for novel therapeutic strategies such as allele silencing for the human VCP-disease among other neurodegenerative genetic disorders.

Exon skipping is used to restore the reading frame within a gene. Genes are the genetic instructions for creating a protein, and are composed of introns and exons. Exons are the sections of DNA that contain the instruction set for generating a protein; they are interspersed with non-coding regions called introns. The introns are later removed before the protein is made, leaving only the coding exon regions.

Splicing naturally occurs in pre-mRNA when introns are being removed to form mature-mRNA that consists solely of exons. Starting in the late 1990's, scientists realized they could take advantage of this naturally occurring cellular splicing to downplay genetic mutations into less harmful ones.

The mechanism behind exon skipping is a mutation specific antisense oligonucleotide (AONs). An antisense oligonucleotide is a synthesized short nucleic acid polymer, typically fifty or fewer base pairs in length that will bind to a relevant motif involved in the splicing of the mutated exon in the pre-messenger RNA, to induce targeted exon skipping. The AON binds to exon splice enhancers in the mutated exon, so that when the gene is transcribed, processed and eventually then translated, the mutated exon it is "skipped" over in the mature mRNA, thus restoring the disrupted reading frame. In some cases, it may be necessary to also remove an exon flanking the targeted mutated exon to maintain the reading frame to allow for the generation of an internally deleted but largely functional protein.

Some mutations require exon skipping at multiple sites, sometimes adjacent to one another, in order to restore the reading frame. Multiple exon skipping has successfully been carried out using a combination of AONs that target multiple exons.

Antisense oligonucleotides (AONs) are small synthetic RNA-like molecules consisting of 2'-O-methyl modified bases on a phosphorothioate backbone that are complimentary to exonic and/or flanking intronic sequences of the target exon. After transfection as a cationic lipoplex, appropriately designed AONs essentially mask the target exon from recognition by the splicing machinery, which removes it from the mature mRNA. In pre-clinical studies in the mdx mouse, 100% exon skipping has been routinely achieved in some tissues (diaphragm after intraperitoneal administration) [33].

In the human VCP disease, the majority of mutations occur in exon 5. Applicants will therefore target this exon for proposed studies. Applicants will design oligomers, typically 25mers directed to the acceptor and donor splice sites of exon 5, as well as motifs within the exon (splice enhancers) utilizing 2'O-methyl ribose modified bases on a phosphorothioate backbone, Applicants will use this technology to refine oligonucleotide design and PMOs will be used for subsequent in vivo studies. Applicants will design AONs to anneal splicing motifs and exonic splicing enhancer (ESE) motifs predicted by the web based application ESE finder [51]. Applicants will transfect these AONs into cultured $VCP^{R155H/+}$ and patient myoblast cells. The initial list of oligomer sequences is provide in Table 1 following.

TABLE 1

Oligomer sequence stargeting motifs in VCP exon 5 to induce exon skipping therapeutics for VCP disease. Nomenclature specifies exon target (5), A or D indicates acceptor or donor splice sites and the + or - describes exonic or intronic bases. Hence, VCPEx5A (-14+11) would anneal to the last 14 bases of intron 4 and the first 11 bases of exon 5. VCPEx5A (+15+36) is shorter due to the high G/C content

| Antisense Oligomers | Sequences(5'-3') |
|---|---|
| VCPEx5A (-14+11) | AAA AAU GUC UCC UGC GAG AGC AAA C (SEQ ID NO: 1) |
| VCPEx5A (+1+25) | CCA CCA UGG ACA AGA AAA AUG UCU C (SEQ ID NO: 2) |
| VCPEx5A (+15+36) | CAG CAC GCA UCC CAC CAU GGA C (SEQ ID NO: 3) |
| VCPEx5A (+76+100) | AUC ACU GUG UCU GGA GCA ACA AUG C (SEQ ID NO: 4) |
| VCPEx5A (+103+128) | UCG UUU GAU AGG CUC CCC UUC GCA G (SEQ ID NO: 5) |
| VCPEx5A (+7-18) | AUC AGG GAG AAA ACU CAC CUC UCG U (SEQ ID NO: 6) |

There are currently no treatments for VCP-associated neurodegenerative diseases and patients are dying early from respiratory failure related to muscle weakness. Recently, exon skipping therapies to cure Duchenne muscular dystrophy (DMD) have been used in mice, dystrophic dogs, and patients [4, 25, 50]. Applicants' preliminary results from the Cre-ER™-$VCP^{R155H/+}$ mouse system has demonstrated effective TAMOXIFEN™-inducible Cre recombinase splicing of exons 4 and 5. Thus, Applicants propose to develop, optimize and study the effects of exon skipping drugs (antisense oligonucleotides 2'O-MeAOs) in $VCP^{R155H/+}$ and IBMPFD patients' myoblasts. Applicants will subsequently study PMOs in the knock-in $VCP^{R155H/+}$ animals. This pharmacological approach has a great advantage because of a good safety record. These drugs can be delivered systemically and thus, potentially treat all muscles and other organs that are affected in patients with VCP neuromusculoskeletal disease.

Figure 8A:
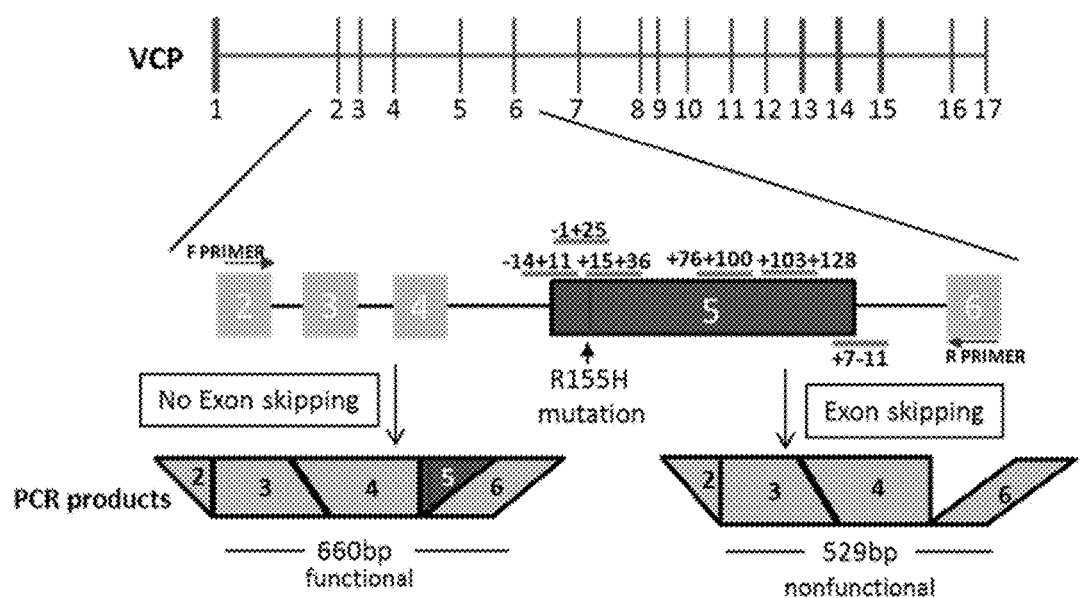
FIGS. 8A-8B. Exon skipping in VCP disease.
Figure 8B:
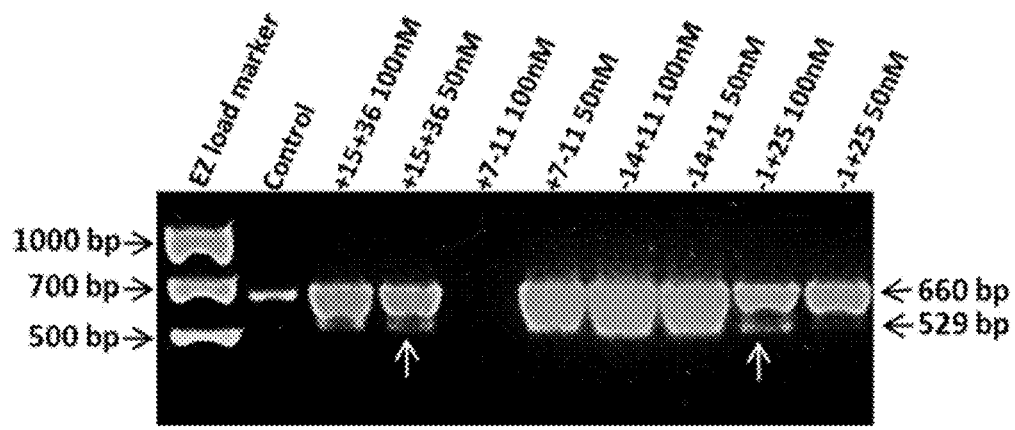

Murine $VCP^{R155H/+}$ and IBMPFD patients' and healthy donor myoblasts will be obtained and used. All of the cells will be seeded on a thin layer of collagen and will be grown in DMEM Skeletal Muscle Cell Basal Media supplemented with 15% FBS, 5% Pen/Strep, and 2% Glutamax to form into myotubes. Myoblasts will be transfected with Oligofectamine 2000 (L2K): AO at 1:1 ratio in Opti-MEM medium (Life Technologies, Carlsbad, Calif.) and treated with varying concentrations ranging between 400, 200, 100, 50, 25 and 10 nM for 8, 16, and 24 hours. After 24 to 48 hours incubation, RNA will be harvested from transfected cells and RT-PCR (to produce cDNA), followed by PCR undertaken to determine levels of exon skipping (FIGS. 8A and 8B). Untreated and sham treated (Oligofectamine only and a random oligomer) cells will be included to provide baseline levels. Applicants will assess oligonucleotide optimization and efficacy.

There have been no treatments for VCP-associated neurodegenerative diseases, and patients are dying early from respiratory failure related to muscle weakness. Recently, exon skipping therapies to cure Duchenne muscular dystrophy (DMD) have been used in mice, dystrophic dogs, and patients [4, 25, 50]. Applicants' results from the Cre-ER™-$VCP^{R155H/+}$ mouse system has demonstrated effective TAMOXIFEN™-inducible Cre recombinase splicing of exons 4 and 5. Thus, Applicants can develop, optimize and study the effects of exon skipping drugs (antisense oligonucleotides 2'O-MeAOs) in our $VCP^{R155H/+}$ and IBMPFD patients' myoblasts in the initial phase of the study and subsequently PMOs in the knock-in $VCP^{R155H/+}$ animals. This pharmacological approach has a great advantage because of a good safety record. These drugs can be delivered systemically and thus, potentially treat all muscles and other organs that are affected in patients with VCP neuromusculoskeletal disease. The Cre-ER™-$VCP^{R155H/+}$ mouse model provides proof-of-principle by demonstrating that removal of the mutated exons can be beneficial to patients suffering from VCP disease, and serves as an excellent platform in understanding the underlying pathophysiological mechanisms and may serve as a promising therapeutic approach for patients with VCP-related neurodegenerative diseases.

Example 3. Exon Skipping Therapeutics in VC-Associated Inclusion Body Myopathy

Inclusion Body Myopathy associated with Paget's disease of the bone and Frontotemporal Dementia, (IBMPFD, OMIM 167320), is attributed to mutations in the Valosin Containing Protein (VCP) gene mapped to the human chromosomal region 9p13.3-12. Affected individuals exhibit scapular winging and die from progressive muscle weakness, and cardiac and respiratory failure, typically in their 40's to 60's. Mutations in the VCP gene have also been associated with amyotrophic lateral sclerosis (ALS) in 10-15% of individuals with IBMPFD and 2-3% of isolated familial amyotrophic lateral sclerosis (fALS). In order to understand the cellular and molecular pathophysiological mechanism(s) underlying VCP-associated neurodegenerative diseases, Applicants have generated a unique Cre-ER™-VCP$^{R155H/+}$ TAMOXIFEN™-inducible mouse model. This technology allows determination of the effects of targeted excision of exons 4 and 5, including the R155H mutation, in VCP disease. Applicants administered pregnant dams with 0.12 mg/g body weight TAMOXIFEN™ or corn oil by oral gavage and monitored their survival and muscle strength of the pups until 18 months of age. The TAMOXIFEN™-treated Cre-ER™-VCP$^{R155H/+}$ mice demonstrated improved muscle strength and quadriceps muscles fiber architecture, reduced expression of autophagy markers, reduced brain neuropathology, decreased apoptosis, and partially rescued Paget's disease of bone. The Cre-ER™-VCP$^{R155H/+}$ mouse has provided proof-of-principle that excision of the R155H mutation may ameliorate VCP-associated disease in patients. Parallel studies using exon skipping therapeutics, which exclude specific exons, have been used successfully in muscle degenerative diseases such as Duchenne muscular dystrophy (DMD) and spinal muscular atrophy (SMA).

VCP-related disease is being more widely recognized with the identification of over 31 known mutations. The disclosed studies aim to design novel therapeutic approaches to control muscle weakness and progression in patients with VCP disease. Applicants' preliminary results from the Cre-ER™-VCP$^{R155H/+}$ mouse model system reveal that removing exons 4 and 5 may yield beneficial outcomes in VCP disease. Therefore, an additional goal is to provide personalized treatments by exon skipping therapeutics for patients with VCP disease using the cell and animal models disclosed herein.

Valosin containing protein (VCP) disease is an important disease that is increasingly being recognized, with over 31 VCP mutations having been identified worldwide. VCP, a member of the type II AAA+ATPase family, plays important roles in a plethora of cellular activities. There are currently no treatments for VCP-associated neurodegenerative diseases and patients are dying. Using the Cre-loxP technology, Applicants have discovered that targeted excision of the most common R155H mutation in the knock-in VCP$^{R155H/+}$ mice resulted in significant improvement in muscle strength and architecture, decreased protein expression levels of the autophagy cascade, reduced brain neuropathology, decreased cell death, and depicted a partial rescue of the Paget-like bone phenotype (Nalbandian et al., 2013 Appendix) [1]. The TAMOXIFEN™-induced Cre-ER™-VCP$^{R155H/+}$ mouse model thus may provide insights in developing treatment strategies for patients with VCP-associated and other neurodegenerative diseases. Recently, effective translational suppression technologies have emerged to silence alleles or skip exons in several diseases. Exon skipping has been used successfully in Duchenne muscular dystrophy (DMD) caused by out-of-frame deletions to produce a milder Becker-like phenotype, typically associated with an in-frame deletion. During processing of pre-mRNA, which is copied from the DNA template, introns are removed and exons are precisely spliced together to create the mature mRNA. By targeting elements in pre-mRNA that are essential for splicing, splice switching oligomers force the cellular machinery to skip over targeted exons, thereby creating an altered mRNA template, ultimately resulting in restored or neutralized protein by induced skipping of a specific exon.

Applicants' preliminary results from the Cre-ER™-VCP$^{R155H/+}$ mouse system have demonstrated effective TAMOXIFEN™-inducible Cre recombinase splicing of exons 4 and 5, the location of the majority of the VCP mutations. Exon 5 is also the location of the common human R155H VCP mutation seen in approximately half of affected individuals. Applicants have characterized these mice and have discovered increased muscle strength and improvements in muscle histology in the quadriceps muscles. Thus, Applicants propose to develop and study the effects of antisense oligomers in skipping the mutant exon in our IBMPFD patients' myoblasts in the initial phase of the study and subsequently in the VCP$^{R155H/+}$ mouse model system. This pharmacological approach has been shown to be promising in cxmd canine dogs in the treatment of muscular dystrophies such as Duchenne muscular dystrophy (DMD) [2,3] as well as in clinical trials in patients (Sarepta Therapeutics Communication).

Recent studies based on novel gene, cell and drug therapies in patients have shown promising exon skipping strategies to treat muscular dystrophies such as Duchenne muscular dystrophy (DMD) to make the disease milder like Becker muscular dystrophy (BMD) [2-4]. Applicants plan to explore the effect of exon skipping drugs on VCP-associated disease to improve the phenotype in the VCP$^{R155H/+}$ and patient myoblasts by administering various doses of antisense oligonucleotides (2'O-MeAOs) targeting the mutant VCP allele. Applicants will assess the efficacy and potential toxicity of these 2'O-MeAOs and analyze the phenotypical changes in the VCP$^{R155H/+}$ and patient myoblasts. 2'O-MeAOs can readily transfect cultured cells and are used as research reagents to refine splice switching oligomer design. Upon identification of lead candidate oligomers, phosphorodiamidate morpholino oligomers (PMOs) will be prepared and validated in vitro, prior to in vivo studies.

Studies have placed VCP at the intersection of the ubiquitin-proteasome and autophagy pathways, responsible for the homeostatic balance and turnover of damaged organelles [5,6]. Impaired autophagy has been implicated in VCP disease resulting in increased autophagosome formation [7]. Applicants will assess the efficiency of exon skipping by administering various doses of antisense oligonucleotides (PMOs) targeting the mutant VCP allele in the heterozygote VCP$^{R155H/+}$ mice. This will allow exploration of the effect of these drugs on muscle strength, typical pathological changes and signaling intermediates of the autophagy pathway including TDP-43, LC3 and ubiquitin pathologies. Applicants will evaluate the phenotype by plasma sampling and performing biochemical analyses on the muscles (gastrocnemius, quadriceps, tibialis anterior, triceps, and diaphragm) and organs (brain and spinal cord, bones, and heart) samples.

Hereditary inclusion body myopathy, Paget's disease of bone, and frontotemporal dementia caused by mutations in the VCP gene is associated with weakness and atrophy of skeletal, pelvic and shoulder girdle muscles in 90% of individuals [8-10]. Affected individuals exhibit scapular winging and progressive muscle weakness and die from cardiac and respiratory failure, typically in their 40's and 50's [8,11]. Histologically, patients display rimmed vacuoles and TDP-43-positive and ubiquitinated inclusion bodies in muscles [8,11,12,13]. Electron micrographs from affected skeletal muscle demonstrate prominent 15-21 nM tubulo-filamentous inclusions within myonuclei. Variable phenotypes are often diagnosed as limb girdle muscular dystrophy (LGMD), facioscapular muscular dystrophy or amyotrophic lateral sclerosis (ALS) [11, 14, 15]. ALS is a progressive neurodegenerative disease involving both upper (UMNs) and lower (LMNs) motor neurons. VCP mutations have been observed in 2-3% of isolated familial ALS cases [16].

Frontotemporal dementia (FTD) primarily affects the frontal and anterior temporal lobes of the brain with abnormalities of behavior and personality and language impairments variants. Applicants observed accumulation of TDP-43-, ubiquitin-, and GFAP-positive inclusions in the brains of 18-month old Cre-ER™-VCP$^{R155H/+}$ corn oil control mice, similar to that observed in FTD patients. In contrast, these autophagic markers depicted decreased expression levels in the TAMOXIFEN™-treated Cre Cre-ER™-VCP$^{R155H/+}$ mice. The TDP-43-positive inclusions in the control corn oil Cre-ER™-VCP$^{R155H/+}$ mice were cytoplasmic, in contrast to the nuclear localization in the cortex and hippocampus of TAMOXIFEN™-treated Cre-ER™-VCP$^{R155H/+}$ mice. Future studies will examine these intricate biological and molecular networks responsible for these phenotypes in order to develop novel therapies.

Paget disease of bone (PDB) is usually characterized by osteoclastic lesions, abnormal bone remodeling, bone deformities, and pathologic fractures. The osteoclastic activity leads to resorption of bone and shortly thereafter by hyperactivity of the osteoblasts, leading to a disordered deposition of new bone resulting in Pagetic lesions. The lesions become sclerotic in the later stages of PDB and bone marrow is replaced with fibrous tissue and increased bone thickness [17,18]. Recent studies have shown that 10% patients with sporadic PDB and 50% familial PDB have gene mutations of Sequestosome 1 (SQSTM1). Studies have shown that p62/SQSTM1 plays an important role in the autophagic cascade and knockout mouse models have demonstrated focal osteolytic lesions of the hind limbs [19]. Furthermore, in Applicants' studies, close inspection of the hind limb bones by microCT reveals PDB-like lucencies of the proximal tibias of 18-months old corn oil-treated CRE-ER™-VCP$^{R155H/+}$, not observed in the TAMOXIFEN™-treated animals (Nalbandian et al., 2013 Appendix) [1]. The Cre-LoxP mouse carrying the VCP gene may serve as a useful experimental model for understanding the underlying mechanisms in VCP disease and novel therapies.

Specific disease mechanisms and novel therapeutic advancements underlying VCP-associated myopathies and neurodegenerative disorders remain elusive and are under further investigation. IBMPFD is a neurodegenerative disease that is caused by mutations in VCP, known to be involved in several cellular processes. Evolutionally, VCP is highly conserved and plays a significant role in both unicellular and multicellular organisms. Applicants' knock-in VCP$^{R155H/+}$ mouse model exhibits progressive muscle weakness, and histological changes including inclusions and vacuoles in the muscle fibers, Paget-like bone changes and brain and spinal cord pathology of the human VCP disease, thereby providing a useful experimental platform to further investigate the mechanisms responsible for these VCP-associated disorders [20, 21]. Generation of conditional TAMOXIFEN™-inducible Cre-loxP mouse models have been utilized in a number of neuromuscular and degenerative diseases including muscular dystrophies including Duchenne muscular dystrophy (DMD), spinal muscular atrophy (SMA), inducible androgen receptor knockout models, Alzheimer's disease (AD), and ALS [22-24]. Furthermore, Applicants have generated a novel specific system to study VCP-associated disease: the TAMOXIFEN™-inducible CRe-ER™-VCP$^{R155H/+}$ mouse model, which offers value in assessing the role of targeted excision of the R155H mutation in exons 4 and 5 in ameliorating the phenotype observed in VCP-associated disease (Nalbandian et al., 2013 Appendix) [1]. Parallel studies using exon skipping as a therapeutic platform have demonstrated successful treatment in MDX mice, cxmd dogs and patients with DMD [25-27] and spinal muscular atrophy (SMA) [28].

Some of the most promising experimental approaches to treat muscular dystrophies such as Duchenne muscular dystrophy (DMD) are based on exon skipping strategies that convert the DMD to the milder Becker muscular dystrophy (BMD) [2-4]. DMD mutations disrupt the open reading frame and result in premature termination of translation. The truncated polypeptide is unstable and cannot form the stabilizing link between the actin cytoskeleton and the dystroglycan complex in the sarcolemma. This leads to major destabilization of the sarcolemma and weakness of muscle fibers that undergo constant damage due to stress forces generated by the working muscle [29]. The consequential loss of functional dystrophin results in muscle fibers with compromised, "leaky" membranes that disintegrate more rapidly than they can regenerate. This is in contrast to Becker muscular dystrophy (BMD), a milder form of the disease in which deletions preserve the reading frame. The resulting truncated dystrophin is still expressed and partially functional, allowing BMD patients to retain some muscle function [30-32]. In consequence, BMD is milder and the average lifespan of the patient is longer, in some cases close to normal.

Pharmacological and gene therapies include exon skipping drugs such as synthetic nucleic acid analogues called antisense oligonucleotides (AONs). Studies using cell penetrating peptide conjugated PMO-targeting dystrophin exon 23 in the dko (utrophin:dystrophin deficient) mouse which typically die 12-14 weeks after birth show a rescued phenotype, improved histopathology and an overall normal appearance at 1 year of age [33]. Previous studies using 2'-O-methyl-phosphorothioates (2'O-MPs) which were designed to excise several human DMD exons were successful in DMD patient-derived myotubes [31]. A phase I/II clinical trial has shown that this AON is reasonably tolerated in DMD patients and thus, a phase III study was initiated to explore this promising treatment [34]. The results from the Prosensa/GSK2402968 clinical study showed no substantial increase in dystrophin expression after the GSK drug Drisapersen was administered to trial participants and subsequently no significant differences using the 6-minute walk test (6MWT) as the primary endpoint were observed. However, Sarepta Therapeutics' lead exon skipping drug, Eteplirsen, which uses the phosphorodiamidate morpholino (PMO) to excise dystrophin exon 51, has been shown to induce substantial levels of dystrophin [35]. Eteplirsen was originally designed as a 2'OMeAO, based on in vitro studies by Stephen Wilton's group [36] and has stabilized ambulation as assessed in their 6 minute walk test [4]. In patients, reports have demonstrated that Eteplirsen, administered once weekly at either 30 mg/kg or 50 mg/kg for 48 weeks resulted in a statistically significant increase (p<0.001) in dystrophin-positive fibers to 47.0% of normal. The placebo or delayed treatment cohort, which had received 24 weeks of Eteplirsen at either 30 mg/kg or 50 mg/kg following 24 weeks of placebo (n=4), also showed a statistically significant increase in dystrophin-positive fibers to 38.3% of normal (p<0.009) (Sarepta Therapeutics News Release).

Although exon skipping has been used successfully in X-linked disorders such as Duchenne muscular dystrophy to produce a smaller functional protein, it has only rarely been utilized in autosomal dominant disorders by knockdown of the disease allele as reported in fibrodysplasia ossificans progressiva (FOP). FOP is associated with the common R206H mutation in exon 8 of the ALK2 gene which results in elevated BMP signaling. By using AONs to target exon 8 of ALK2, the reading frame is disrupted and the resulting mRNA is degraded by nonsense mediated decay due to the introduction of a stop codon [37]. Applicants' preliminary studies with Cre-ER™-VCP$^{R155H/+}$ mouse model shows a promising avenue for therapeutic strategies such as allele decay by exon skipping for the human VCP-disease and potentially other genetic neurodegenerative disorders.

Although having been recognized as a distinct syndrome in 2000, hereditary inclusion body myopathy (h-IBM), Paget disease of bone (PDB) and/or frontotemporal dementia (FTD), caused by dominantly inherited mutations in the Valosin Containing Protein (VCP) gene is an important disorder because it has led to many breakthroughs in understanding of the molecular pathogenesis of common disorders such as ALS. Histologically, patients show the presence of rimmed vacuoles and TDP-43 positive large ubiquitinated inclusion bodies in the muscles [8, 11, 12, 13]. Kimonis et al. (2005, 2007, 2008) summarized findings in VCP myopathy and the various diagnoses provided by their physicians as limb girdle muscular dystrophy (LGMD), facioscapular muscular dystrophy, scapuloperoneal muscular dystrophy, or amyotrophic lateral sclerosis (ALS) [11, 14, 15].

Applicants' preliminary results from the generation of the Cre-ER™-VCP$^{R155H/+}$ mouse system have shown TAMOXIFEN™-inducible Cre recombinase excision of exons 4 and 5, resulting in an out-of-frame construct and a stop codon after exon 4. Applicants have characterized these mice and have discovered increased muscle strength and found improvements in muscle histology and in the autophagy transduction pathway (Nalbandian et al., 2013, in press, Appendix) [1]. Thus, Applicants now propose to study the effects of exon skipping drugs (antisense oligomers), to skip exon 5, in our VCP$^{R155H/+}$ and IBMPFD patients' myoblasts in the initial phase of the study and subsequently in vivo in the knock-in VCP$^{R155/+}$ animals. This pharmacological approach has great advantage because of a good safety record. The innovation lies in determining and optimizing the therapeutic potential of 2'O-Methyl phosphorothioate oligonucleotides in vitro as they are ideal research reagents for screening potential sequences which can be delivered systemically as cationic lipoplexes. Upon finding suitable candidate sequences for skipping, phosphorodiamidate morpholino oligomers (PMOs) will be designed for in vivo testing in the VCP$^{R155H/+}$ mouse model and ultimately translated to human clinical trials. PMOs are ideal and have shown reduced side effects compared to 2'O-Methyl phosphorothioate oligonucleotides. This technology can potentially be used to treat muscles that are typically affected in VCP-associated musculoskeletal disease, thus providing the first effective treatment for VCP disease.

Figure 9A:
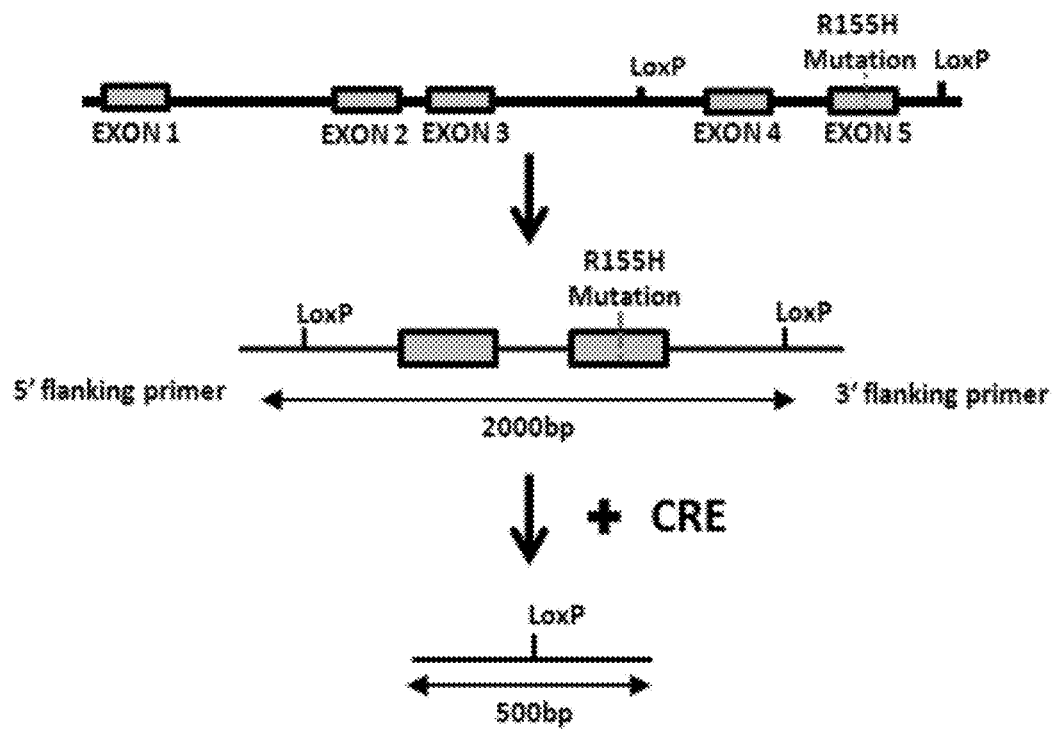
FIGS. 9A-9C. Cre-mediated recombination and functionality in CRE-ER™-VCP$^{R155H/+}$ mice.
Figure 9B:
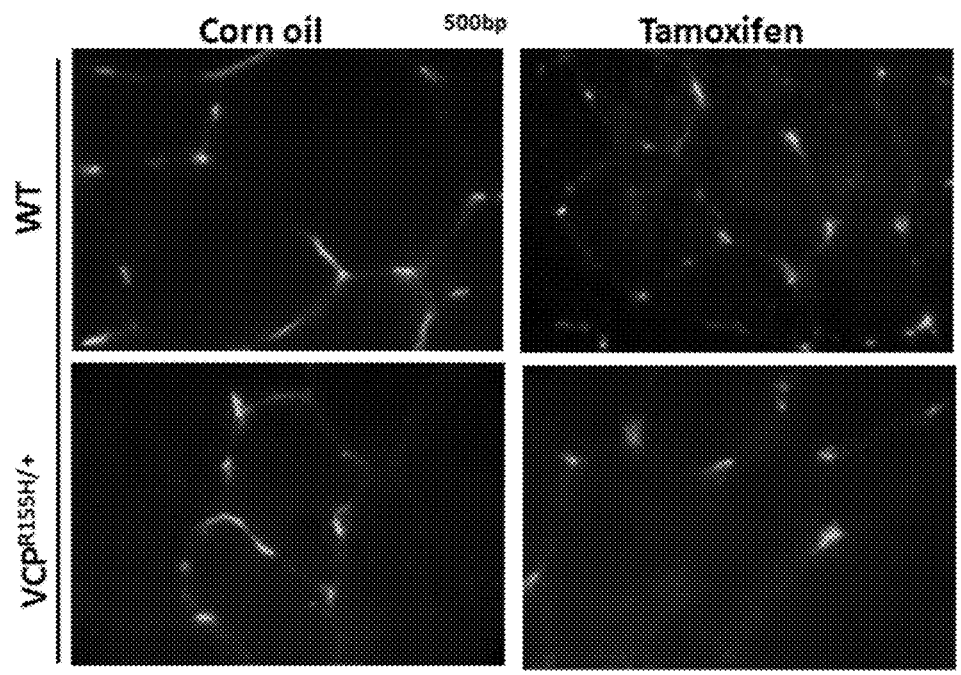
Figure 9C:
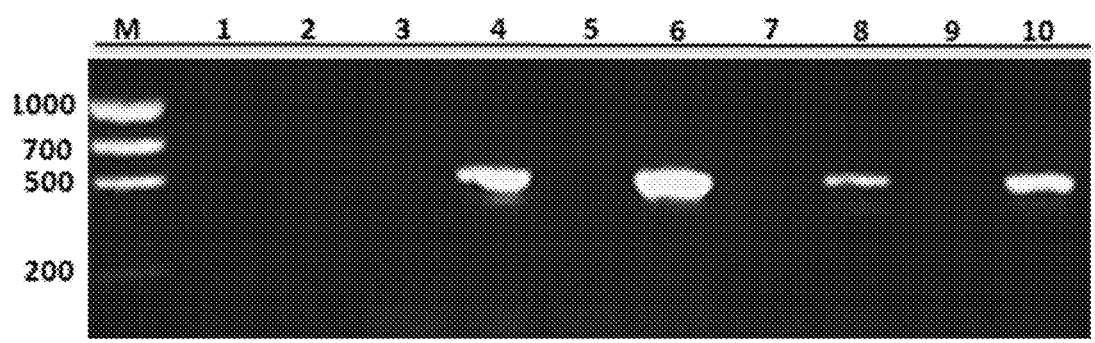

Targeted excision of the VCP R155H mutation in the Cre-ER™-VCP$^{R155H/+}$ mouse model ameliorates the phenotype. Generation of TAMOXIFEN™-inducible Cre models has become the gold standard for determining gene function in mice by allowing the phenotypic analyses for selected tissues during embryonic development. The innovation of this model lies in the generation of a transgenic TAMOXIFEN™-inducible Cre-ER™-VCP$^{R155H/+}$ mouse system with the targeted excision of the VCP R155H mutation in exons 4 and 5. Efficient nuclear translocation of the Cre protein was observed by immunohistochemical analyses (FIG. 9B). PCR primers flanking the loxp sites, gave rise to a 500 base pair PCR product when the region is deleted, confirming efficient Cre-mediated recombination of the VCP gene in the Cre-ER™-VCP$^{R155H/+}$ pups in skeletal muscle, liver, kidney, and brain samples (FIG. 9C). The TAMOXIFEN™-inducible Cre-mediated excision of the VCP mutation resulted in an out-of-frame transcript and a stop codon. Applicants assessed the efficiency and functionality of Cre recombination in the TAMOXIFEN™-treated VCP$^{R155H/+}$ mice. Immunohistochemical analysis of the quadriceps muscles showed decreased expression levels of VCP. Applicants' preliminary evidence from characterization studies of untreated WT and VCP$^{R155H/+}$ animals depicted modest differences in weight and an improvement in grip strength and quadriceps histology (FIG. 2). Immunohistochemical analysis of the quadriceps muscles showed decreased expression levels of ubiquitin, and TDP-43 (data not shown) suggesting amelioration of the typical phenotypic features of VCP-associated features [1].

The autophagy signaling pathway has been implicated as an important process in mediating protein degradation for terminally differentiated cells and as a key mechanism for VCP regulation and function. On inducing autophagy, a phagophore first sequesters cytoplasmic constituents; together, they subsequently form a double-membrane structure known as the autophagosome, which then fuse with lysosomal vesicles and forms digestive autolysosomes [38]. Studies suggest that the autophagic process is related to cell cycle regulation, starvation adaptation, aging, and cancer development. Recent studies have shown that p62/SQSTM1 plays a key role in the autophagic uptake of aggregated proteins [39].

VCP is important for the retro-translocation of misfolded ER proteins, and failure in this activity results in defective ERAD and ER stress responses [40]. Weihl et al. (2006) have previously shown in cultured cells that mutant VCP fails to degrade prototypical ERAD substrates [41]. Autophagic degradation also is involved in Alzheimer's disease and Huntington's disease, and other neurodegenerative disorders [42-46]. Applicants have observed accumulation of enlarged vacuoles as well as several other cellular dysfunctions in patients' myoblast cells versus normal control myoblasts; these observations provide the rationale for some of the experiments proposed here [47,48]. Similarly, mitophagy, selective autophagy of mitochondria, is an important control mechanism that mediates the removal of damaged mitochondria in cells, whereby defects in this process have been implicated in neurodegeneration. VCP plays a critical role in maintaining mitochondrial quality and dynamics in the PINK1/Parkin pathway, whereby pathogenic mutations in VCP lead to an impairment in proteasome-dependent degradation [49].

Determination of the exon skipping therapeutic potential and its effects in the VCP$^{R155H/+}$ knock-in heterozygote mouse model. Applicants will administer pharmacological exon skipping drugs in vivo in the mouse to ameliorate the VCP-associated phenotype and significantly improve the autophagy transduction pathway. Both oligomer chemistries will be tested.

There are currently no treatments for VCP-associated neurodegenerative diseases and patients are dying early from respiratory failure related to muscle weakness. Recently, exon skipping therapies to cure Duchenne muscular dystrophy (DMD) have been used in mice, dystrophic dogs, and patients [4, 25, 50]. Applicants' preliminary results from the Cre-ER™-VCP$^{R155H/+}$ mouse system has demonstrated effective TAMOXIFEN™-inducible Cre recombinase splicing of exons 4 and 5. Applicants now propose to develop, optimize and study the effects of exon skipping drugs (antisense oligonucleotides 2'O-MeAOs) in VCP$^{R155H/+}$ and IBMPFD patients' myoblasts in the initial phase of the study and subsequently PMOs in the knock-in VCP$^{R155H/+}$ animals. This pharmacological approach has a great advantage because of a good safety record. These drugs can be delivered systemically and thus, potentially treat all muscles and other organs that are affected in patients with VCP neuromusculoskeletal disease.

Murine VCP$^{R155H/+}$ and IBMPFD patients' and healthy donor myoblasts will be obtained and used. All of the cells will be seeded on a thin layer of collagen and will be grown in DMEM Skeletal Muscle Cell Basal Media supplemented with 15% FBS, 5% Pen/Strep, and 2% Glutamax to form into myotubes. Myoblasts will be transfected with Oligofectamine 2000 (L2K): AO at 1:1 ratio in Opti-MEM medium (Life Technologies, Carlsbad, Calif.) and treated with varying concentrations ranging between 400, 200, 100, 50, 25 and 10 nM for 8, 16, and 24 hours. After 24 to 48 hours incubation, RNA will be harvested from transfected cells and RT-PCR (to produce cDNA), followed by PCR undertaken to determine levels of exon skipping (FIG. 8). Untreated and sham treated (Oligofectamine only and a random oligomer) cells will be included to provide baseline levels. Applicants will assess oligonucleotide optimization and efficacy.

Cytotoxicity will be measured using the MTS assay by Cell Titer Proliferation kit (Promega, Madison, Wis.) according to the manufacturer's instructions. Briefly, cells will be seeded in a 96-well culture plate at 1×10$_4$ cells per well and will be exposed to the various AONs at the desirable doses for 24 hours. The absorbance at 570 nm will be measured. Untreated cells will be used as controls of 100% viability. Applicants will analyze cell histomorphology by light microscopy.

PCR Assay. Cell lysates from VCP$^{R155H/+}$ patients and myoblasts will be prepared. RNA will be extracted using the TRIzol method (Life Technologies). 100 ng of RNA template will be used for a 50 1 RT-PCR reaction (Stratagene, Santa Clara, Calif.). It has been shown that altering the oligomer length can influence exon skipping levels [52]. cDNA from RT-PCR reaction will then be tested for skipping of exon 5 using primers located in exon 2 (forward primer-agctgtttgcatcgtcctt) and exon 6 (reverse primer-ggttgctctcagactcacca) (FIGS. 8A and 8B).

Patient and myoblast cells and harvested mouse tissues from muscles, spinal cords, diaphragm and brains will be subjected to immunohistochemistry as described previously. Primary antibodies for VCP, ubiquitin, myogenin, LC3-I/II, p62/SQSTM1, LAMP-1 and LAMP-2, and TDP-43 and will be incubated on sections overnight at 4° C. and incubated with fluorescein-conjugated secondary antibodies (Sigma-Aldrich) and mounted with DAPI-mounting media (Vector Laboratories, Inc.).

Protein lysates from patients and VCP$^{R155H/+}$ myoblasts will be prepared for Western blotting as previously described [21]. Applicants will analyze autophagy signaling intermediates including TDP-43, ubiquitin, ubiquitin-activating enzymes, ubiquitin-conjugating enzymes, ubiquitin-protein ligases, LC3-I/II, Beclin-1, Atg12-Atg5-Atg16, p62/SQSTM1, and mitochondrial markers in the patients' myoblasts cells, WT and heterozygote animals.

Once Applicants have identified efficient exon skipping antisense oligonucleotides (2'O-MeAOs) in the myoblasts, Applicants plan to move to the second phase to use PMOs to examine their ability to induce exon skipping in Applicants' VCP mouse model. VCP$^{R155H/+\ or\ WT\ mice}$ (10-months of age) will receive the PMOs or physiological saline control administered 1) intramuscularly (i.m.) in one quadriceps leg versus saline in the other leg 2) intravenously (i.v.) (a dose of 80-640 mg/kg PMOs or control physiological saline) for a total drug delivery of 8 weeks, twice weekly. All mice will be monitored throughout the study and sacrificed 2 weeks after the last injection. At 12-months of age, Applicants will sacrifice 5 animals and continue treatments up to 18-months of age [26, 53].

Muscle strength will be determined using Rotarod and grip strength measurements as previously described [21]. *Rotarod accelerating speed protocol*: Mice will be placed on the Rotarod and mice tend to grip the rod and "ride" the Rotarod. *Grip Strength test*: The grip strength test measures the muscle strength of the forelimbs.

Blood will be collected from the VCP$^{R155H/+}$ and WT animals treated with AONs and measurements will include creatinine phosphokinase, alkaline phosphatase, glucose, electrolytes, transaminases, lactate dehydrogenase, creatinine, calcium, magnesium [54].

Applicants will perform electrodiagnostic studies measuring nerve conduction velocity on WT and VCP$^{R155H/+}$ animals treated with PMOs to determine whether the mice also exhibit neurophysiological changes seen in patients with ALS as described previously [55].

REFERENCES FOR EXAMPLE 1

[1]. Kimonis, V. E., Kovach, M. J., Waggoner, B., Leal, S., Salam, A., Rimer, L., Davis, K., Khardori, R. and Gelber, D. (2000) Clinical and molecular studies in a unique family with autosomal dominant limbgirdle muscular dystrophy and Paget disease of bone. *Genet Med*, 2, 232-241.

[2]. Kovach, M. J., Waggoner, B., Leal, S. M., Gelber, D., Khardori, R., Levenstien, M. A., Shanks, C. A., Gregg, G., Al-Lozi, M. T., Miller, T. et al. (2001) Clinical delineation and localization to chromosome 9p13.3-p12 of a unique dominant disorder in four families: hereditary inclusion body myopathy, Paget disease of bone, and frontotemporal dementia. *Molecular genetics and metabolism*, 74, 458-475.

[3]. Watts, G. D., Thorne, M., Kovach, M. J., Pestronk, A. and Kimonis, V. E. (2003) Clinical and genetic heterogeneity in chromosome 9p associated hereditary inclusion body myopathy: exclusion of GNE and three other candidate genes. *Neuromuscul Disord*, 13, 559-567.

[4]. Watts, G. D., Wymer, J., Kovach, M. J., Mehta, S. G., Mumm, S., Darvish, D., Pestronk, A., Whyte, M. P. and Kimonis, V. E. (2004) Inclusion body myopathy associated with Paget disease of bone and frontotemporal dementia is caused by mutant valosin-containing protein. *Nature genetics*, 36, 377-381.

[5]. Kimonis, V. E., Mehta, S. G., Fulchiero, E. C., Thomasova, D., Pasquali, M., Boycott, K., Neilan, E. G., Kartashov, A., Forman, M. S., Tucker, S. et al. (2008) Clinical studies in familial VCP myopathy associated with Paget disease of bone and frontotemporal dementia. *American journal of medical genetics*, 146, 745-757.

[6]. Kimonis, V. E., Fulchiero, E., Vesa, J. and Watts, G. (2008) VCP disease associated with myopathy, paget disease of bone and frontotemporal dementia: Review of a unique disorder. *Biochimica et biophysica acta*.

[7]. Kimonis, V., Donkervoort, S. and Watts, G. (2011), In *Gene Tests and University of Washington, Seattle*.

[8]. Kimonis, V. E. and Watts, G. D. (2005) Autosomal dominant inclusion body myopathy, Paget disease of bone, and frontotemporal dementia. *Alzheimer disease and associated disorders*, 19 Suppl 1, S44-47.

[9]. Schroder, R., Watts, G. D., Mehta, S. G., Evert, B. O., Broich, P., Fliessbach, K., Pauls, K., Hans, V. H., Kimonis, V. and Thal, D. R. (2005) Mutant valosin-containing protein causes a novel type of frontotemporal dementia. *Annals of neurology*, 57, 457-461.

[10]. Djamshidian, A., Schaefer, J., Haubenberger, D., Stogmann, E., Zimprich, F., Auff, E. and Zimprich, A. (2009) A novel mutation in the VCP gene (G157R) in a German family with inclusion-body myopathy with Paget disease of bone and frontotemporal dementia. *Muscle & nerve*, 39, 389-391.

[11]. Guyant-Marechal, L., Laquerriere, A., Duyckaerts, C., Dumanchin, C., Bou, J., Dugny, F., Le Ber, I., Frebourg, T., Hannequin, D. and Campion, D. (2006) Valosin-containing protein gene mutations: clinical and neuropathologic features. *Neurology*, 67, 644-651.

[12]. Haubenberger, D., Bittner, R. E., Rauch-Shorny, S., Zimprich, F., Mannhalter, C., Wagner, L., Mineva, I., Vass, K., Auff, E. and Zimprich, A. (2005) Inclusion body myopathy and Paget disease is linked to a novel mutation in the VCP gene. *Neurology*, 65, 1304-1305.

[13]. Bersano, A., Del Bo, R., Lamperti, C., Ghezzi, S., Fagiolari, G., Fortunato, F., Ballabio, E., Moggio, M., Candelise, L., Galimberti, D. et al. (2007) Inclusion body myopathy and frontotemporal dementia caused by a novel VCP mutation. *Neurobiology of aging*.

[14]. Viassolo, V., Previtali, S. C., Schiatti, E., Magnani, G., Minetti, C., Zara, F., Grasso, M., Dagna-Bricarelli, F. and Di Maria, E. (2008) Inclusion body myopathy, Paget's disease of the bone and frontotemporal dementia: recurrence of the VCP R155H mutation in an Italian family and implications for genetic counselling. *Clinical genetics*.

[15]. Miller, T. D., Jackson, A. P., Barresi, R., Smart, C. M., Eugenicos, M., Summers, D., Clegg, S., Straub, V. and Stone, J. (2009) Inclusion body myopathy with Paget disease and frontotemporal dementia (IBMPFD): clinical features including sphincter disturbance in a large pedigree. *Journal of neurology, neurosurgery, and psychiatry*, 80, 583-584.

[16]. Kumar, K. R., Needham, M., Mina, K., Davis, M., Brewer, J., Staples, C., Ng, K., Sue, C. M. and Mastaglia, F. L. (2010) Two Australian families with inclusion-body myopathy, Paget's disease of bone and frontotemporal dementia: novel clinical and genetic findings. *Neuromuscul Disord*, 20, 330-334.

[17]. Fanganiello, R. D., Kimonis, V., Nitrini, R. and Passos-Bueno, M. R. (2011) A Brazilian family with IBMPFD caused by p. R93C mutation in the VCP gene and literature review for genotype-phenotype correlations. *Experimental Brain Research—Manuscript ID EBR*-10-0487

[18]. Kim, E. J., Park, Y. E., Kim, D. S., Ahn, B. Y., Kim, H. S., Chang, Y. H., Kim, S. J., Kim, H. J., Lee, H. W., Seeley, W. W. et al. (2011) Inclusion body myopathy with Paget disease of bone and frontotemporal dementia linked to VCP p. Arg155Cys in a Korean family. *Archives of neurology*, 68, 787-796.

[19]. Komatsu, J., Iwasa, K., Yanase, D. and Yamada, M. (2013) Inclusion body myopathy with Paget disease of the bone and frontotemporal dementia associated with a novel G156S mutation in the VCP gene. *Muscle & nerve*.

[20]. Spina, S., Van Laar, A., Murrell, J. R., de Courten-Myers, G., Hamilton, R. L., Farlow, M. R., Quinlan, J., DeKosky, S. T. and Ghetti, B. (2008) Frontotemporal dementia associated with a Valosin-Containing Protein mutation: report of three families. *The FASEB Journal* 22, 58.54.

[21]. Watts, G. D., Thomasova, D., Ramdeen, S. K., Fulchiero, E. C., Mehta, S. G., Drachman, D. A., Weihl, C. C., Jamrozik, Z., Kwiecinski, H., Kaminska, A. et al. (2007) Novel VCP mutations in inclusion body myopathy associated with Paget disease of bone and frontotemporal dementia. *Clinical genetics*, 72, 420-426.

[22]. Johnson, J. O., Mandrioli, J., Benatar, M., Abramzon, Y., Van Deerlin, V. M., Trojanowski, J. Q., Gibbs, J. R., Brunetti, M., Gronka, S., Wuu, J. et al. (2010) Exome sequencing reveals VCP mutations as a cause of familial ALS. *Neuron*, 68, 857-864.

[23]. Kim, N.C., Tresse, E., Kolaitis, R. M., Molliex, A., Thomas, R. E., Alami, N. H., Wang, B., Joshi, A., Smith, R. B., Ritson, G. P. et al. (2013) VCP Is Essential for Mitochondrial Quality Control by PINK1/Parkin and this Function Is Impaired by VCP Mutations. *Neuron*.

[24]. DeLaBarre, B., Christianson, J. C., Kopito, R. R. and Brunger, A. T. (2006) Central pore residues mediate the p97/VCP activity required for ERAD. *Molecular cell*, 22, 451-462.

[25]. Wong, E. and Cuervo, A. M. Autophagy gone awry in neurodegenerative diseases. *Nature neuroscience*, 13, 805-811.

[26]. Komatsu, M., Kominami, E. and Tanaka, K. (2006) Autophagy and neurodegeneration. *Autophagy*, 2, 315-317.

[27]. Malicdan, M. C. and Nishino, I. (2012) Autophagy in lysosomal myopathies. *Brain pathology* (Zurich, Switzerland), 22, 82-88.

[28]. Levine, B. and Kroemer, G. (2008) Autophagy in the pathogenesis of disease. *Cell*, 132, 27-42.

[29]. Tung, Y. T., Wang, B. J., Hu, M. K., Hsu, W. M., Lee, H., Huang, W. P. and Liao, Y. F. (2012) Autophagy: a double-edged sword in Alzheimer's disease. *J Biosci*, 37, 157-165.

[30]. Kemaladewi, D. U., Hoogaars, W. M., van Heiningen, S. H., Terlouw, S., de Gorter, D. J., den Dunnen, J. T., van Ommen, G. J., Aartsma-Rus, A., ten Dijke, P. and t Hoen, P. A. (2011) Dual exon skipping in myostatin and dystrophin for Duchenne muscular dystrophy. *BMC Med Genomics*, 4, 36.

[31]. Pichavant, C., Aartsma-Rus, A., Clemens, P. R., Davies, K. E., Dickson, G., Takeda, S., Wilton, S. D., Wolff, J. A., Wooddell, C. I., Xiao, X. et al. (2011) Current status of pharmaceutical and genetic therapeutic approaches to treat DMD. *Mol Ther*, 19, 830-840.

[32]. Shi, S., Cai, J., de Gorter, D. J., Sanchez-Duffhues, G., Kemaladewi, D. U., Hoogaars, W. M., Aartsma-Rus, A., t Hoen, P. A. and Ten Dijke, P. (2013) Antisense-oligonucleotide mediated exon skipping in activin-receptor-like kinase 2: inhibiting the receptor that is overactive in fibrodysplasia ossificans progressiva. *PLoS ONE*, 8, e69096.

[33]. Verrou, C., Zhang, Y., Zurn, C., Schamel, W. W. and Reth, M. (1999) Comparison of the TAMOXIFEN™ regulated chimeric Cre recombinases MerCreMer and CreMer. *Biological chemistry*, 380, 1435-1438.

[34]. Zhang, W., Hinton, D. R., Surnock, A. A. and Couldwell, W. T. (1996) Malignant glioma sensitivity to radiotherapy, high-dose TAMOXIFEN™, and hypericin:

corroborating clinical response in vitro: case report. *Neurosurgery*, 38, 587-590; discussion 590-581.

[35]. Badadani, M., Nalbandian, A., Watts, G. D., Vesa, J., Kitazawa, M., Su, H., Tanaja, J., Dec, E., Wallace, D. C., Mukherjee, J. et al. (2010) VCP associated inclusion body myopathy and paget disease of bone knock-in mouse model exhibits tissue pathology typical of human disease. *PLoS ONE*, 5.

[36]. Nalbandian, A., Llewellyn, K. J., Badadani, M., Yin, H. Z., Nguyen, C., Katheria, V., Watts, G., Mukherjee, J., Vesa, J., Caiozzo, V. et al. (2013) A progressive translational mouse model of human valosin-containing protein disease: the VCP(R155H/+) mouse. *Muscle & nerve*, 47, 260-270.

[37]. Vesa, J., Su, H., Watts, G. D., Krause, S., Walter, M. C., Martin, B., Smith, C., Wallace, D. C. and Kimonis, V. E. (2009) Valosin containing protein associated inclusion body myopathy: abnormal vacuolization, autophagy and cell fusion in myoblasts. *Neuromuscul Disord*, 19, 766-772.

[38]. de Medina, P., Silvente-Poirot, S. and Poirot, M. (2009) TAMOXIFEN™ and AEBS ligands induced apoptosis and autophagy in breast cancer cells through the stimulation of sterol accumulation. *Autophagy*, 5, 1066-1067.

[39]. Kudoh, H., Ikeda, H., Kakitani, M., Ueda, A., Hayasaka, M., Tomizuka, K. and Hanaoka, K. (2005) A new model mouse for Duchenne muscular dystrophy produced by 2.4 Mb deletion of dystrophin gene using Cre-loxP recombination system. *Biochemical and biophysical research communications*, 328, 507-516.

[40]. Aoki, Y., Yokota, T., Nagata, T., Nakamura, A., Tanihata, J., Saito, T., Duguez, S. M., Nagaraju, K., Hoffman, E. P., Partridge, T. et al. (2012) Bodywide skipping of exons 45-55 in dystrophic mdx52 mice by systemic antisense delivery. *Proceedings of the National Academy of Sciences of the United States of America*, 109, 13763-13768.

[41]. Malerba, A., Kang, J. K., McClorey, G., Saleh, A. F., Popplewell, L., Gait, M. J., Wood, M. J. and Dickson, G. (2012) Dual Myostatin and Dystrophin Exon Skipping by Morpholino Nucleic Acid Oligomers Conjugated to a Cell-penetrating Peptide Is a Promising Therapeutic Strategy for the Treatment of Duchenne Muscular Dystrophy. *Mol Ther Nucleic Acids*, 1, e62.

[42]. Yang, L., Niu, H., Gao, X., Wang, Q., Han, G., Cao, L., Cai, C., Weiler, J. and Yin, H. (2013) Effective exon skipping and dystrophin restoration by 2'-o-methoxyethyl antisense oligonucleotide in dystrophin-deficient mice. *PLoS ONE*, 8, e61584. —[43]. Wu, B., Moulton, H. M., Iversen, P. L., Jiang, J., Li, J., Li, J., Spurney, C. F., Sali, A., Guerron, A. D., Nagaraju, K. et al. (2008) Effective rescue of dystrophin improves cardiac function in dystrophindeficient mice by a modified morpholino oligomer. *Proceedings of the National Academy of Sciences of the United States of America*, 105, 14814-14819.

REFERENCES FOR EXAMPLES 2 AND 3

[1]. Nalbandian A, et al., 2013, Molecular Therapy Methods and Clinical Development. (in review)

[2]. Kemaladewi D U, et al., 2011, BMC Med Genomics 4: 36.

[3]. Pichavant C, et al., 2011, Mol Ther 19: 830-840.

[4]. Mendell, J R, et al., 2013, Ann Neurol. 74:637-647.

[5]. Ju J S, et al., 2008, J Biol Chem 283: 30289-30299.

[6]. Ju J S, et al., 2009, J Cell Biol 187: 875-888.

[7]. Ju J S & Weihl C C, 2010, Autophagy 6:283-285.

[8]. Kimonis V E, et al., 2000, Genet Med 2: 232-241.

[9]. Kovach M J, Waggoner B, Leal S M, Gelber D, Khardori R, et al. (2001) Clinical delineation and localization to chromosome 9p13.3-p12 of a unique dominant disorder in four families: hereditary inclusion body myopathy, Paget disease of bone, and frontotemporal dementia. Mol Genet Metab 74: 458-475.

[10]. Watts G D, Thorne M, Kovach M J, Pestronk A, Kimonis V E (2003) Clinical and genetic heterogeneity in chromosome 9p associated hereditary inclusion body myopathy: exclusion of GNE and three other candidate genes. Neuromuscul Disord 13: 559-567.

[11]. Kimonis V E, Mehta S G, Fulchiero E C, Thomasova D, Pasquali M, et al. (2008) Clinical studies in familial VCP myopathy associated with Paget disease of bone and frontotemporal dementia. Am J Med Genet A 146: 745-757.

[12]. Watts G D, Wymer J, Kovach M J, Mehta S G, Mumm S, et al. (2004) Inclusion body myopathy associated with Paget disease of bone and frontotemporal dementia is caused by mutant valosin-containing protein. Nat Genet 36: 377-381.

[13]. Kimonis V E, Fulchiero E, Vesa J, Watts G (2008) VCP disease associated with myopathy, paget disease of bone and frontotemporal dementia: Review of a unique disorder. Biochim Biophys Acta.

[14]. Kimonis V, Donkervoort S, Watts G (2011) Inclusion Body Myopathy Associated with Paget Disease of Bone and/or Frontotemporal Dementia Gene GeneTests (www-genetestsorg) and University of Washington, Seattle.

[15]. Kimonis V E, Watts G D (2005) Autosomal dominant inclusion body myopathy, Paget disease of bone, and frontotemporal dementia. Alzheimer Dis Assoc Disord 19 Suppl 1: S44-47.

[16]. Johnson J O, Mandrioli J, Benatar M, Abramzon Y, Van Deerlin V M, et al. (2010) Exome sequencing reveals VCP mutations as a cause of familial ALS. Neuron 68: 857-864.

[17]. Ralston S H (2008) Pathogenesis of Paget's disease of bone. Bone 43: 819-825.

[18]. Ralston S H (2013) Clinical practice. Paget's disease of bone. N Engl J Med 368: 644-650.

[19]. Daroszewska A, van't Hof R J, Rojas J A, Layfield R, Landao-Basonga E, et al. (2011) A point mutation in the ubiquitin-associated domain of SQSMT1 is sufficient to cause a Paget's disease-like disorder in mice. Hum Mol Genet 20: 2734-2744.

[20]. Badadani M, Nalbandian A, Watts G D, Vesa J, Kitazawa M, et al. (2010) VCP associated inclusion body myopathy and paget disease of bone knock-in mouse model exhibits tissue pathology typical of human disease. PLoS ONE 5.

[21]. Nalbandian A, Llewellyn K J, Badadani M, Yin H Z, Nguyen C, et al. (2013) A progressive translational mouse model of human valosin-containing protein disease: the VCP(R155H/+) mouse. Muscle Nerve 47: 260-270.

[22]. Donnelly E M, Quach E T, Hillery™, Heeke B L, Snyder B R, et al. (2012) Characterization of a murine model of SMA. Neurobiol Dis 45: 992-998.

[23]. Kudoh H, Ikeda H, Kakitani M, Ueda A, Hayasaka M, et al. (2005) A new model mouse for Duchenne muscular dystrophy produced by 2.4 Mb deletion of dystrophin gene using Cre-loxP recombination system. Biochem Biophys Res Commun 328: 507-516.

[24]. Zhang X, Li H, Mao Y, Li Z, Wang R, et al. (2013) An Over Expression APP Model for Anti-Alzheimer Disease Drug Screening Created by Zinc Finger Nuclease Technology. PLoS One 8: e75493.

[25]. Aoki Y, Yokota T, Nagata T, Nakamura A, Tanihata J, et al. (2012) Bodywide skipping of exons 45-55 in dystrophic mdx52 mice by systemic antisense delivery. Proc Natl Acad Sci USA 109: 13763-13768.

[26]. Malerba A, Kang J K, McClorey G, Saleh A F, Popplewell L, et al. (2012) Dual Myostatin and Dystrophin Exon Skipping by Morpholino Nucleic Acid Oligomers Conjugated to a Cell-penetrating Peptide Is a Promising Therapeutic Strategy for the Treatment of Duchenne Muscular Dystrophy. Mol Ther Nucleic Acids 1: e62.

[27]. Yang L, Niu H, Gao X, Wang Q, Han G, et al. (2013) Effective exon skipping and dystrophin restoration by 2'-o-methoxyethyl antisense oligonucleotide in dystrophin-deficient mice. PLoS One 8: e61584.

[28]. Sivanesan S, Howell M D, Didonato C J, Singh R N (2013) Antisense oligonucleotide mediated therapy of spinal muscular atrophy. Transl Neurosci 4.

[29]. Mokri B, Engel A G (1975) Duchenne dystrophy: electron microscopic findings pointing to a basic or early abnormality in the plasma membrane of the muscle fiber. Neurology 25: 1111-1120.

[30]. Aartsma-Rus A, Janson A A, Kaman W E, Bremmer-Bout M, den Dunnen J T, et al. (2003) Therapeutic antisense-induced exon skipping in cultured muscle cells from six different DMD patients. Hum Mol Genet 12: 907-914.

[31]. Aartsma-Rus A, Janson A A, Kaman W E, Bremmer-Bout M, van Ommen G J, et al. (2004) Antisense-induced multiexon skipping for Duchenne muscular dystrophy makes more sense. Am J Hum Genet 74: 83-92.

[32]. van Deutekom J C, van Ommen G J (2003) Advances in Duchenne muscular dystrophy gene therapy. Nat Rev Genet 4: 774-783.

[33]. Goyenvalle A, Babbs A, Powell D, Kole R, Fletcher S, et al. (2010) Prevention of dystrophic pathology in severely affected dystrophin/utrophin-deficient mice by morpholino-oligomer-mediated exon-skipping. Mol Ther 18: 198-205.

[34]. Goemans N M, Tulinius M, van den Akker J T, Burm B E, Ekhart P F, et al. (2011) Systemic administration of PRO051 in Duchenne's muscular dystrophy. N Engl J Med 364: 1513-1522.

[35]. Cirak S, Arechavala-Gomeza V, Guglieri M, Feng L, Torelli S, et al. (2011) Exon skipping and dystrophin restoration in patients with Duchenne muscular dystrophy after systemic phosphorodiamidate morpholino oligomer treatment: an open-label, phase 2, dose-escalation study. Lancet 378: 595-605.

[36]. Adams A M, Harding P L, Iversen P L, Coleman C, Fletcher S, et al. (2007) Antisense oligonucleotide induced exon skipping and the dystrophin gene transcript: cocktails and chemistries. BMC Mol Biol 8: 57.

[37]. Shi S, Cai J, de Gorter D J, Sanchez-Duffhues G, Kemaladewi D U, et al. (2013) Antisense-oligonucleotide mediated exon skipping in activin-receptor-like kinase 2: inhibiting the receptor that is overactive in fibrodysplasia ossificans progressiva. PLoS One 8: e69096.

[38]. Rusten T E, Filimonenko M, Rodahl L M, Stenmark H, Simonsen A (2007) ESCRTing autophagic clearance of aggregating proteins. Autophagy 4.

[39]. Moscat J, Diaz-Meco M T (2009) p$^{62}$ at the crossroads of autophagy, apoptosis, and cancer. Cell 137: 1001-1004.

[40]. DeLaBarre B, Christianson J C, Kopito R R, Brunger A T (2006) Central pore residues mediate the p97/VCP activity required for ERAD. Mol Cell 22: 451-462.

[41]. Weihl C C, Dalal S, Pestronk A, Hanson P I (2006) Inclusion body myopathy-associated mutations in p97/VCP impair endoplasmic reticulum-associated degradation. Hum Mol Genet 15: 189-199.

[42]. Wong E, Cuervo A M Autophagy gone awry in neurodegenerative diseases. Nat Neurosci 13: 805-811.

[43]. Komatsu M, Kominami E, Tanaka K (2006) Autophagy and neurodegeneration. Autophagy 2: 315-317.

[44]. Malicdan M C, Nishino I (2012) Autophagy in lysosomal myopathies. Brain Pathol 22: 82-88.

[45]. Levine B, Kroemer G (2008) Autophagy in the pathogenesis of disease. Cell 132: 27-42.

[46]. Tung Y T, Wang B J, Hu M K, Hsu W M, Lee H, et al. (2012) Autophagy: a double-edged sword in Alzheimer's disease. J Biosci 37: 157-165.

[47]. Tresse E, Salomons F A, Vesa J, Bott L C, Kimonis V, et al. (2010) VCP/p97 is essential for maturation of ubiquitin-containing autophagosomes and this function is impaired by mutations that cause IBMPFD. Autophagy 6: 217-227.

[48]. Vesa J, Su H, Watts G D, Krause S, Walter M C, et al. (2009) Valosin containing protein associated inclusion body myopathy: abnormal vacuolization, autophagy and cell fusion in myoblasts. Neuromuscul Disord 19: 766-772.

[49]. Kim N C, Tresse E, Kolaitis R M, Molliex A, Thomas R E, et al. (2013) VCP Is Essential for Mitochondrial Quality Control by PINK1/Parkin and this Function Is Impaired by VCP Mutations. Neuron.

[50]. Yokota T, Nakamura A, Nagata T, Saito T, Kobayashi M, et al. (2012) Extensive and prolonged restoration of dystrophin expression with vivo-morpholino-mediated multiple exon skipping in dystrophic dogs. Nucleic Acid Ther 22: 306-315.

[51]. Cartegni L, Wang J, Zhu Z, Zhang M Q, Krainer A R (2003) ESEfinder: A web resource to identify exonic splicing enhancers. Nucleic Acids Res 31: 3568-3571.

[52]. Harding P L, Fall A M, Honeyman K, Fletcher S, Wilton S D (2007) The influence of antisense oligonucleotide length on dystrophin exon skipping. Mol Ther 15: 157-166.

[53]. Wang M, Wu B, Lu P, Cloer C, Tucker J D, et al. (2013) Polyethylenimine-modified Pluronics (PCMs) Improve Morpholino Oligomer Delivery in Cell Culture and Dystrophic mdx Mice. Mol Ther 21: 210-216.

[54]. Jenkins W J, Peters T J (1978) Mitochondrial enzyme activities in liver biopsies from patients with alcoholic liver disease. Gut 19: 341-344.

[55]. Yin H Z, Nalbandian A, Hsu C I, Li S, Llewellyn K J, et al. (2012) Slow development of ALS-like spinal cord pathology in mutant valosin-containing protein gene knock-in mice. Cell Death Dis 3: e374.

---

INFORMAL SEQUENCE LISTING

VCPEx5A (−14+11): SEQ ID NO: 1: AAA AAU GUC UCC UGC GAG AGC AAA C

VCPEx5A (+1+25): SEQ ID NO: 2: CCA CCA UGG ACA AGA AAA AUG UCU C

VCPEx5A (+15+36): SEQ ID NO: 3: CAG CAC GCA UCC CAC CAU GGA C

INFORMAL SEQUENCE LISTING

VCPEx5A (+76+100): SEQ ID NO: 4: AUC ACU GUG UCU GGA GCA ACA AUG C

VCPEx5A (+103+128): SEQ ID NO: 5: UCG UUU GAU AGG CUC CCC UUC GCA G

VCPEx5A (+7-18): SEQ ID NO: 6: AUC AGG GAG AAA ACU CAC CUC UCG U

VCP gene: SEQ ID NO: 7:
TTTCATATTTATCTCGTCTGCCTACTACATATACTTGCGTGGGAAGGCTT
GTGACCGTCTAGTTGAGTGCTAGTTGTCTATGATGCCCTTTCCTGACATC
GTCTACCTTATGAACTTGAAGTCTGGGTATGAGGAAAGGGCTACAGGAAT
CCTCACTTTGGAGGCAGTGGCTTTAGTCCTTCACATTGCCTGAATGCAGA
GCCCCAAAGCCCAGGACAGTGACAATGAGTGGAGTTGGGTCTGAAGGGTG
GTCTAGATAGGCCTCTCAGGACAAGGGCAGGTACCTGTTACTTAGAGACA
GGCAGGTTTCTCTCAGAGTAACTCTTCACTCCCTTCCTAATTCCAAATTC
TAGAAATTCGACTCGTCTTAGTCAAATGTGTCTGTGTGGGTACAGGGTGA
AAGGTGAATTGAGTCAGCATATCACCAACAGCTGCCTGTTGACTACTAAC
AGGGACCCCTGTTATTTGGGGCCCAAGGATTTTCAAGTCCCAGCATATGC
AGTTTTCTTGCTAATTTGGGTTCTACTGAATTGGCTGTGTGTTCTGTGGT
TGCCCTTTGACTTCTCTGGATTTGAGTGCCTTATTATAAGGTATTAATAT
TAATGACGGGAGGAAGAAAGGCACAAGCGCTGAGAAACTGCAAAGGCTGT
GGGATTGGGGTTACCAGAGGGTGCAGTGACAATGGGGTAGGAGTGGGGTG
CTAGTCAGAAAGTTCAGAGTAGGGGTGGTTGGAGGCAGCGTTGAGAAGGA
GCAAGAAGTGTCAGGGTGGTGATGGCGTCTTAGAAGATCTCCAGGTTTTG
GGAGAAGATGGGTGTATGGGTTACCACAATAGGACTAGACTAATACAAGG
GTTCAGTCTATTGTGCCACGTTCTTCCAGGAGGATAAACTCCGGAGCCAA
TGAACTGGAGCAAGTGGGAGAGTCCGCCTCTAAGGGATTAAAGGGCTC
CTTTCACTAATCGATCTCGCCCTATTCCTTTCGTTGATTGGCTGAGAATT
CCAATCCGTCGAGGAAGCGTAGCGTTGCGGCCAATTGACGTGGCGTTACT
AGGCGTGTCGCATCACTGAGGCGGGAGCCAGGCCGCAAGCGAATTTCCTG
ATTGGCTGTGATCTGCGGGTTGCTGGGGAGAGGCGCGGAGAGGCGGGCGA
GAGTCCGCAGGGCAGGCGCTGATTGGCTGAGGTGGGAGCAGCTTCCCTTC
CGATGATTCGGCTCTTCTCGGCTCAGCGAAGCGTCTGCGACCGT
CGTTTGAGTCGTCGCTGCCGCTGCCGCTGCCACTGCCACTGCCACCTCGC
GGATCAGGAGCCAGCGTTGTTCGCCGACGCCTCGCTGCCGGTGGGAGGA
AGCGAGAGGGAAGCCGCTTGCGGGTTTGTCGCCGCTGCTCGCCCACCGCC
TGGAAGAGCCGAGCCCCGGCCCAGTCGGTCGCTTGCCACCGCTCGTAGCC
GTTACCCGCGGGCCGCCACAGCCGCCGGCCGGGAGAGGCGCGCGCCATGG
CTTCTGGAGCCGAGTGAGTGTGCGCGCGCCGTTCGCTTGCTGCGGCGGCG
CGCACCGGGACCAGCCGCGCAGGGTAGGCCCGGCGGGGCCTGGCCGTGGG
CGCGTCAGAGAGGTGGAGACCAGGAAAGAGGGAAGGGAAGCTAGGGGGCG
AGTGAGGGGCCGTGGACCCGGCAGGCCCGGCTGGGGCCAGCTGCGCACCG
GCGCGCCCCCTAGGCGGGGCTTGCGTTGGGTCCGGGTCGGAGCTGGGCC
GGATCGTGCTGTGTCATGCAGGCCCCGGCCCGCCCGATTGGCTCCCTTAG
AACGGACGTCTGGGCCTGGCCAGGTCTTCCGGCCCACTCCGCCGGCGCGG
CGCCCCGGGGCTTTGGGGCGCCAGTCTGCCGTCCGGCCTACCACCCGCCG
AAAGCCTTTGGTCCCCGGAGAGAGCAGGCCCCGCGAGCCCGAGGCCCCAG
CCGGGCCCGGTGGGCGTGGACTTTGCGCCATGTGAAGGCCTCAGGAGCTC
TGCCACCGAGGCGGAGCCCGGGGTCGGGAAGGCCCGCCGAGCTCAGGGA
AGCTCACAGCCGCCTTTTTGGGACCCGGGTCCGCGGGGCCGGAGGTGGCA
TCCTCTGTGTGTGACCTGAGTCGTGAAGGACTGTTAGGGAGAGGGCGAGC
CCTACCTTTCGCTTCTGGTCTTCTTACTTTAGGCCTGTTGTTCATACTAG
AAAGTTTGAGCCAGTTTTCCTTAATGTTATGACTCGTGGGTGGGAGAAA
GGAATTTTCTTTAACATTTTAGGTTCTTGCTAAAGTTGGAATCTCAGTT
CGTGTTTTGTGCGCCTTTCCAGATTTCCAGGTTTCGTGGTGTGCAGTTTA
GAGTTGCACTAACTCTTCAAAAACACAAACGTGCGCGCACTCCTTTCCCC
AACCAGCTATATTGAGAAATTACCCGGGCTCTGGGCTTTCTGACCCCAC
CTCCATCCTTAGGAAAGCGTTAGATAAAACTTGGCTACCTCAGCCCATTC
AATTTAGAATAGAGAGCTTTTAGAGGCAAAAAAAAAAAAAAAAAAAAAAA
AAAAAACACAGCCAGCCCAAGGAAACTCTATGCAAATTACCTTCCTTCCT
TGAAGAGATTAGTTTTTTGAGGTGTGTTCCTTTTTCTCAAGTTTCTGAAT
TCGGATAAAGTATTACTCAGTTGCTTATTTAAAGAGTCACTTATTCTGA
AAGTATTCTTTTGGTTTATATGCAGTCGTCTCTTATTTTCAAAAGTAAA
AATCTAAAATTCTTGGAACCTGGCATCATCAGCTGTTTCTAACCTCTTGG
TCACCTTGATGACTCTTAGCTGAAACCCTTCCAAGTCCCGTGGAGTCCCC
TGTGCAGTTCTGGAAAGGGATTGACTTATACAGAAGACAATGGAGGATTG
CCCCAAAGAGTGTCCAGAACTGCTGTTGGCCCATGGTCAGGCCAAATTCA
GTCTTTTAGAGATTACCACATCTGATCTCAGTAGGTAGATGGGAATTAG
AGGCTTTACCTTAAGAAAAGGCATACACACTCATCTCCAGAGCAGAGTC
CGGGATGGTAGGCAGAATGGAGGTTTTCCTAGGATACAGCTTTGAGATTA
AAATACAAACTATTGACCGGGCACAGTGGCTCAGGCCTGTAATCCCAGCA
TTTTGGGAGGCCGAGGCAGGCAGATGCACTTGAGGTCAGGAGTTTGAGACC
AGCCCGGGCAACATGGAGAAACCCCATCTCTATTAAAATGCAAAAGTAG
CCAGGCATGGTGATGGTGCACACCTGTAGTCCCAGCCACTCTGGAGGCTG
AGACAGGAGAATCACTTGAACCCAGGGAGGCAGAGATTGCAGTGAGGGAG
ATCGCGCCACTGCACTCCAGCCTGGGCAACAGAGGGAGACTCCGTTTCAA
AAAATAAAAACTATGGTGACTAGAGGCATCTGGCGTTTATTTTTCTCC
AGTCCCAGTTCTATAAGTCAAGCAAGAAGATGGGCAGTCCCTGGAAGAGT
ATTTTGATGGGACAGGAGTGGGAGAGCTCGTGGGTTTACATTGCTCTCAA
CTGTCACATTGAGCATGCTTGGCCTCTAGTGTGTTGATAAGCATTGGAAG
AGTCTGCCTACTCAGCAGCATTGTGCCTGGAGTGGCAGACTTTTGGAATG
GGGGAAGCAAATTTGAGCAGAGGAAACTGTCGTTAGAAACTAGTTTAGAG
GCAGTGGTTAAAAATGCAGCCTATGTGTGAGGGTTAGCAGAAGGCCTACC
ATTTTGTTAGATGAATGGGGTTTGTTTTTCTCTTGGGTGTATCAGGACCC
AAAGATGTAAGAACCCCATGGCTTCCTAGCTGAGCACAGCATTTTTCTTT
GTCTCTTGCAAATTGTGAGGATATTTCCAATGGGAATACTATTTTGTCTT
GTTTTGTTGACTTCAGTATCCCCAGCCCTTAGAACAATGCCTGGTACATA
ATAGAGACTCATGAATTTGTTGAATGAAGAAATTCGTTTTAAAAATTTAT
TTTCTTTGCTTCCTTCATTGTCTGGCCTTCCTACTTTGGTTAATGCTTAT
GTTTTCCTGAGCCTTACTAACACGAGGCCGCTCTTAAAAAAGAGAGAGCC
CTGGGTGCTGTGGCTCACGCCTGTAATCCCAGTACTTTGGGAGGCCGAGG
TGGGCAGATCACCTGAGGTCAGGAGTTCGAGACCAGCCTGACCACCATGG
TGAAACCCCATCTCTAGTAAAAATGCAAAATTAGCCAGGTGTGGTGGCGC
ATGCCTGTAATCCCAGCTACTCGGGAGGCTGAGGCAGGAGAATCACTTGA
ACCCGGGAGGTGGAGGTTGCAGTTAGCTGAGATCGCAGCATTGCATTCCA
GCCTGGACAACAAAAGCGAAACTCCATCTCAAAAAAAAAAAAAAAAAAAA
AAAAAGGGAGAGGGAGCTTGCTGAGTCTAGTAAGTGACAGCTGGAAACGG
GCTAGGTAATAAGTTGGTGTCACTGTCTGGTGAATGATCCTAGCTTCTAG
GAAATAACACTGAGTGTAGACCCAGTCGACTTTGATTTGGGTGAGAGGGA
TTTGGATTTGCCCCATGTCTCAGCATTTCTTGGTTTTGATTTTTTGAGCC
AACTTTATGGAATTGTGTACTTTTGCAGATATTACTGTGAAGTTCCTTTT
GACCTTGAGCCTCTTTCTGGCGGTTTGATGTCTGTTAGTGTTTTTTCCAA
ATATGATGGCTCTTTATGCTTGGCATTCCTTTGGTACTATGAATGCCCTG
GCATCAGTAGGTTTAGCCTATAAGGAGGGTAGCACCAATGATTCTGCTTC
GTTGTCCCCAGGCTTGCTTGGTAGAACTTAAGGCCTCCCTGAGCCTCAAG
GGAGGTTGTCTGGCTTACTTAATTCCCTGGAAAGTTAGCTTATGCTTTAC
TCTATACTGTTAATCATGGTGACCATTAATACCATGTGCCAGGTATTATG
TTAAGCATTTTACATTCATTATCTCCCTTAAGACAATAAGCCTCTGAGAT
AAGTATTATATTCCTTCTTTTATAGAGGAGGACATCAAAGTTCAGAGGTT
AGGTAACTTGCCCAAGATCACAATTAAGCAGTGCATAATTGGAATTCAG
ACCCAATGGGTCTGACTATAGAGTTCCTGCTCTTAACCACTCTTCTGTAA
GTCTAAGACTATTTTTATTTCTCTAACAACTATTCAGCCTCCATTTCTAT
TATGTCTTCTTCTTAGGCCATTATTTTCTGACCCTGGGGCAGGATCACTC
ACTTGGGGCTTATAGCTGGGACACTGACGCTCAAAATACCAGGAGCTGC
TGGAATGGGTATTGTAATATGTATGGTAGATACTGCTCCTCGTGACCTTG
GCTGCCTTTCCTTCATCTGAGCTTTCTGGTCTAGGGACAGCTTCATCTAT
TCACTGTTTCTTTCCTAAGTATGAGTTTTAGAGACTGGCGAGGCGCTTGG
GGCAGGAGTATCTACTGACTCCATTTCCTCCTTCTAGTTCAAAAGGTGAT
GACCTATCAACAGCCATTCTCAAACAGAAGAACCGTCCCAATCGGTTAAT
TGTTGATGAAGCCATCAATGAGGACAACAGTGTGGTGTCCTTGTCCCAGG
TAAGCTGTGGCCACAGACTAGTCTTTCCTTACTGCACTTACTTGAGGGAT
TTTCCCAGGTTTCTTTTCATTTTTCTTGCAGTGACTGCAGATAGAGTG
GGGTTTACTGGGAATCCAATCTCCAGGGCTGCTGCTTACTCCCCGTCAG
CCCAATGACCCAAAGGCCTTAACTTTCTTTCCTCAGCCCAAGATGGATGA
ATTGCAGTTGTTCCGAGGTGACACAGTGTTGCTGAAAGGAAAGAAGAGAC
GAGAAGCTGTTTGCATCGTCCTTTCTGATGATACTTGTTCTGATGAGAAG
ATTCGGATAATAGAGTTGTCGGAATAACCTTCGTGTACGCCTAGGGGA
TGTCATCAGGTGTGTGTGGGGTTTTTGGCTTCACAGGGATGGGAGGCCAG
AGATAGCCTGCATTACAGGCAGGACCCATGTATTACAGGCAGGACCAAGT
TCTTGGCACCTGTCGATGCAGGAAGCCTCCTGGTCATGGGAAGACTTATG
CTTCAGGGTTGCTTTTAGGTTTTGGTTCTGCCTCCCTGGGACTTCAAAT
CCATTTCTGCAGGTCCCTTGAGACAAATTGGCGTTCCTGTAACTTTCTTG
ATGGCTTTATTTTTCCTACTAGAGGTGTAATTTATCATACTTATATCCT
GGCTTAGGATACCACTCGAGGGTGTGTATGTATATGCCAAATAATCTCCT
CACTACTCTCACTAGTATGTCTAATTGATGGCTTGTGTTGGGGTTGGAAT
GAGGTGGGGGTATGGGCATGGAAGGTGAGCTGCTGCAGGTCTTTTAAGC
CCCTAAGTTAACCCGGGAGAGAGGAATAGTTGGAGCCAGACCTGGGATAG
CTCTCAATGTGAGTGATTTTGCTTGTTCTTGCATAATTTTAGGCAAGAGG
TTACCCCATCTTGGAGTCATCTCTAGCCACTCCTACCCAACCAACCATCA
CCTGGCCAGGATCATCTCAGGCTTTTCATTCTTTTTGAAGGATGCTAAGT
TTCATGTAGCTTTCTTCTTGGGAGTGCTTAGTCACTTCCTCAAGGTGTTC
TGACCACCTGGCTGAGATAATTTTGTTTTTTTCACTTCTGTTTCACTGAC
CCTGACAATTGTTAGCTTAAGACCTTCCCTTGTAATATTGGGTCACCAGT
ATTAGCTAGAAGGGGATCATCCTTGGATATCTCCCTGAAGACCCTGCATG
TCTTTGTGGGGTTTCTAAATGTGTGCTGTTTGATTTTGGCTCACTGATTA
GGAGTGAGTGGGGCTGTTCCTTCGCCCTCACTTCCACCCTGTTCTCCTTC
CTCTCCTTCGCCTAAAGCCATCCTGCCTTTTCTTTTTCACTTACTATCAGC
TATCTGTGCCAGGCCCTTTTGGACACCCAGTGCTTGGGCCCGAAGTGTGG
TTGGTAATATGGAGTCTGCTTGTCATCCTCAGCATCCAGCCATGCCCTGA
TGTGAAGTACGGCAAACGTATCCATGTGCTGCCCATTGATGACACAGTGG
AAGGCATTACTGGTAATCTCTTGAGGTATACCTTAAGCCGTACTTCCTG

INFORMAL SEQUENCE LISTING

```
GAAGCGTATCGACCCATCCGGAAAGGTGAGAGCTAATTCTGAGCTTAAGG
ATTATTGACTGTAGGGAATAAACCTTGGAACATCTTTATCTCATTTTCTT
TTTCTTTTTTTTTTTTAAATCTTTTATGCTTTTTCCCCTGTATTTATTTA
TTCATTTTTTAAGAGATGGGGTCAGCTGGGCACCGTGGCTCACACCTATA
ATCCCAGCAATTTGGGAGGCTGAGGCGGGTGGATCACTTGAGGCAGGAG
TTTGAGACCAGCCTGGCCAACATGGCGAAACCCCATCGTGGGCACCTGTA
ATCCCAGCTACCTGGGAGGCTGAGGCATGAGAATTGCTTGAACCCAAGAG
GTGGAGGTTGCAGTGAGCCAAGATTGGGCCACAGTACTGCAGCCTGGGTG
ACAGAGCAAGACTCTGTCTCAAAAAAAAAAAAAAAGAGACAGGGTCTCAC
TATGATGCCCAGGCTGGTCTCAAACTGCTGGGCTCAAGTGATCCATCTGC
CATGGCCTCCCAAAGTGCTGGGATTACAGGCATGAGCCATCAAGCCTAGT
CTCATTTTCTTTTCTTTTTTTTTGAGACAGAGTGTCGCGCTGTCCCCCA
GGCTGGAGCGCAGTGGTCAATCTCGGCTCACTGCAACCTCCGCCTCCTG
GGTTCAAGCAATTCTCCTGCCTCAGCCTCCCAAGTAGCTGGGATTACAGG
CGTCTGCCACCACGCCCGGCTAATTTTTGTGTTTTTAGTAGAGACGGGGT
TTCACCATGTTGGTCAGGCTCGTCTCGAACTCTTGACCTCAGGTGAGCCA
CTGTGCCCGGCCGCTAGACTCATTTTCATATATTTGTATACACACACATG
CAAACCCTGCACACATATTCATATGTCTTACCCTCTTTTTTTCCTCCATC
CTTCCTTTGCTCCATCTCTCCCCTTCTCTGTTCCAGGAGAGTAAGCTATC
TTTATGGATCTCTGAAGGAGAAAGTGGTCCATTTTGGCTGGGTCAGGGTC
CAGAGTGCACAGTTCTACCATTGGTGGTTGTAGTGAAAACTTGGGCTACC
TATATGGCAGAAGTCAGAACTTGATGGGCTTCTGACATGTCAGGTTTTGT
TCACTGACCTCTTGTCAGAGGGACTCTTCACAGTTTACCTTTCTCATCTT
GCCTGCTGCTTATTAAGACAGGTGGGGTGGAGTTGGGGAGAGGTAGGGCA
ATATCTAATGAAGGGCACTATCTAATGAGCTTGGCATTTTGACCCCAGGG
TCTGATGAGTTCTCACTTTGTCTTGTAGTTGACACCTCTAACTGTGCTTG
TACTGTTTGCTCTCGCAGGAGACATTTTTCTTGTCCGTGGTGGGATGCGT
GCTGTGGAGTTCAAAGTGGTGGAACAGATCCTAGCCCTTATTGCATTGT
TGCTCCAGACACAGTGATCCACTGCGAAGGGGAGCCTATCAAACGAGAGG
TGAGTTTTCTCCCTGATTCCAGTATCCGATTTTATGATTACTCAGTGTGG
CATCATGTGGTAACTGTCAGGACTGGGTGCTCGGCCGGCTGCGGTGGCTC
ACACCTGTAATCCCAGTACTTTGGGAGACTGAGATGGGCAGATCACTTGA
GGTCAGGTGTTCAAGACCAGCCTGGGCAACATGGTGAAATCCCATCTCTA
CTAAAAATACAAAAATTAGCCAGGCATGGTGGTACACATCTGTAATCCCA
GCTACTCAGGAGGCTGAGGCAGGAGAATCGGTTGAACCCAGGAGTCGGAG
GTTGCAGTGAGCTGAGATTGTGCCACTGCACTCCAGCCTGGGTGACAGAG
TGAGACTCTGTCTCAAAAAAGAAAAAGACTGGGTGTTCTTTGGAGAACTA
ACCATCTTTCAGGGATGAGAAACCTGCCAGCTATTCATTTCTGGGCCTAA
TTGTTTCTTGGATTTACCTAATGCCAGGAATTTCAAAAAACTAGACTGAA
CCCAAAATATATAAGTGATTGAAATCATTTTTGAAGTAAAGCTGATGGTG
GCTTCAGGCCTCTGCCCATTCCCAGGGTTTCCAGCTTCAGATTTTAGAGA
CCCCTTCTCAGTAAGACTACGAGTAATGTGAGAGGCAAGGACTGTGCTAG
AAATCTTTGCCTTGGGATTTTGTAGTTGTTCTTTGAGGCCGGATCCCTT
TAGAGGAGAATCTTTTTAAATTTAATTTAATTTTTAATGAGATGGAGTC
TTGCTGTATTGCCCAGGAACTCCTGGACTCAAGCATTCCTCCCACCTCTG
CCTCCCAAAGTGCTGGGATTACAGATGTGAGCCACCATGCCGGGTTGAGA
ATCTTCTTATACGGTAGGTTTTTGCACACTAGGTAGTGGAATGATTTAGA
GAAACTCAGCTTTTGCTGATATAATATTCTTGCCTTCTCCTTTCTTTATC
TCCTCCATATTCAGGATGAGGAAGAGTCCTTGAATGAAGTAGGGATGAT
GACATTGGTGGCTGCAGGAAGCAGCTAGCTCAGATAAAGGAGATGGTGGA
ACTGCCCCTGAGACATCCTGCCCTCTTTAAGGCAATTGGTGTGAAGGTGA
GCATCCTGGGCTCTGGAATCAAGTCTAAAGTGGTGCCAATGTCTAATCCT
GTCCCAATGTCTAATCCTGGGACTGTTTTCATGCATGGCTTTCATTATTG
CCTTGGATTAGAGGGGCAATAACGTATCCTTTAGTTTACCTAAGGCTCTA
AATTCATTAGAGCTGATGGTCTAAAACCAGATAGGCTAATCAAATTGTC
TGTTGTGTGCGTGTGCGCACAAAACACACACACATATATATATGGGTTT
TCTTTACAACTCTTAGAATATAAAAGCCATTCTTGTATCAATAGACCCTG
TAAAAACAAATCTCACCATAGTTTGCCAGCCTGTCTAGAGCAATGTCACC
CAGTAGAAGTAAGGAAGTTAAGGAAATTTTCAGAGTGTTAAAGGGTTCTG
AGTCTAAAACATTTGAGAACTATTGGTCTAGAGTGTAGCTTCTCAATCTT
TTCCTAGTGGGAAAGTGTTTCCATGGAACACACTGAAGATGAAGTTACTC
ATTTTCCTAGTGGGTGGCACACAAATAATTTCATTTTCTATGTGGACAGT
TTACATGTTCTGCTTGTGGATGAGGCCATAGAAAGGGTAGTGTTGAAGAA
GAAAAATGATGATTGTAAGGAACAGCATTCCAGTGTGATAAATTCTGGAG
GGCATGATTACTGGAGTGAGTGATCCTCTGGCAATGAAGAAAATAGACCC
TGCTCTCTTAAATGGCTTAGCTAGTCTTTGGCCCTTGGTCTGTCTAAAAT
TGAGCCCTTAGTGTAATGGCCTCTTGCCTTTCCCTAGTCATGTATCTTCA
AACGCATTTGGACTACAGTTTCTCTGCCCTTAGTCTCCTATGCAAGTTGC
AATCATAAATGTTGCCCACTTTCTAGCAGTATTTTCCCTGCTAGTAATAG
AAATGAGTGTGGCCTAAAGTAATTGTCTTCTTAGCATTTACTGCGGAGGG
CTTATTCTAGATTCTGCAGGGTTGAAGCCTGATTCTCACCCTCTCTGGA
GCGCTAGTCAAGCCATTTTAGGGTTTGGGAGAAGGTGGGAACCTAATCAC
ACTCTGCATTGGTCCACAGCCTCCTAGAGGAATCCTGCTTTACGGACCTC
CTGGAACAGGAAAGACCCTGATTGCTCGAGCTGTAGCAAATGAGACTGGA
GCCTTCTTCTTCTTGATCAATGGTGAGATATTTGGTTCATCTTATGTCTA
GCTAGACCCAATTTTGAACTGGGCTTATGAGCTGGAGCACTTATGAACAC
ATCCTTTTTGCACCCATGCCCTCCTTCATGTTTATAGCATATTTCTTATG
CTGGGGTATGTTACAGACAGAAGAGCAATAAAGGGAAGATATTTTACATT
GGTGCTCCCTGTCCTGCCCCCTTTGAGAAAGATTGTGGACAGACTGCAGA
GCGGGAGCAAGCTAGAATGAGAAATCAAAGGGTGAATGGTTAGTGATTTG
AGAGGGTTTGGGGCAAATGAACTTTGATCACTGGCTCTTGGAGAATGCTG
TTTAGTGGTGTGCCATCTGGTGTGCCATCTCTCTTGCTCTAGCCAGAGGT
CCTAGAGCATTTGCTGTCACCTTTACAGTTCAACTGTGAGAAGAGTATAG
TGAGTCCCTGGGCTTCTCTCCAGCCTTGCCTGGTGGCTGTCCTGGGATAA
TGGCTGGTAGAGGATGTGAGAAGTAGGCAGAGGTTACCACCTTCTCACCC
AGGACCTGTCTCTGGGCCAAACAAGCAAGATAACTGATTTTTGGGAGGAA
TTGGGAAAGACTATCATTTTGTTATTGTCTCCATTCTGTATCCTTTCAGG
TCCTGAGATCATGAGCAAATTGGCTGGTGAGTCTGAGAGCAACCTTCGTA
AAGCCTTTGAGGAGGCTGAGAAGAATGCTCCTGCCATCATCTTCATTGAT
GAGCTAGATGCCATCGCTCCCAAAAGAGAGAAAGTAGGAGCTTACCTGAG
GGGATAGAGGGGGGTTGAAAGGCCCTGACTTCACTTCTGACCAGACATCC
TGTTCTGGCAGACTCATGGCGAGGTGGAGCGGCGGCGCATTGTATCACAGTTG
TTGACCCTCATGGATGGCCTAAAGCAGAGGGCACATGTGATTGTTATGGC
AGCAACCAACAGACCCAACAGCATTGACCCAGCTCTACGGCGATTTGGTA
AGGACTCCAGATACTTTTGACCCCGTCCTTGCTTAGGTCCTACTTCTCTC
CTTCATCTAAGTCACCTAATCCTCTTGAAGCCCTTCACAGTGATTGGGTC
CAGGGGTCTTTTTCCTTTACCCTACGTCCTGTCTAGAGTGACCAACCACC
CTGGTTTTCCTGACTGAAAGGTTTCCCAGAGCTTGAGACTTTTTTAGT
GCTGGCATTAGGACAATCCTGTCTGGCTGAGATGGTTGGTCACCCTAGG
CCTGTCTCTTACCTCTGGACTAGAGATGAGCCCTGTTTATGTTTGTGTAC
TGTCCCACAGGTCGCTTTGACAGGGAGGTAGATATTGGAATTCCTGATGC
TACAGGACGCTTAGAGATTCTTCAGATCCATACCAAGAACATGAAGCTGG
CAGATGATGTGGACCTGGAACAGGTGAAGTGATGATGATGGCTGACCAGG
CGTTACAGTGTCTCTAGGCAGTTGCTGGGAACTGGCTAGAGACATAAGGT
TAAGATGTGAGGAGATGGGTTTTGATTTCTGGACAGGGGAAAGGAAGTAA
TCTGAGATTGAATCCAGGAAATGGGAGTTGGCATTTTTCATAGTTGACGC
TGCATTTAGAGTAAATCAGAATTGTTGGAGCAGCCTTATTTCTAGGTCCC
AAGTCCAGAATTAAGTACTTAAAACCCAGCCCATAAAGGTATTGATAGTA
TATATTCAAGGAAATGAAGATGAGGACCCAGGGATAGCAGTCAGGGAGGATT
CTATTGTCTCTGAGCCTCCTGCAGCAGCTGGGTCTTTGAGGCAGCATAGT
AAGTAGATCTTTCTCTGCAGGTAGCCAATGAGACTCACGGGCATGTGGGT
GCTGACTTAGCAGCCCTGTGCTCAGAGGCTGCTCTGCAAGCCATCCGCAA
GAAGATGGATCTCATTGACCTCAGGAGGATGAGACCATTGATGCCGAGGTCA
TGAACTCTCTAGCAGTTACTATGGATGACTTCCGGGTAAGGACCACACCC
GTGCCTCAGGTACACACATACGTGCTTTGACCCCTCCCTTGATAAGTCTC
ATCCCCAGTTTTCCCTCCTTTTCTAGTGGGACCTTGAGCCAGAGTAACCCA
TCAGCACTGCGGGAACCGTGGTAGAGGTGCCACAGGTAACCTGGGAAGA
CATCGGGGGCCTAGAGGATGTCAAACGTGAGCTACAGGAGCTGGTCCAGG
TAGGGCAACTTGGTCCAGGGTGAGTCACTGTCTCAGTACATTGTAATTGA
TCTGGGTGATCTCAGGGTGTCAACACATTTGCTGCAAGAGTTGTGAGAGC
ACGACTTAGGAACCTACTGTTCTTAGGGTTGAGGCACTAAGGAGTCTTCT
TCTAGAGAACCTGGATCTGATACCATTGGGTACACCATGAAATAATGGAG
GGGATGCTTCTGTTTAGTTAGGTTCTTTCAAAATGTGGAGGTAGCCTTG
AACCCTCTTTCCTTTTCCTCCTAGTATCCTGTGGAGCACCCAGACAAATT
CCTGAAGTTTGGCATGACACCTTCCAAGGGAGTTCTGTTCTATGGACCTC
CTGGCTGTGGGAAAACTTTGTTGGCCAAAGCCATTGCTAATGAATGCCAG
GCCAACTTCATCTCCATCAAGGGGTCCTGAGCTGCTCACCATGTGGTTGG
GGAGTCGAGGCCAATGTCAGAGAAATCTTTGACAAGGTGAGCTACAATA
GGCTGAACTATGTATTGATTTGCCTGAGGGCAAGGAATAGAGGCTGTTTT
TCTTTAAGAGGGTTGAAATATTCTTAGTGCTGGCTGCTCAACTGCACAGT
AAGTCACTTGATTTTCTTTCTGAGGTCTGAGAGACCCAGTAGTGTTATTTTT
TTTTCTCTCTCTCTCTTGAGACAGGGTCTGGCTCTGTTGCCCAGGTTG
GAGGGCAGTGGTACAGTCATGGCTCACTGTAACCTTGAAACCTGGGCTTA
AGCAATTCTCCTACTTCAGCCTCCTGAGTAGCTGGGACTATAGGCATGCG
TCACCACATCTGGCTAATTTTTATTTTTTGTAGAGACAAAGTCTCAGTA
TGTTGCCCATGCTGGTTTCGGATTTCTGGCCTCAAGTGATCCTCCCACCT
TGGCCTCCCAAAGTGCTGGGAATACAGGTGTGAGCCACCACGTTTGCCTA
GAGACATCTAGTTTTGTTAGTGCTTGAATCAATCCATTCCTCCTACAGGC
CCGCCAAGCTGCCCCCTGCTGTGCTATTCTTTGATGAGCTGGATTCGATTG
CCAAGGCTCGTGGAGGTAACATTGGAGATGGTGGTGGGGCTGCTGACCGA
GTCATCAACCAGATCCTGACAGAAATGGATGGCATGTCCACAAAAAAAAA
TGTGTTCATCATTGGCGCTACCAACCGGCCTGACATCATTGATCCTGCCA
TCCTCAGACCTGGCCGTCTTGATCAGCTCATCTACATCCCACTTCCTGAT
GAGAAGTCCCCGTGTTGCCATCCTCAAGGCTAACCTGCGCAAGTCCCAGT
TGCCAAGGCAGGTCAAGATCATGGGCTGTGGGAGACTTGCATGAGTCCT
CAGGCTGGTACGGAGTGCTCTTTAGTTTCTGGACAAGATTCCACTGGGGT
TAGGGTTGGTCTAAAGGGAAGGTAGAATTTTGAGGGATATCAAGATAATC
TAGAATCAGGAATAAAATGGGTGCCAAAGAAGGGGCAAACTGTAGTTG
GGAGTGCTCGGTAGCCCAAAGATCTGCGTATCTCGAGAGGAGAGGCTAA
ATGCTAAGGTACCTCTGCTGCTGCTTTTAGGATGTGGACTTGGAGTTCCT
GGCTAAATGACTAATGGCTTCTCTGGAGCTGACCTGACAGAGATTTGCC
AGCGTGCTTGCAAGCTGGCCATCCGTGAATCCATCGAGAGTGAGATTAGG
CGAGAACGAGAGAGGCAGACAAACCCATCAGCCATGGTGAGTCTGCATCC
TTTCCCCAGATGTGCCAATCATGGAGAGCCAGGCAGCAGCCACCACCATG
```

INFORMAL SEQUENCE LISTING

CCCTGGAGTTGAGAGTAGAAGCTGTTGGAAAGATCATCTAACTGAGAAGA
ATTTTAATAGGGCATCAAAGATAAAGAATGCTGAGGTGAATCCATTCAAT
TTGGAATAAGGCCGAGAAGAGATGGTCAGGCTCCATTCTCAGTCTGAACC
AAGCTCCATGAGGGAAATCAAAGTATGAGAGTGCAGCAAACACAGCAAGG
TTTTTTTTGTTTTTGTTTTTTGTTTTTTTTTGAGACGAAGTCTCACTC
TGTTGCCCAGACTGGAGTGCAGTGGCACGATCTTGGCTCACTGCAACTTC
TGCCTCCCAGGTTCAAGCGATTCTCCTGCCTCAGCCTCCCGAGTAGCTGG
GACTACAGGCACATGCCACCATGTCCGGCTAGTTTTTTGTATTTTTTTT
TAGTAGAAACGTGGTTTCACCACGTTAGCCAGGATGGTCTGATCTCCTG
ACCTTGTGATGTGCCCACCTCGGCCTCCCAAAGTGCTGGGATTACAGGCG
TGAACCACAGAGCAAGGTTTTGAGCTGAGATGAGACTCATATACTTATCC
CTGATGGTTGGGGAAGGGATAGGGTCCACAGACCTCCCAAAATGAAAAGG
CAAATTCATGTGTTTGTAAGTTCCATAAAGGTAAGATCTCTGTCATCTCA
CTTGTTTTCCACTATGTCTTGTGTTACCCTTAATTAATTCATTAAGTTCC
AAACATGGGACTTAATGAGCAAATAAATGCTTTCTTTCCCTTTTGAAGG
GTCTGTGACATCCCTTCTCTCTCCCATAAAAGCTTAACAACTACTGATGA
ACTAATCCTAGGAGGTAGTCACATAAGTCACAGAAATTGGCCTCTCAATG
GAAGAGATAGGTTTTGAGCTGGGCTGTGAAGAGAGTAGAATTTGAATAAA
GGGAATAAGCAGCCCAAATAATGTGCTCTAGTAGTAGGATTGCAATCATT
GGGAAACCCTGGGTAGATTTAAGAGTATATATGTCACTGGAAGTGAGACC
GCTAGGTAGGATGTAATCAAATGTGGTAAGCACTGAAAGCCATTGGCAT
TTCCTTTTAAAGTATTAAGGTTTATTAAGGTATGATATAAATACAATAAA
ATTCACTCTTTCTATATACCATTTCCATGCTTTATGACAAGTGTGTGTAA
GTTCTATAACTACTACCACAGTTGAGACTTAAAATTTCTACTATCTCAA
AAGTTTCCTTAGCCACTTCAGTCAACATCTCCCCTCCTTAAGCCCCATCA
CTGATGTGATTTCTGTCCCTACAGTTTTCCCTTTTCCAGAGTGCATTGAC
AAGTTTTTAAGCAGAGCAGTGACTCAATTTTAGGAAGCATGGCCTAGCAT
CTTACCTCAGGTTGGATTGGAAGGGCAAGGAGACCAATAAACTGCAGTAA
TGGGAGGCCTGGGATGAAATCCAGGCTGGGCTTTAACTAGCCCTAGTGAT
CTGTGTTTACCAACTATAGGAGGTAGAAGAGGATGATCCAGTGCCTGAGA
TCCGTCGAGATCACTTTGAAGAAGCCATGCGCTTTGCGCGCCGTTCTGTC
AGTGACAATGACATTCGGAAGTGATGAGATGTTTGCCCAGACCTTCAGA
GAGTCGGGGCTTTGGCAGCTTCAGGTAAGTTGGTTGGGAGCATTAGACAG
TGCTTAAGTTACTTTGGGGACCTACACCAAAAGGGATGGGAGTCCTAAGG
AAGCTAGAGGGGTAGTTGTGGAAATCTTACACAGGCCCTGTCCTAACCCT
CTTTTTTGGCTTTGCTCTTGTACACAGATTCCCTTCAGGGAACCAGGGTG
GAGCTGGCCCCAGTCAGGGCAGTGGAGGCGGCACAGGTGGCAGTGTATAC
ACAGAAGACAATGATGATGACCTGTATGCTAAGTGGTGGTGGCCAGCGT
GCAGTGAGCTGGCCTGCCTGGACCTTGTTCCCTGGGGTGGGGGCGCTTG
CCCAGGAGAGGGACCAGGGGTGCGCCCACAGCCTGCTCCATTCTCCAGTC
TGAACAGTTCAGCTACAGTCTGACTCTGGACAGGGGGTTTCTGTTGCAAA
AATACAAAACAAAAGCGATAAAATAAAAGCGATTTTCATTTGGTAGGCGG
AGAGTGAATTACCAACAGGGAATTGGGCCTTGGGCCTATGCCATTTCTGT
TGTAGTTTGGGGCAGTGCAGGGGACCTGTGTGGGGTGTGAACCAAGGCAC
TACTGCCACCTGCCACGTAAAGCATCTGCACTTGACTCAATGCTGCCCG
AGCCCTCCCTTCCCCCTATCCAACCTGGGTAGGTGGGTAGGGGCCACAGT
TGCTGGATGTTTATATAGAGTAGGTTGATTTATTTTTACATGCTTTTGA
GTTAATGTTGGAAAACTAATCACAAGCAGTTTCTAAACCAAAAAATGACA
TGTTGTAAAAGGACAATAAACGTTGGGTCAAAATGGAGCCTGAGTCCTGA
GCCCTGTGCCTGCTTCTTTTCCTGGGAACAGCCTTGGGCTACCCACCACT
CCCAAGGCATTCTTCCAAATGTGAAATCCTGGAAGTAAGATTGCACCTTC
TTCCTCTCCTGATCAACATCGGTATGATGTCTCCTGTTGCCTCACCCTTT
GTCTGCAGTATCACTGGATAGGACTGGTGGAAAGGGACAGCAGCCTGACAGA
GCTCCAAATGTGGAGAATATGGCATCCCTCCACCTATATTTGATGTGGAC
GGTAAGGCTAGGCCTGCAGGATCCCTTATCCTGACCAAAGACTGTGTTGG
GGTGCCATTTGAAAATCGCAGGGTTGCAAAAGAATACAATCTTACTTGCA
GGTGGATATTCTCTATACTCTCTTTTAATGCATCTAAAATCCAAACAT
CCCTGGTTGGTGATCACTTACAGTTGTGTCCACCTTTATTTATGTACT
TTGATTAAAAAAAAAAAACTTTTTGTTAATATAAATTTTAGTATTGAAT
TTTTTTTTTTCCAAACAGAAAATAGACTATCCTCTTCAACAGTAATCAC
TTAGTGCTTCTAGGGTCAGTACAGTCATGATGCCTTTACCCAGAGAGAGTAG
TGCAGAGAAAATAAATTACTAAATTAAATATATGTTGATTGGCTTTGGGA
CATAATCTCAAAAGACAGTCCTGAACACCGTAATTTTGAATAAATACTG
TAATCTCCAAAGATCAAAATCCCTAAAGTCTAAAATTCTGAAAATCACAA
TCCCAAAAGGTCAAAATCCCAAAATACAATTCTGGAAGAAATACTAAACA
TTCTTCGAAAATTTACTTACATTTTTAAAAGCGTATTTATTTGAGAAACA
ACACAACAGAACGTTTCATAGGCCACTACACAGTAAAATAGGGAATAGTA
ACATTTTTGCAAGATAAACACTCAGGTATACCAATGACAGTTGCACGGAT
ATAACGGTGATGAGCAGATGAAACATTCATAAAGAAATAGGTCAAAAGT
GAAATGTATAAATGCTTTGTCACTATGCTTGGTAATTGTGGGCACCCTAGC
TTTATATAACTGGTCATCTGTAATACTGTGACAGAA

VCP pre-mRNA SEQ ID NO: 8:
UUUCAUAUUUAUCUCGUCUGCCUACUACAUAUACUUGCGUGGGAAGGCUU
GUGACCGUCUAGUUGAGUGCUAGUUGCUAUGAUGCCCUUUCCUGACAUC
GUCUACCUUAUGAACUGAAGUCUGGGUAUGAGGAAAGGGCUACAGGAAU
CCUCACUUUGGAGGCAGUGGCUUUAGUCCUUCACAUUGCCUGAAUGCAGA GCCCCAAAGCCCAGGACAGUGACAAUGAGUGGAGUUGGGUCUGAAGGGUG
GUCUAGAUAGGCCUCUCAGGACAAGGGCAGGUACCUGUUACUUAGAGACA
GGCAGGUUUCUCUCAGAGUAACUCUUCACUCCCUUCCUAAUUCCAAAUUC
UAGAAAUUCGACUCGUCUUUAGUCAAAUGUGUCUGUGUGGGUACAGGGUGA
AAGGUGAAUUGAGUCAGCAUAUCACCAACAGCUGCCUGUUGACUACUAAC
AGGGACCCCUGUUAUUUGGGGCCCAAGGAUUUUCAAGUCCCAGCAUAUGC
AGUUUUCUUGCUAAUUUGGGGUUCUACUGAAUUGGCUGUGAAUGGCUGUGUGUUCUGUGGU
UGCCCUUUGACUUCUCUGGAUUUGAGUGCCUUAUUAUAAGGUAUUAAUAU
UAAUGACGGGAGGAAGAAAGGCCAAGCGCUGAGAAACUGCAAAGGCUGU
GGGAUUGGGGUUACCAGAGGGUGCAGUGACAAUGGGGUAGGAGUGGGGUG
CUAGUCAGAAAGUUCAGAGUAGGGGUGGUUGGAGGCAGCGUUGAGAAGGA
GCAAGAAGUGUCAGGGUGGUGAUGGCGUCUUAGAAGAUCUCCAGGUUUUG
GGAGAAGAUGGGUGUAUGGGUUACCACAAUAGGACUAGACUAAUACAAGG
GUUCAGUCUAUUGUGCCACGUUCUUCCAGGAGGAUAAACUCCGGAGCCAA
UGAACUGGAGCCAAGUGGGAGAGUCCGCCUCUAAAGGGAUUAAAGGGUCUC
CUUUCACUAAUCGAUCUCGCCCUAUUCCUUGUUGAUUGGCUGAGAAUU
CCAAUCCGUCGAGGAGCGUAGCGUUCGCGGCCAAUUGACGUGGCGUUACU
AGGCGUGUCGCAUCACUGAGGCGGGAGCCAGGCCGAAGCGAAUUUCCUG
AUUGGCUGUGAUCUGCGGGUUGCUGGGGAGAGGCGCGGAGAGGCGGGCGA
GAGUCCGCAGGGCAGGCGCUGAGGGGCUGAGGUGGGAGCAGCUUCCCUUC
CGAUGAUUCGGCUCUUCUCGGCUCAGUCUCAGCGAAGCGUCUGCGACCGU
CGUUUGAGUCGUCGCUGCCGCUGCCGCUGCCACUGCCACUGCCACCUCGC
GGAUCAGGAGCCAGCGUUGUUCGCCCGACGCCUCGCUGCCGGUGGGAGGA
AGCGAGGGAGGACCGCUUGCGGGUUGUCGCCGCUGCUGCCCACCGCC
UGGAAGAGCCGAGCCCCGCCAGUCGGGCGCUUGCCACCGCUCGUAGCC
GUUACCCGGGCCGCCACAGCCGCCGGCCGGGAGAGGCGCGCGCCAUGG
CUUCUGGAGCCGAGUGAGUGUGCGCGCGCCGUUCGCUUGCUGCGGCGGCG
CGCACCGGGACCAGCCGCGCAGGGUAGGCCCGGCGGGCGCUGGCCGUGGG
CGCGUCAGAGAGGUGGAGACCAGGAGAGGGAGGGAGGGAAGCUAGGGCG
AGUGAGGGGCCGUGGACCCGGCAGGCCCGGCUGGGGCCAGCUGCGCACCC
GCGCGCCCCUAGGCGGGGCUUGCGUUGGGUCCGGGUCGGAGCCUGGGCC
GGAGUGUCGUGGUCUGACAGGCCCCGCCCGCCUGAGGCUCCCUUAG
AACGGACGUCUGGGCCUGGCCAGGCUUCCCGCCCCACUCCGCCGGCGCGG
CGCCCCGGGCUUUGGGCGCCAGUCUGCCGUCCGGCCUACCACCCGCCG
AAAGCCUUUGGUCCCCGGAGAGAGCCAGGCCCCGCGAGCCCGAGGCCCAG
CCCGGGCCCGGUGGGCGUGGACUUUGCGCCAUGUGAAGGCCUCAGGAGCUC
UGCCACCGAGGCGGAGCCCGGGGGUGGGGAAGGCCCGCCGAGCUCAGGGA
AGCUCACAGCCGCUUUUUGGAGCCGGGUCGGCGGGGCGGAGGUGGGCA
UCCUCUGUGUGUGACCUGAGUCGUGAAGGACUGUUAGGGAGAGGGCGAGC
CCUACCUUCCGCUUCUGGGUCUUCUUACUUAGGCCUGUUGGGUUCAUACUAG
AAAGUUUGAGCCAGUUUUCCUUAAUGUUAUGACUCGUGGGUGGGGGAGAAA
GGAAUUUUUCUUUAACAUUUUAGGUUCUUGCUAAAGUUGGAAUCUCAGUU
CGUGUUUUGUGCGCCUUUCCAGAUUUCCAGGUUUCGUGGUGUGCAGUUUA
GAGUUGCACUAACUCUUCAAAAACACAAACGUGCGCACUCCUUUCCCC
AACCAGCUAUAUUUGAAAAAUUACCCGGCUCUGGGCUUUCUGACCCCAC
CUCCAUCCUUAGGAAAGCGUUAGAUAAAACUUGGCUACCUCAGCCCAUUC
AAUUUAGAAUAGAGAGCUUUAGAGGCAAAAAAAAAAAAAAAAAAAA
AAAAAACACAGCCAGCCCAAGGAAACUCUAUGCAAAUUACCUUCCUUCCU
UGAAGAAGUAGAUGUUUUUGGAGUGCCCUUUUUCUCAAGUGUCAUGAAU
UCGGAUAAAGUAUAUCUCAGUUGCUUAUUUAAAAGAGUCACUUAUUCUGA
AAGUAUUCUUUUGGUUUAUAUGCAGUCAGCCUCUUAUUUUCAAAAGUAAA
AAUCUAAAAUUCUUGGAACCUGGCAUCAUCAGCUGUUUCUAACCUCUUGG
UCACCUUGAUGACUCUUAGCUGAAACCCUUCCAAGUCCCGUGGAGUCCCC
UGUGCAGUUCUGGAAAGGGAUUGCUUAAUACAGAAGACAAUCGGAGGAUUG
CCCCAAAGAGUGUCCAGAACUGCUGUUGACCAUGGUCAGGCCAAAUUCA
GUCUUUUAGAGAUUACCACAUCUGAUCUCAGUAGGUAGAUGGGGAAUUAG
AGGCUUACUUAAAAAAGGCAACUACUCAUCUCCAGAGCCAGAGUC
CGGGAUGGUAGGCAGAAUGGAGGUUUUCCUAGGAUACAGCUUUGAGAUUA
AAAUACAAACUAUUGACCGGGCACAGUGGCUCAGGCCUGUAAUCCCAGCA
UUUUGGGAGGCCGAGGCAGGCAGAUCACUUGAGGUCAGGAGUUUGAGACC
AGCCCGGCCAACAUGGUGAAACCCCAUCUCUAUUAAAAUGCAAAAAUUAG
CCAGGCAUGGUGAUGGUGCACACCUGUAAUCCCAGCCACUCUGGAGGCUG
AGACAGGAGAAUCACUUGAACCCAGGGAGGCAGAGAUUGCAGUGAGGGAG
AUCGCGCCACUGCACUCCAGCCUGGGCAACAGAGGGAGACUCCGUUCAA
AAAAUAAAAACUAUGGUGACUAGAGGCAUCUGGCGUUUAUUUUCUCC
AGUCCAGUUCUAUAAGUCAAGCAAGAAGAAUGGGCAGUCCCUGGAAGAGU
AUUUUGAUGGGACAGGAGUGGGAGGCUCUGGGGUUUACAUUGCUCUCAA
CUGUCACAUUGAGCAUGCUUGGCCUCUAGUGUGUUGAUAAGCAUUGGAAG
AGUCUGCCUACUCAGCAGCAUUGUGCCUGGAGUGGCAGAUUUUGGAAUG
GGGGAAGCAAAUUUGAGCAGAGGGAAACUGUCGUUAGAAACUAGUUUAGAG
GCAGUGGUUAAAAGCCAGCCUAUUGUGUGAGGGUUUAGCAGAAGGCCUACC
AUUUGUUAAGAUGAAUGGGCUUUGUUUUUCUCUUGGGUGUAUCAGGACCC
AAAGAUGUAAGAACCCCAUGGCUUCCUAGCUGAGCACAGCAUUUUCUUU
GUCUCUUGCAAAAUUGUGAGGAUAUUCCAAUGGGAAUCUAUUUUGUCUU
GGUUUGUUGACUUCAGUAUCCCCAGCCCUUAGAACAAUGCCUGGUACAUA
AUAGAGACUCAUGAAUUUGUUGAAUGAAGAAAUUCGUUUAAAAAUUUAU
UUUCUUUGCUUCCUUCAUUUGUCUGGCCUUCCUACUUUGGUUAAUGCUUAU

INFORMAL SEQUENCE LISTING

```
GUUUUCCUGAGCCUUACUAACACGAGGCCGCUCUUAAAAAAGAGAGAGCG
CUGGGUGCUGUGGCUCACGCCUGUAAUCCCAGUACUUUGGGAGGCCGAGG
UGGGCAGAUCACCUGAGGUCAGGAGUUCGAGACCAGCCUGACCACCAUGG
UGAAACCCCAUCUCUAGUAAAAAUGCAAAAUUAGCCAGGUGUGGUGGCGC
AUGCCUGUAAUCCCAGCUACUCGGGAGGCUGAGGCAGGAGAAUCACUUGA
ACCCGGGAGGUGGAGGUUGCAGUUAGCUGAGAUCGCAGCAUUGCAUUCCA
GCCUGGACAACAAAAGCGAAACUCCAUCUCAAAAAAAAAAAAAAAAAAAA
AAAAGGGAGAGGGAGCUUGCUGAGUCUAGUAAGUGACAGCUGGAAACGG
GCUAGGUAAUAAGUUGUGUCACUGUCUGGUGAAUGAUCCUAGCUUCUAG
GAAAUAAACACUGAGUGUAGACCCAGUCGACUUUGAUUGGGUGAGAGGGA
UUUGGAUUUGCCCCAUGUCUCAGCAUUUCUUGGUUUUUGAUUUUUUGAGCC
AACUUUAUGGAAUUGUACUUUUUGCAGAUAUUACUGUGAAGUUCCUUUU
GACCUUGAGCCUCUUUCUGGCGGUUUGAUGUCUGUUAGUGUUUUUUCCAA
AUAUGAUGGUCUUUAUGCUUGGCAUUCCUUUGGUACUAUGGAAUGCCCUG
GCAUCAGUAGGUUUAGCCUAUAAGGAGGGUAGCACCAAUGAUUCUGCUUC
GUUGUCCCAGGCUUGCUUGGUAGAACUUAAGGCCUCCCUGAGCCUCAAG
GGAGGUUGUCUGGCUUACUUAAUUCCCUGGAAAGUUAGCUUAUGCUUUAC
UCUAUACUGUUAAUCAUGGUGACCAUUAAUACCAUGUGCCAGGUAUUAUG
UUAAGCAUUUUACAUUCAUUAUCUCCUUAAGACAAUAAGCCUCUCAGAGAU
AAGUAAUUAUAUUCCUUCUUUUAUAGAGGAGGACAUCAAAGUUCAGAGGUU
AGGUAACUUGCCCAAGAUCACAAUUAAGCAGUGGCAUAAUUGGAAUUCAG
ACCCAAUGGGUCUGACUAUAGAGUUCCUGCUCUUAACCACUCUUUCUGUAA
GUCUAAGACUAUUUUAUUUCUCUAACAACUAUUCAGCCUCCAUUUCUAU
UAUGUCUUCUUAAGUCUUUAUUAGUUUUUCAGCCCUGGGGCGAGGCGCUCAC
ACUGGGGCCUUAUAGCUGGGACACUGACGCUCAAAAUACCAGGAGCUGC
UGGAAUGGGUAUUGUAAAUGUAUGGUAGAUACUGCUCCUCGUGACCUUG
GCUGCCUUUCCUUCAUCUGAGCUUUCUGGUCUAGGGACAGCUUCAUCUAU
UCACUGUUUCUUUCCUAAAGUAGUUUUUAGAGGCGUGUGUUUAGAGGCCGAGGCGUGG
GGCAGGAGUAUCUACUGACUCCAUUUCUCCUUCUAGUUCAAAAGGUGAU
GACCUAUCAACAGCCAUUCUCAAACAGAAGAACCGUCCCAAUCGGUAAU
UGUUGAUGAAGCCAUCAAUGAGGACAACAGUGUGGUGUCCUUGUCCCAGG
UAAGCUGUGGCCACAGACUACUUUCUUACUGCACUUACUGGAGGAU
UUUCCCAGGUUUCUUUCUCAUUUUUCUUGCAGUGACUGCAGAUAGAGUG
GGGUUUACUGGGAAUCCCAAUCUCCAGGGCUGCUGCUUACUCCCCGUCAG
CCCAAUGACCCAAAGGCCUUAACUUUCUUUCCUCAGCCCAAGAUGGAUGA
AUUGCAGUUGUUCCGAGGUGCACAGUGUUGCUGAAAGGAAAGAAAGAC
GAGAAGCUGUUUGCAUCGUCCUUUCUGAUGAACAUUGUUCUGAUGAGAAG
AUUCGGAUGAAUAGAGUUGUUCGGAAUAACCUUCGUGUACGCCUAGGGGA
UGUCAUCAGGUGUGUGUGGGGUUUUGGCUUCACAGGGAUGGGAGGCCAG
AGAUAGCCUGCAUUACAGGCAGGACCCAUGUAUUACAGGCAGGACCAAGU
UCUUGGCACCUGUCGAUGCAGGAGCCUCCUGGUCAUGGAGACUUAUG
CUUCAGGGUUGUCUUUAGGUUUUGGUUCUGCCUCCCUGGGACUUCAAAAU
CCAUUUCUGCAGGUCCCUUGAGACAAAUUGGCGUUCCUGUAACUUUCUUG
AUGGCUUUAUUUUUCCUACUAGAGGUGUAAUUUAUCAUACUUUAUAUCCU
GGCUAAGGAUACCACUCGAGGGUGUGAUGUAUAUGCCAAAUAAUCUCU
CACUACUCUCACUAGUAUGUCUAAUUGAUGGCUUGCGUUGGGUUGGAAU
GAGGUGGGGUAUGGGCAUGGAAGGUGAGCUGCUAGCAGGUCUUUUAAGC
CCCUAAGUUAACCCGGGAGAGAGGAAUAGUUGGAGCCAGACCUGGGAUAG
CUCUCAAUGUGAGUGAUGUUUGCUUGUCUGGCAUAAUUUCUUGGCAUGG
UUACCCCAUCUUGGAGUCAUCUCUAGCCACUCCUACCCAACCAACCAUCA
CCUGGCCAGGAUCAUCUCAGGCUUUGAUUCUUUUGAAUGGAGUCUAAGU
UUCAUGUAGCUUUCUUCUUGGGAGUGCUUAGUCACUUCCUCAAGGUGUUC
UGACCACCUGGCUGAGAAUUUUGUUUUUUUUCACUUCUGUUCUAUGGUUC
CCUGACAAUUGUUAGCUUAAGACCUUCCUUGAAUAUUGGGUCACCAGU
AUUAGCUAGAAGGGGAUCAUCCUUGGAUAUCUCCCUGAAGACCCUGCAUG
UCUUUGUGGGGUUUCUAAAUGUGUGGCUCUUGAUUUUGGCUCACUGAUUA
GGAGUGAGUGGGGCUGGUUCCUUGCCCUCACUUCCACCUGGUCUCCUGC
CUCUCUUCGCCUAAAGCCAUCCUGCCUUUCUUUUUUCACUUACUAUCAGC
UAUCUGUGCCAGGCCCUUUUGGACACCCAGUCUUGGGCCCGAAGUGUGG
UUGGUAAUAUGGAGUCUGCUUGUCAUCCUCAGCAUCCAGCCAUGCCUGA
UGUGAAGUACGCAAACGAUCAUAUGUGCUGCCCAUUGAUGACAC

| INFORMAL SEQUENCE LISTING |
|---|
| UGUUGACCCUCAUGGAUGGCCUAAAGCAGAGGGCACAUGUGAUUGUUAUG
GCAGCAACCAACAGACCCAACAGCAUUGACCCAGCUCUACGGCGAUUUGG
UAAGGACUCCAGAUACUUUUGACCCCGUCCUUGCUUAGGUCCUACUCUG
UCCUUCAUCUAAGUCACCUAAACCUCUUGAAGCCUUCACAGUGAUUGG
UCCAGGGGUCUUUUUCCUUUACCCUACGUCCUGUCUAGAGUGACCAACCA
CCCUGGUUUUCCUGAGACUGAAAGGUUUCCCAGAGCUUGAGACAGUGCUG
GCAUUAGGACAAUCCUGUGCUGGCUGAGAUGGUUGGUCACCCUAGGCCUG
UCUCUUACCUCUGGACUAGAGAUGAGCCCUGUUUAUGUUUGUGUACUGUC
CCACAGGUCGCUUUGCAGGGAGGUAGAUAUUGGAAUUCUGAUGCUACA
GGACGCUUAGAGAUUCUUCAGAUCCAUACCAAGAACAUGAAGCUGGCAGA
UGAUGUGGACCUGGAACAGGUGAAGUGAUGAUGAUGGCUGACCAGGCGUU
ACAGUGUCUCUAGGCAGUUGCUGGGAACUGGCUAGAGACAUAAGGUUAAG
AUGUGAGGAGAUGGUUUUGAUUUCUGGACAGGGGAAAGGAAGUAAUCUG
AGAUUGAAUCCAGGAAAUGGGAGUUGGCAUUUUUCAUAGUUGACGCUGCA
UUUAGAGUGAAAUCAGAAUGUUUGGAGCAGCCUUUAUUUCUAGGUCCCAAGU
CCAGAAUUAAGUACUUAAAAUCCAGCCCAUAAAGGUAUUGAUGAGAUAUA
UUCAAGGAAAUGAGAGGACCCAGGGAUAGCAGUCAGGGGAAGGAUUCUAU
UGUCUCUGAGCCUCCUGCAGCAGCUGGGUCUUUGAGGCAGCAUAGUAAGU
AGAUCUUUCUCUGCAGGUAGCCAAUGAGACUCACGGGCAUGUGGGUGCUG
ACUUAGCAGCCCUGUGCUGCAGAGGCUGCUCUGCAAGCCAUCCGCAAGAA
AUGGAUCUCAUUGACCUAGAGGAUGAGACCAUUGUGACGCGAGGUCAUGAA
CUCUCUAGCAGUUACUAUGGAUGACUUCCGGGUAAGGACCACACCCGUGC
CUCAGGUACACAUACGUGCUUUGACCCCUCCCUUGAUAAGUCUCAUCC
CCAGUUUUCCCUCUUUUCUUGAGCCUUGAGCCAGAGUAAUCCAUCAG
CACUGCGGGAAACCGUGGUAGAGGUGCCACAGGUGAACCUGGGAAGCAUC
GGGGGCUAGAGGAUGUCAAACGUGGCUACAGGAGCUGGUCCAGGUAGG
GCAACUUGGUCCAGGGUGAGUCACUGCUCAGUACAUUGUAAUUGAUCUG
GGUGAUCCUCAGGGUGUCAACACAUUUGCUGCAAGAGUUGUGAGAGCACGA
CUUAGGAACCUACUGUUCUUUAGGUUUGAGGCACUAAGGAGUCUUCUUCUA
GAGAACCUGGAUCUGAUACCAUUGGGUACACCAUGAAAUAAAUGGAGGGGA
UGCUUCUGUUUAGUUAGGUUUCUUUCAAAAUGUGGAGGUAGCCUUGAACC
CUCUUUUCUCCUAGAUGCCUGUGAGCACCCACACAAAAUUCCUG
AAGUUUGGCAUGACACCUUCCAAGGGAGUUCUGUCUAUGGACUUCCUGG
CUGUGGGAAACUUUGUUGGCAAAGCAUUGCUAAUGAAUGCCAGGCCA
ACUUCAUCUCCAUCAAGGGUCCUGAGCUGCUCACCAUGUGGUUUGGGAG
UCUGAGGCCAAUGCAGAGAAAUCUUUGACAAGGUGACUUACAAUAGGCU
GAACUAUGUAUUGAUUUGGCCUGAGGGCAAGGAAUAGAGGCUGUUUUUCUU
UAAGAGGGUUGAAAUAUUCUUAGUGCUGGCUGCUCAACUGCACAGUAAGU
CACUUGAUUUUCUUUCUGAGGUCUGAGAGACCUAGUGUUAUUUUUUUUU
CUCUCUCUCUCCUUGAGACAGGGUCGGCUCUGUGGUCCCAGGUGGAG
GGCAGUGGUACAGUCAUGGCUCACUGCAACCUUGAAACUCGGGCUUAAGG
AAUUCUCCUACUUCAGCCUCCUGAGUAGCUGGACUAUAGGCAUGCGUCA
CCACAUCUGGCUAAUUUUUAUUUUUUGUAGAGACAAAGUCUCAGUAUGUU
GCCCAUGCUGGUUUCGGAUUUCUGGCCUCAAGUGAUCCUCCCACCUUGGC
CUCCCAAGUGCUGGGAAUACAGGUGUGAGCCACCACGUGGCCUAGAGA
CAUCUAGUUUUGUUAGUGCUUGAAUCAAUCCAUUCUCCUACAGGCCCGC
CAAGCUGCCCCCUGUGUGCUAUCUUUGAUGAGCUGGAUUCGAUUGCCAA
GGCUCGUGGAGGUAACAUUGGAGAUGGUGGUGGGGCUGCUGACCGAGUCA
UCAACCAGAUCCAGACAGAAAUGGACAGUGACUGCCACAAAAAUGUGG
UUCAUCAUUGGCGCUACCAACCGGCCCUGCAUCAUUGAUCCUGCCAUCCCU
CAGACCCUGGCCGUCUUGAUCAGCUCAUCUACAUCCCACUUCCUGAUGAGA
AGUCCCGUGUUGCCAUCCUCAAGGCUAACCUGCGCAAGUCCCCAGUUGCC
AAGGCAGGUGACAAGCAGACGGCUGUGGGAGACUUGCAUGAGUCCUCAGG
CUGGUACGGAGUGCUCUUUAGUUUCUUGGACAGAUUCACUGGGGUUAGG
GUUGGUCUAAAGGGAAGGUAGAAUUUUUGAGGAUACAAGAUAAUCUAGA
AUCAGGAAUAAAUGGGGUGGCCAAAGAAGGGGCAAACUGUAGUUUGGGAG
UGCUGGGGUAGCCCAAAGAUCUGCUAUCUCGAGAGGAGAGGCUGAAAUGC
UAAGGUACCUCGCUGCUGCUUUUAGGAUGUGGACUUGGAGUUCUGGCU
AAAAUGACUAAUGGCUUCUCUGGAGCUGACUGACAGAGAUUUGCCAGCG
UGCUUGCAAGCUGGCCAUCCGUGAAUCCAUCGAGAGUGAGAUUAGGCGAG
AACGAGAGAGGCAGACAAACCCAUCGCCAUGGUGACGCUGCAUCCUUUC
CCCAGAUGUGCCAAUCAUGGAGAGCCAGGCAGCAGCCACCAUGCCCU
GGGAGUUGAGAGUAGAAGCUGUGGAAAGCAUCUAACUGAAGAAUUU
UAAUAGGGCAUCAAAGAUAAAGAAUGCUGAGGUGAAUCCAUUCAAUUUGG
AAUAAGGCCGAGAAGAGAUGGUCAGGCUCCAUUCUCAGCUGAACCAAGC
UCCAUGAGGAAUCAAAGUAAUGGAGAUGCAGCAAACACAGCAACAGUGG
UUUUGUUUUUGUUUUUUGUUUGUUUGUUUGGUAGACGAAGUCUCACUCUGUU
GCCCAGACUGGAGUGCAGUGGCACGAUCUUGGCUCACUGCAACUUCUGCC
UCCCAGGUUCAAGCGAUUCUCCUGCCUCAGCCUCCCGAGUAGCUGGGACU
ACAGGCACAUGCCACCAUGUCCGGCUAGUUUUUGUAUUUUUUUUUUAGU
AGAAACGGGUUUCACCAUGUUAGCCAGGAUGGUCUCGAUCCUCUGACCU
UGUGAUGUGGCCCCACUCGGCCUCCCAAAGUGCUGGGAUUACAGGCGUGAA
CCACACGUGCAAGCCUUUUGAGCUGAUGAGACUCAUAUACUAUCCCUGA
UGGUUGGGAAGGGAUAGGGUCCACAGACCUCCCAAAUGAAAAGGCAAA
UUCAUGUGUUUGUAAGUUCCAUAAAGGUAAGAUCUGUCAUCACUUG
UUUUCCACAUGUCUUGUGUUACCCUUAAUUAAUUCAUUAAGUCCAAAC
AUGGGACUUAAUGAGCAAAUAAAUGGCUUUCUUUCCCUUUUGAAGGGCUCU | |

| INFORMAL SEQUENCE LISTING |
|---|
| GUGACAUCCCUUCUCUCUCCCAUAAAAGCUUAACAACUACUGAUGAACUA
AUCCUAGGAGGUAGUCACAUAAGUCACAGAAAUUGGCCUCUCAAUGGAAG
AGAUAGGUUUUGAGCUGGGCUGUGAAGAGAGUAGAAUUUGAAUAAAGGGA
AUAAGCAGCCCAAAUAAUGUGCUAGUAGUAGGAUUGCAAUCAUUGGGA
AACCCUGGGUAGAUUUAAGAGUAUAUAUGUCACUGGAAGUGAGACCGCUA
GGUAGGAUGUAAUCCAAAUGUGGUAAGCACUGAAAGCCAUUGGCAUUUCC
UUUUAAAGUAUUAAGGUUUUAAUUAAGGUAUGAUAAAUACAAUAAAAUUC
ACUCUUUCUAUAUACCAUUUCCAUGCUUUUAUGACAAGUGUGUAAGUUC
UAUAACUACUACCACAGUUGAGACUUAAAAUUUCUACUAUCUCAAAAGU
UUCCUUAGCCACUUCAGUCAACAUCUCCCCUCCUUAAGCCCCAUCACUGA
UGUGAUUCUGUCCCCUACAGUUUUCCCUUUUCCCAGAGUGCAUUGACAAGU
UUUUAAGCAGAGCAGUGACUCAAUUUUAGGAAGCAUGGCCUAGCAUCUUA
CCUCAGGUUGGAUUGGAAGGGCAAGGAGACCAAUAAACUGCAGUAAUGGG
AGGCCUGGGAUGAAAUCCAGGCUGGGCUUUAACUAGCCCUAGUGAUCUGU
GUUUUCAACAUAUAGGAGGUAGAAGAGGAUGAUCCAGUGCCUGAGAUCCG
UCGAGAUCACUUUGAAGAAGCCAUGCGCUUUUGCGCCGUUCUGUCUGUCAGUG
ACAAUGACAUUCGGAAGUAUGAGAUGUUUGCCCAGACCCUUCAGCAGAGU
CGGGGCUUUGGCAGCUUCAGGUAAGUUGGUUGGGAGCAUUAGACAGUGCU
UAAGUUACUUUGGGGACCUACACCAAAGGGAUGGGAGUCCUAAGGAAGC
UAGAGGGGUAGUUGUGGAAAUCUUACACAAGGCCCUGUCCUAACCCUCUGUU
UUUGGCUUUGUCUCUUGUACACAGAUUCCCUUCUGGGAACCAGGGUGGAGC
UGGCCCAGUCAGGGCAGUGGAGGCGGCACAGGUGGCAGUGUAUACACAG
AAGACAAUGAUGAUGACCUGUAUGGCUAAGUGGUGGUGGCCAGCUGCAG
UGAGCUGGCCUGCCUGGACCUGGUCCUCUGGGGGUGGGGGCGCUUGCCCA
GGAGAGGGACCAGGGGUGCGCCCACAGCCUGCUCCAUUCUCCAGUCUGAA
CAGUUCAGCUACAGUCUGACUCUGGACAGGGGGUUUCUGUUGCAAAAAUA
CAAAACAAAAGCGAUAAAAUAAAAGCGAUUUUCAUUUGGUAGGCGGAGAG
UGAAUUACAACAGGGAAUUGGCCCUUGGGCCUAUGCCAUUUCUGUUGGA
GUUUGGGGCAGUGCAGGGGACCUGUGUGGGGGUGUGAACCAAGGCACUACU
GCCACCUGCCACAGUAAAGCAUCUGCACUUGACUCAAUGCUGCCCGAGCC
CUCCCUUCCCCCUAUCCAACCUGGGUAGGUGGGUAGGGGCCACAGUUGCU
GGAUGUUUAUAUAGAGAGUAGGUUGAUUUAUUUUACAUGCUUUUGAGUUA
AUGUUGGAAAACUAAUCACAAGCAGUUUCUAAACCAAAAAAUGACAUGU
GUAAAAGGACAAUAAACGUUGGUGUGCAAAUGGAGCCUGAGUCCUGGGCCCU
GUGCCUGCUUCUUUUCCUGGGAACAGCCUUGGGCUACCACCACUCCCAA
GGCAUUCUUCCAAAAUGUGAAAUCCUGGAAGUAAGAUUGCACCUUCUUCCU
CUCCUGAUCAACAUCGGUAUGAUGUCUCCUGUUGCCUCACCCUUUGUCUG
CAGUAACAUCUGGAAUAGGACUGAAAGGGAGCAGCCUGACAGAGCCUCC
AAAAUGUGGAGAAUAUGGCAUCCUCCUCCACCUAUAUUUGAUGUGGACGGUAA
GGCUAGGCCUGCAGGAUCCCUUAUCCUGACCAAAGACUGUGUUGGGGUGC
CAUUUGAAAAUCGCAGGGUUGCAAAAGAAUACAAUCUUACUUGCAGGUGG
AUAUUCUCUAUACUCUCUUUUAAUGCAUCUAAAAAUCCCAAACAUCCCCU
GGUUGGUGACAUUACAGUUGUGUGUCCACCUUUAAUUUAUGUACUUUGAU
UAAAAAAAAAAAACUUUUGUUAAUAUAAAAUUUUAGUAUUGAAUUUUU
UUUUUUUCCAAACAGAAAAAUAGACUAUCCUCUUCAACAGUAAUCACUUAGU
GCUUCUAGGGUCAGUACAGUGAUGCCUUACCCAGAGAGAGAGUAGUGCAG
AGAAAAUAAAUUACUAAAAUUAAAUAUAUGUUGAUUGGCUUUGGGACAUAA
UCUCAAAAGACAGCCUGAACACCGUAAUUUGGAAUAAAAAUCUGUAAUC
UCCAAAGAUCAAAAAUCCUAAAGUCUAAAAUUCUGAAAAUCACAAUCCCA
AAAGGUCAAAAUCCCAAAAUACAAUUCUGGAAGAAAUACUAAACAUUCUU
CGAAAAUUUACUUACAUUUUUAAAAGCGUAUUUAUUUGAGAAACAACACA
ACAGAACGUUUCAUAGGCCACUACACGAUAAAAUAGGGAAUAGUAACAUU
UUUGCAAGAUAAACACUCAGGUAUACCAAUGACAGUUGCACGGAUAUAAC
GGUGAUGACAGAUGAAACAUUCAUAAAGAAAUGAUCUGAAAAAUGAAAUG
GUAAAAUGCUUUGUCACUAUGCUUGGAAUUGUGGGCACCUAGCUUUAU
AUAACUGGUCAUCUGUAAUACUGUGAACAGAA |

VCP protein SEQ ID NO: 9:
MASGADSKGDDLSTAILKQKNRPNRLIVDEAINEDNSVVSLSQPKMDELQ
LFRGDTVLLKGKKRREAVCIVLSDDTCSDEKIRMNRVVRNNLRVRLGDVI
SIQPCPDVKYGKRIFIVLPIDDTVEGITGNLFEVYLKPYFLEAYRPIRKG
DIFLVRGGMRAVEFKVVETDPSPYCIVAPDTVIRCEGEPIKREDEEESLN
EVGYDDIGGCRKQLAQIKEMVELPLRHPALFKAIGVKPPRGILLYGPPGT
GKTLIARAVANETGAFFFLINGPEIMSKLAGESESNLRKAFEEAEKNAPA
IIFIDELDAIAPKREKTHGEVERRIVSQLLTLMDGLKQRAHVIVMAATNR
PNSIDPALRRFGRFDREVDIGIPDATGRLEILQIHTKNMKLADDVDLEQV
ANETHGHVGADLAALCSEAALQAIRKKMDLIDLEDETIDAEVMNSLAVTM
DDERWALSQSNPSALRETVVEVPQVTWEDIGGLEDVKRELQELVQYPVEH
PDKFLKFGMTPSKGVLFYGPPGCGKTLLAKAIANECQANFISIKGPELLT
MWFGESEANVREIFDKARQAAPCVLFFDELDSIAKARGGNIGDGGGAADR
VINQILTEMDGMSTKKNVFIIGATNRPDIIDPAILRPGRLDQLIYIPLPD
EKSRVAILKANLRKSPVAKDVDLEFLAKMTNGFSGADLTEICQRACKLAI
RESIESEIRRERERQTNPSAMEVEEDDPVPEIRRDHFEEAMRFARRSVSD
NDIRKYEMFAQTLQQSRGFGSFRFPSGNQGGAGPSQGSGGGTGGSVYTED
NDDDLYG

INFORMAL SEQUENCE LISTING

Exon 4/Intron 4/Exon 5 Fragment SEQ ID NO: 10:
CATCCAGCCATGCCCTGATGTGAAGTACGGCAAACGTATCCATGTGCTGC
CCATTGATGACACAGTGGAAGGCATTACTGGTAATCTCTTCGAGGTATAC
CTTAAGCCGTACTTCCTGGAAGCGTATCGACCCATCCGGAAAGGTGAGAG
CTAATTCTGAGCTTAAGGATTATTGACTGTAGGGAATAAACCTTGGAACA
TCTTTATCTCATTTTCTTTTTCTTTTTTTTTTTTAAATCTTTTATGCTT
TTCCCCTGTATTTATTTATTCATTTTTTAAGAGATGGGGTCAGCTGGGCA
CCGTGGCTCACACCTATAATCCCAGCAATTTGGGAGGCTGAGGCGGGTGG
ATCACTTGAGGCCAGGAGTTTGAGACCAGCCTGGCCAACATGGCGAAACC
CCATCCGTGGGCACCTGTAATCCCAGCTACCTGGGAGGCTGAGGCATGAGA
ATTGCTTGAACCCAAGAGGTGGAGGTTGCAGTGAGCCAAGATTGGGCCAC
AGTACTGCAGCCTGGGTGACAGAGCAAGACTCTGTCTCAAAAAAAAAAAA
AAAGAGACAGGGTCTCACTATGATGCCCAGGCTGGTCTCAAACTGCTGGG
CTCAAGTGATCCATCTGCCATGGCCTCCCAAAGTGCTGGGATTACAGGCA
TGAGCCATCAAGCCTAGTCTCATTTTCTTTTCTTTTTTTTTTGAGACAGA
GTGTCGCGCTGTCCCCAGGCTGGAGCGCAGTGGTGCAATCTCGGCTCAC
TGCAACCTCCGCCTCCTGGGTTCAAGCAATTCTCCTGCCTCAGCCTCCCA AGTAGCTGGGATTACAGGCGTCTGCCACCACGCCCGGCTAATTTTTGTGT
TTTTAGTAGAGACGGGGTTTCACCATGTTGGTCAGGCTCGTCTCGAACTC
TTGACCTCAGGTGAGCCACTGTGCCCGGCCGCTAGACTCATTTTCATATA
TTTGTATACACACACATGCAAACCCTGCACACATATTCATATGTCTTACC
CTCTTTTTTTCCTCCATCCTTCCTTTGCTCCATCTCTCCCCTTCTCTGTT
CCAGGAGAGTAAGCTATCTTTATGGATCTCTGAAGGAGAAAGTGGTCCAT
TTTGGCTGGGTCAGGGTCCAGAGTGCACAGTTCTACCATTGGTGGTTGTA
GTGAAAACTTGGGCTACCTATATGGCAGAAGTCAGAACTTGATGGGCTTC
TGACATGTCAGGTTTTGTTCACTGACCTCTTGTCAGAGGGACTTCACA
GTTTACCTTTCTCATCTTGCCTGCTGCTTATTAAGACAGGTGGGGTGGAG
TTGGGGAGAGGTAGGGCAATATCTAATGAAGGGCACTATCTAATGAGCTT
GGCATTTTGACCCCAGGGTCTGATGAGTTCTCACTTTGTCTTGTAGTTGA
CACCTCTAACTGTGCTTGTACTGTTTGCTCTCGCAGGAGACATTTTCTT
GTCCGTGGTGGGATGCGTGCTGTGGAGTTCAAAGTGGTGGAAACAGATCC
TAGCCCTTATTGCATTGTTGCTCCAGACACAGTGATCCACTGCGAAGGGG
AGCCTATCAAACGAGAG

---

SEQUENCE LISTING

<160> NUMBER OF SEQ ID NOS: 10

<210> SEQ ID NO 1
<211> LENGTH: 25
<212> TYPE: RNA
<213> ORGANISM: Artificial Sequence
<220> FEATURE:
<223> OTHER INFORMATION: Synthetic polynucleotide

<400> SEQUENCE: 1
aaaaaugucu ccugcgagag caaac                                25

<210> SEQ ID NO 2
<211> LENGTH: 25
<212> TYPE: RNA
<213> ORGANISM: Artificial Sequence
<220> FEATURE:
<223> OTHER INFORMATION: Synthetic polynucleotide

<400> SEQUENCE: 2
ccaccaugga caagaaaaau gucuc                                25

<210> SEQ ID NO 3
<211> LENGTH: 22
<212> TYPE: RNA
<213> ORGANISM: Artificial Sequence
<220> FEATURE:
<223> OTHER INFORMATION: Synthetic polynucleotide

<400> SEQUENCE: 3
cagcacgcau cccaccaugg ac                                   22

<210> SEQ ID NO 4
<211> LENGTH: 25
<212> TYPE: RNA
<213> ORGANISM: Artificial Sequence
<220> FEATURE:
<223> OTHER INFORMATION: Synthetic polynucleotide

<400> SEQUENCE: 4
aucacugugu cuggagcaac aaugc                                25

<210> SEQ ID NO 5
<211> LENGTH: 25
<212> TYPE: RNA

```
<213> ORGANISM: Artificial Sequence
<220> FEATURE:
<223> OTHER INFORMATION: Synthetic polynucleotide

<400> SEQUENCE: 5
ucguuugaua ggcuccccuu cgcag                                           25

<210> SEQ ID NO 6
<211> LENGTH: 25
<212> TYPE: RNA
<213> ORGANISM: Artificial Sequence
<220> FEATURE:
<223> OTHER INFORMATION: Synthetic polynucleotide

<400> SEQUENCE: 6
aucagggaga aaacucaccu cucgu                                           25

<210> SEQ ID NO 7
<211> LENGTH: 18386
<212> TYPE: DNA
<213> ORGANISM: Homo sapiens

<400> SEQUENCE: 7
tttcatattt atctcgtctg cctactacat atacttgcgt gggaaggctt gtgaccgtct       60
agttgagtgc tagttgtcta tgatgcccttt cctgacatc gtctacctta tgaacttgaa     120
gtctgggtat gaggaaaggg ctacaggaat cctcactttg gaggcagtgg ctttagtcct     180
tcacattgcc tgaatgcaga gccccaaagc ccaggacagt gacaatgagt ggagttgggt     240
ctgaagggtg gtctagatag gcctctcagg acaaggcag gtacctgtta cttagagaca      300
ggcaggtttc tctcagagta actcttcact cccttcctaa ttccaaattc tagaaattcg     360
actcgtctta gtcaaatgtg tctgtgtggg tacagggtga aggtgaatt gagtcagcat      420 atcaccaaca gctgcctgtt gactactaac agggacccct gttatttggg cccaaggat      480 tttcaagtcc cagcatatgc agttttcttg ctaatttggg ttctactgaa ttggctgtgt     540
gttctgtggt tgccctttga cttctctgga tttgagtgcc ttattataag gtattaatat     600
taatgacggg aggaagaaag gcacaagcgc tgagaaactg caaaggctgt gggattgggg     660
ttaccagagg gtgcagtgac aatggggtag gagtgggggtg ctagtcagaa agttcagagt    720 agggggtggtt ggaggcagcg ttgagaagga gcaagaagtg tcagggtggt gatgcgtct    780 tagaagatct ccaggttttg ggagaagatg ggtgtatggg ttaccacaat aggactagac     840
taatacaagg gttcagtcta ttgtgccacg ttcttccagg aggataaact ccggagccaa     900
tgaactggag ccaagtggga gagtccgcct ctaagggatt aaagggtctc ctttcactaa     960
tcgatctcgc cctattcctt tcgttgattg gctgagaatt ccaatccgtc gaggaagcgt    1020
agcgttgcgg ccaattgacg tggcgttact aggcgtgtcg catcactgag gcgggagcca    1080
ggccgcaagc gaatttcctg attggctgtg atctgcgggt tgctggggag aggcgcggag    1140
aggcgggcga gagtccgcag ggcaggcgct gattggctga ggtgggagca gcttccctttc   1200 cgatgattcg gctcttctcg gctcagtctc agcgaagcgt ctgcgaccgt cgtttgagtc    1260
gtcgctgccg ctgccgctgc cactgccact gccacctcgc ggatcaggag ccagcgttgt    1320
tcgcccgacg cctcgctgcc ggtgggagga agcgagaggg aagccgcttg cgggtttgtc    1380
gccgctgctc gcccaccgcc tggaagagcc gagcccggc ccagtcggtc gcttgccacc     1440
gctcgtagcc gttacccgcg ggccgccaca gccgccggcc gggagaggcg cgcgccatgg    1500
cttctggagc cgagtgagtg tgcgcgcgcc gttcgcttgc tgcggcggcg cgcaccggga    1560
```

```
ccagccgcgc agggtaggcc cggcggggcc tggccgtggg cgcgtcagag aggtggagac    1620
caggaaagag ggaagggaag ctaggggcg agtgagggc cgtggacccg gcaggcccgg     1680
ctggggccag ctgcgcaccc gcgcgccccc taggcgggc ttgcgttggg tccgggtcgg    1740
agcctgggcc ggatcgtgct gtgtcatgca ggccccggcc cgcccgattg gctcccttag    1800
aacggacgtc tgggcctggc caggtcttcc ggcccactcc gccggcgcgg cgccccgggg    1860
ctttggggcg ccagtctgcc gtccggccta ccacccgccg aaagcctttg gtccccggag    1920
agagcaggcc ccgcgagccc gaggcccag ccgggcccgg tgggcgtgga ctttgcgcca     1980
tgtgaaggcc tcaggagctc tgccaccgag gcggagcccg ggtcgggga aggcccgccg     2040 agctcaggga agctcacagc cgccttttg gagccgggtc ggcggggccg gaggtgggca     2100
tcctctgtgt gtgacctgag tcgtgaagga ctgttaggga gagggcgagc cctacctttc    2160
gcttctggtc ttcttacttt aggcctgttg ttcatactag aaagtttgag ccagttttcc    2220
ttaatgttat gactcgtggg tggggagaaa ggaatttttc tttaacattt taggttcttg    2280
ctaaagttgg aatctcagtt cgtgttttgt gcgccttttc agatttccag gtttcgtggt    2340
gtgcagttta gagttgcact aactcttcaa aaacacaaac gtgcgcgcac tcctttcccc    2400
aaccagctat attgagaaat tacccgggct ctggggcttt ctgaccccac ctccatcctt    2460
aggaaagcgt tagataaaac ttggctacct cagcccattc aatttagaat agagagcttt    2520
tagaggcaaa aaaaaaaaa aaaaaaaaa aaaaacaca gccagcccaa ggaaactcta       2580
tgcaaattac cttccttcct tgaagagatt agttttttga ggtgtgttcc tttttctcaa    2640
gtttctgaat tcggataaag tattactcag ttgcttattt aaaagagtca cttattctga    2700
aagtattctt ttggtttata tgcagtcagc ctcttatttt caaaagtaaa aatctaaaat    2760
tcttggaacc tggcatcatc agctgtttct aacctcttgg tcaccttgat gactcttagc    2820
tgaaacccTT ccaagtcccg tggagtcccc tgtgcagttc tggaaaggga ttacttata     2880 cagaagacaa tggaggattg ccccaaagag tgtccagaac tgctgttggc ccatggtcag    2940
gccaaattca gtcttttaga gattaccaca tctgatctca gtaggtagat gggaattag     3000 aggctttacc ttaagaaaag ggcataccac tcatctccag agccagagtc cgggatggta    3060
ggcagaatgg aggttttcct aggatacagc tttgagatta aaatacaaac tattgaccgg    3120
gcacagtggc tcaggcctgt aatcccagca ttttgggagg ccgaggcagg cagatcactt    3180
gaggtcagga gtttgagacc agcccgggca acatggagaa accccatctc tattaaaatg    3240
caaaaagtag ccaggcatgg tgatggtgca cacctgtagt cccagccact ctggaggctg    3300
agacaggaga atcacttgaa cccagggagg cagagattgc agtgagggag atcgcgccac    3360
tgcactccag cctgggcaac agaggagac tccgtttcaa aaataaaaa actatggtga     3420 ctagaggcat ctggcgtttt atttttctcc agtcccagtt ctataagtca agcaagaaga    3480
tgggcagtcc ctggaagagt attttgatgg acaggagtg ggagagctcg tgggtttaca     3540
ttgctctcaa ctgtcacatt gagcatgctt ggcctctagt gtgttgataa gcattggaag    3600
agtctgccta ctcagcagca ttgtgcctgg agtggcagac ttttggaatg ggggaagcaa    3660
atttgagcag aggaaactgt cgttagaaac tagtttagag gcagtggtta aaaatgcagc    3720
ctatgtgtga gggttagcag aaggcctacc attttgttag atgaatgggg tttgtttttc    3780
tcttgggtgt atcaggaccc aaagatgtaa gaacccatg gcttcctagc tgagcacagc      3840 attttttcttt gtctcttgca aattgtgagg atatttccaa tgggaatact attttgtctt    3900
```

```
gttttgttga cttcagtatc cccagccctt agaacaatgc ctggtacata atagagactc    3960
atgaatttgt tgaatgaaga aattcgtttt aaaaatttat tttctttgct tccttcattg    4020
tctggccttc ctactttggt taatgcttat gttttcctga gccttactaa cacgaggccg    4080
ctcttaaaaa agagagagcg ctgggtgctg tggctcacgc ctgtaatccc agtactttgg    4140
gaggccgagg tgggcagatc acctgaggtc aggagttcga gaccagcctg accaccatgg    4200
tgaaacccca tctctagtaa aaatgcaaaa ttagccaggt gtggtggcgc atgcctgtaa    4260
tcccagctac tcgggaggct gaggcaggag aatcacttga acccgggagg tggaggttgc    4320
agttagctga gatcgcagca ttgcattcca gcctggacaa caaaagcgaa actccatctc    4380 aaaaaaaaa aaaaaaaaa aaaagggag agggagcttg ctgagtctag taagtgacag    4440
ctggaaacgg gctaggtaat aagttggtgt cactgtctgg tgaatgatcc tagcttctag    4500
gaaataacac tgagtgtaga cccagtcgac tttgatttgg gtgagaggga tttggatttg    4560
ccccatgtct cagcatttct tggttttgat ttttgagcc aactttatgg aattgtgtac    4620
ttttgcagat attactgtga agttcctttt gaccttgagc ctctttctgg cggtttgatg    4680
tctgttagtg ttttttccaa atatgatggt ctttatgctt ggcattcctt tggtactatg    4740
gaatgccctg gcatcagtag gtttagccta taaggagggt agcaccaatg attctgcttc    4800
gttgtcccca ggcttgcttg gtagaactta aggcctccct gagcctcaag ggaggttgtc    4860
tggcttactt aattccctgg aaagttagct tatgctttac tctatactgt taatcatggt    4920
gaccattaat accatgtgcc aggtattatg ttaagcattt tacattcatt atctccctta    4980
agacaataag cctctgagat aagtattata ttccttcttt tatagaggag acatcaaag    5040 ttcagaggtt aggtaacttg cccaagatca caattaagca gtggcataat tggaattcag    5100
acccaatggg tctgactata gagttcctgc tcttaaccac tcttctgtaa gtctaagact    5160 attttatt ctctaacaac tattcagcct ccatttctat tatgtcttct tcttaggcca    5220
ttattttctg accctggggc aggatcactc acttggggcc ttatagctgg gacactgacg    5280
ctcaaaatac caggagctgc tggaatgggt attgtaatat gtatggtaga tactgctcct    5340
cgtgaccttg gctgccttc cttcatctga gctttctggt ctagggacag cttcatctat    5400
tcactgtttc tttcctaagt atgagtttta gagactggcg aggcgcttgg ggcaggagta    5460
tctactgact ccatttcctc cttctagttc aaaaggtgat gacctatcaa cagccattct    5520
caaacagaag aaccgtccca atcggttaat tgttgatgaa gccatcaatg aggacaacag    5580
tgtggtgtcc ttgtcccagg taagctgtgg ccacagacta gtctttcctt actgcactta    5640
cttgagggat tttcccaggt ttcttttctc attttcttg cagtgactgc agatagagtg    5700
gggtttactg ggaatcccaa tctccagggc tgctgcttac tccccgtcag cccaatgacc    5760
caaaggcctt aactttcttt cctcagccca agatggatga attgcagttg ttccgaggtg    5820
acacagtgtt gctgaaagga aagaagagac gagaagctgt ttgcatcgtc ctttctgatg    5880
atacttgttc tgatgagaag attcggatga atagagttgt tcggaataac cttcgtgtac    5940
gcctagggga tgtcatcagg tgtgtgtggg gttttttggct tcacagggat gggaggccag    6000
agatagcctg cattacaggc aggacccatg tattacaggc aggaccaagt tcttggcacc    6060
tgtcgatgca ggaagcctcc tggtcatggg aagacttatg cttcagggtt gtctttaggt    6120
tttggttctg cctccctggg acttcaaaat ccatttctgc aggtcccttg agacaaattg    6180
gcgttcctga actttcttg atggctttat ttttcctac tagaggtgta atttatcata    6240
cttatatcct ggcttaggat accactcgag ggtgtgtatg tatatgccaa ataatctcct    6300
```

```
cactactctc actagtatgt ctaattgatg gcttgtgttg gggttggaat gaggtggggg    6360
tatgggcatg gaaggtgagc tgctagcagg tcttttaagc ccctaagtta acccgggaga    6420
gaggaatagt tggagccaga cctgggatag ctctcaatgt gagtgatttt gcttgttctt    6480
gcataatttt aggcaagagg ttaccccatc ttggagtcat ctctagccac tcctacccaa    6540
ccaaccatca cctggccagg atcatctcag gcttttgatt cttttgaatg gagtctaagt    6600
ttcatgtagc tttcttcttg ggagtgctta gtcacttcct caaggtgttc tgaccacctg    6660
gctgagataa ttttgttttt ttcacttctg tttcactgac cctgacaatt gttagcttaa    6720
gaccttccct tgtaatattg ggtcaccagt attagctaga aggggatcat ccttggatat    6780
ctccctgaag accctgcatg tctttgtggg gtttctaaat gtgtggctct tgattttggc    6840
tcactgatta ggagtgagtg gggctgttcc ttcgccctca cttccaccct gttctccttc    6900
ctctcttcgc ctaaagccat cctgcctttt cttttttcact tactatcagc tatctgtgcc    6960 aggcccttt ggacacccag tgcttgggcc cgaagtgtgg ttggtaatat ggagtctgct    7020
tgtcatcctc agcatccagc catgccctga tgtgaagtac ggcaaacgta tccatgtgct    7080
gcccattgat gacacagtgg aaggcattac tggtaatctc ttcgaggtat accttaagcc    7140
gtacttcctg gaagcgtatc gacccatccg gaaaggtgag agctaattct gagcttaagg    7200
attattgact gtagggaata aaccttggaa catctttatc tcattttctt tttctttttt    7260
tttttttaaa tcttttatgc ttttcccctg tatttattta ttcattttt aagagatggg    7320 gtcagctggg caccgtggct cacacctata atcccagcaa tttgggaggc tgaggcgggt    7380
ggatcacttg aggccaggag tttgagacca gcctggccaa catggcgaaa ccccatcgtg    7440
ggcacctgta atcccagcta cctgggaggc tgaggcatga gaattgcttg aacccaagag    7500
gtggaggttg cagtgagcca agattgggcc acagtactgc agcctgggtg acagagcaag    7560
actctgtctc aaaaaaaaaa aaaaagagac agggtctcac tatgatgccc aggctggtct    7620
caaactgctg ggctcaagtg atccatctgc catggcctcc caaagtgctg ggattacagg    7680
catgagccat caagcctagt ctcatttttct tttctttttt ttttgagaca gagtgtcgcg    7740 ctgtcccca ggctggagcg cagtggtgca atctcggctc actgcaacct ccgcctcctg    7800
ggttcaagca attctcctgc ctcagcctcc caagtagctg ggattacagg cgtctgccac    7860
cacgcccggc taatttttgt gttttttagta gagacggggt ttcaccatgt tggtcaggct    7920
cgtctcgaac tcttgacctc aggtgagcca ctgtgcccgg ccgctagact cattttcata    7980
tatttgtata cacacacatg caaaccctgc acacatattc atatgtctta ccctcttttt    8040
ttcctccatc cttcctttgc tccatctctc cccttctctg ttccaggaga gtaagctatc    8100
tttatggatc tctgaaggag aaagtggtcc attttggctg ggtcagggtc cagagtgcac    8160
agttctacca ttggtggttg tagtgaaaac ttgggctacc tatatggcag aagtcagaac    8220
ttgatgggct tctgacatgt caggttttgt tcactgacct cttgtcagag ggactcttca    8280
cagtttacct ttctcatctt gcctgctgct tattaagaca ggtgggtgg agttggggag    8340 aggtagggca atatctaatg aagggcacta tctaatgagc ttggcatttt gaccccaggg    8400
tctgatgagt tctcactttg tcttgtagtt gacacctcta actgtgcttg tactgtttgc    8460
tctcgcagga gacattttc ttgtccgtgg tgggatgcgt gctgtggagt tcaaagtggt    8520
ggaaacagat cctagccctt attgcattgt tgctccagac acagtgatcc actgcgaagg    8580
ggagcctatc aaacgagagg tgagttttct ccctgattcc agtatccgat tttatgatta    8640
```

```
ctcagtgtgg catcatgtgg taactgtcag gactgggtgc tcggccggct gcggtggctg   8700
acacctgtaa tcccagtact ttgggagact gagatgggca gatcacttga ggtcaggtgt   8760
tcaagaccag cctgggcaac atggtgaaat cccatctcta ctaaaaatac aaaaattagc   8820
caggcatggt ggtacacatc tgtaatccca gctactcagg aggctgaggc aggagaatcg   8880
gttgaaccca ggagtcggag gttgcagtga gctgagattg tgccactgca ctccagcctg   8940
ggtgacagag tgagactctg tctcaaaaaa gaaaaagact gggtgttctt tggagaacta   9000
accatctttc agggatgaga aacctgccag ctattcattt ctgggcctaa ttgtttcttg   9060
gatttaccta atgccaggaa tttcaaaaaa ctagactgaa cccaaaatat ataagtgatt   9120
gaaatcattt ttgaagtaaa gctgatggtg gcttcaggcc tctgcccatt cccagggttt   9180
ccagcttcag attttagaga cccttctca gtaagactac gagtaatgtg agaggcaagg   9240
actgtgctag aaatctttgc cttgggattt ttgtagttgt tctttgaggc cggatccctt   9300
tagaggagaa tcttttttaa atttaattta attttaatg agatggagtc ttgctgtatt   9360
gcccaggaac tcctggactc aagcattcct cccacctctg cctcccaaag tgctgggatt   9420
acagatgtga gccaccatgc cgggttgaga atcttcttat acggtaggtt tttgcacact   9480
aggtagtgga atgatttaga gaaactcagc ttttgctgat ataatattct tgccttctcc   9540
tttctttatc tcctccatat tcaggatgag gaagagtcct tgaatgaagt agggtatgat   9600
gacattggtg gctgcaggaa gcagctagct cagataaagg agatggtgga actgcccctg   9660
agacatcctg ccctctttaa ggcaattggt gtgaaggtga gcatcctggg ctctggaatc   9720
aagtctaaag tggtgccaat gtctaatcct gtcccaatgt ctaatcctgg gactgttttc   9780
atgcatggct ttcattattg ccttggatta gaggggcaat aacgtatcct ttagtttacc   9840
taaggctcta aattcattag agctgatggt ctaaaaccag agtaggctaa tcaaattgtc   9900
tgttgtgtgc gtgtgcgcac aaaacacaca cacatatata tatgggtttt tctttacaac   9960
tcttagaata taaaagccat tcttgtatca atggaccctg taaaaacaaa tctcaccata  10020
gtttgccagc ctgtctagag caatgtcacc cagtagaagt aaggaagtta aggaaatttt  10080
cagagtgtta aagggttctg agtctaaaac atttgagaac tattggtcta gagtgtagct  10140
tctcaatctt ttcctagtgg gaaagtgttt ccatggaaca cactgaagat gaagttactc  10200
attttcctag tgggtggcac acaaataatt tcattttcta tgtggacagt ttacatgttc  10260
tgcttgtgga tgaggccata gaaagggtag tgttgaagaa gaaaaatgat gattgtaagg  10320
aacagcattc cagtgtgata aattctggag ggcatgatta ctggagtgag tgatcctctg  10380
gcaatgaaga aaatagaccc tgctctctta aatggcttag ctagtctttg gcccttggtc  10440
tgtctaaaat tgagccctta gtgtaatggc ctcttgcctt tccctagtca tgtatcttca  10500
aacgcatttg gactacagtt tctctgccct tagtctccta tgcaagttgc aatcataaat  10560 gttgccact ttctagcagt attttccctg ctagtaatag aaatgagtgt ggcctaaagt  10620
aattgtcttc ttagcattta ctgcggaggg cttattctta atattgtcag ggttgaagcc  10680
tgattctcac cctctctgga gcgctagtca agccatttta gggtttggga aaggtgggta  10740
acctaatcac actctgcatt ggtccacagc ctcctagagg aatcctgctt tacgacctc   10800 ctggaacagg aaagaccctg attgctcgag ctgtagcaaa tgagactgga gccttcttct  10860
tcttgatcaa tggtgagata tttggttcat cttatgtcta gctagaccca attttgaact  10920
gggcttatga gctggagcac ttatgaacac atccttttg cacccatgcc ctccttcatg  10980
tttatagcat atttcttatg ctgggtatg ttacagacag aagagcaata aagggaagat  11040
```

```
attttacatt ggtgctccct gtcctgcccc ctttgagaaa gattgtggac agactgcaga   11100
gcgggagcaa gctagaatga gaaatcaaag ggtgaatggt tagtgatttg agagggtttg   11160
gggcaaatga actttgatca ctggctcttg gagaatgctg tttagtggtg tgccatctgg   11220
tgtgccatct ctcttgctct agccagaggt cctagagcat ttgctgtcac ctttacagtt   11280
caactgtgag aagagtatag tgagtccctg ggcttctctc cagccttgcc tggtggctgt   11340
cctgggataa tggctggtag aggatgtgag aagtaggcag aggttaccac cttctcaccc   11400
aggacctgtc tctgggccaa acaagcaaga taactgattt ttgggaggaa ttgggaaaga   11460
ctatcatttt gttattgtct ccattctgta tcctttcagg tcctgagatc atgagcaaat   11520
tggctggtga gtctgagagc aaccttcgta aagcctttga ggaggctgag aagaatgctc   11580
ctgccatcat cttcattgat gagctagatg ccatcgctcc caaaagagag aaagtaggag   11640
cttacctgag gggatagagg ggggttgaaa ggccctgact tcacttctga ccagacatcc   11700
tgttctggca gactcatggc gaggtggagc ggcgcattgt atcacagttg ttgaccctca   11760
tggatggcct aaagcagagg gcacatgtga ttgttatggc agcaaccaac agacccaaca   11820
gcattgaccc agctctacgg cgatttggta aggactccag atacttttga ccccgtcctt   11880
gcttaggtcc tacttctctc cttcatctaa gtcacctaat cctcttgaag cccttcacag   11940
tgattgggtc caggggtctt tttcctttac cctacgtcct gtctagagtg accaaccacc   12000
ctggttttcc tgagactgaa aggtttccca gagcttgaga cttttttagt gctggcatta   12060
ggacaatcct gtgctggctg agatggttgg tcaccctagg cctgtctctt acctctggac   12120
tagagatgag ccctgtttat gtttgtgtac tgtcccacag gtcgctttga cagggaggta   12180
gatattggaa ttcctgatgc tacaggacgc ttagagattc ttcagatcca taccaagaac   12240
atgaagctgg cagatgatgt ggacctggaa caggtgaagt gatgatgatg gctgaccagg   12300
cgttacagtg tctctaggca gttgctggga actggctaga gacataaggt taagatgtga   12360
ggagatgggt tttgatttct ggacagggga aaggaagtaa tctgagattg aatccaggaa   12420 atggagttg gcattttttca tagttgacgc tgcatttaga gtaaatcaga attgttggag   12480
cagccttatt tctaggtccc aagtccagaa ttaagtactt aaaacccagc ccataaaggt   12540
attgatagta tatattcaag gaaatgagag gacccaggga tagcagtcag gggaaggatt   12600
ctattgtctc tgagcctcct gcagcagctg ggtctttgag gcagcatagt aagtagatct   12660
ttctctgcag gtagccaatg agactcacgg gcatgtgggt gctgacttag cagccctgtg   12720
ctcagaggct gctctgcaag ccatccgcaa gaagatggat ctcattgacc tagaggatga   12780
gaccattgat gccgaggtca tgaactctct agcagttact atggatgact tccgggtaag   12840
gaccacaccc gtgcctcagg tacacacata cgtgctttga ccctcccctt gataagtctc   12900
atccccagtt ttccctcctt ttctagtggg ccttgagcca gagtaaccca tcagcactgc   12960
gggaaaccgt ggtagaggtg ccacaggtaa cctgggaaga catcggggc ctagaggatg   13020 tcaaacgtga gctacaggag ctggtccagg tagggcaact tggtccaggg tgagtcactg   13080
tctcagtaca ttgtaattga tctgggtgat ctcagggtgt caacacattt gctgcaagag   13140
ttgtgagagc acgacttagg aacctactgt tcttaggttt gaggcactaa ggagtcttct   13200
tctagagaac ctggatctga taccattggg tacaccatga aataatggag gggatgcttc   13260
tgtttagtta ggtttctttc aaaatgtgga ggtagccttg aaccctcttt ccttttcctc   13320
ctagtatcct gtggagcacc cagacaaatt cctgaagttt ggcatgacac cttccaaggg   13380
```

```
agttctgttc tatggacctc ctggctgtgg gaaaactttg ttggccaaag ccattgctaa    13440
tgaatgccag gccaacttca tctccatcaa gggtcctgag ctgctcacca tgtggtttgg    13500
ggagtctgag gccaatgtca gagaaatctt tgacaaggtg agctacaata ggctgaacta    13560
tgtattgatt tgcctgaggg caaggaatag aggctgtttt tctttaagag ggttgaaata    13620
ttcttagtgc tggctgctca actgcacagt aagtcacttg attttctttc tgaggtctga    13680
gagacctagt gttattttt ttttctctct ctctctcttg agacagggtc tggctctgtt    13740
gcccaggttg gagggcagtg gtacagtcat ggctcactgt aaccttgaaa cctgggctta    13800
agcaattctc ctacttcagc ctcctgagta gctgggacta taggcatgcg tcaccacatc    13860
tggctaattt tttatttttt gtagagacaa agtctcagta tgttgcccat gctggtttcg    13920
gatttctggc ctcaagtgat cctcccacct tggcctccca aagtgctggg aatacaggtg    13980
tgagccacca cgtttgccta gagacatcta gttttgttag tgcttgaatc aatccattcc    14040
tcctacaggc ccgccaagct gcccctgtg tgctattctt tgatgagctg gattcgattg    14100
ccaaggctcg tggaggtaac attggagatg gtggtggggc tgctgaccga gtcatcaacc    14160
agatcctgac agaaatggat ggcatgtcca caaaaaaaaa tgtgttcatc attggcgcta    14220
ccaaccggcc tgacatcatt gatcctgcca tcctcagacc tggccgtctt gatcagctca    14280
tctacatccc acttcctgat gagaagtccc gtgttgccat cctcaaggct aacctgcgca    14340
agtccccagt tgccaaggca ggtgcaagat catgggctgt gggagacttg catgagtcct    14400
caggctggta cggagtgctc tttagtttct ggacaagatt ccactggggt tagggttggt    14460
ctaaagggaa ggtagaattt tgaggtatat caagataatc tagaatcagg aataaaatgg    14520
ggtggccaaa gaaggggcaa actgtagttg ggagtgctcg ggtagcccaa agatctgcgt    14580
atctcgagag gagaggctaa atgctaaggt acctctgctg ctgcttttag gatgtggact    14640
tggagttcct ggctaaaatg actaatggct tctctggagc tgacctgaca gagatttgcc    14700
agcgtgcttg caagctggcc atccgtgaat ccatcgagag tgagattagg cgagaacgag    14760
agaggcagac aaacccatca gccatggtga gtctgcatcc tttccccaga tgtgccaatc    14820
atggagagcc aggcagcagc caccaccatg ccctggagtt gagagtagaa gctgttggaa    14880
agatcatcta actgagaaga attttaatag ggcatcaaag ataaagaatg ctgaggtgaa    14940
tccattcaat ttggaataag gccgagaaga gatggtcagg ctccattctc agtctgaacc    15000
aagctccatg agggaaatca agtatgaga gtgcagcaaa cacagcaagg ttttttttgt    15060
tttttgtttt ttgttttttt tttgagacga agtctcactc tgttgcccag actggagtgc    15120
agtggcacga tcttggctca ctgcaacttc tgcctcccag gttcaagcga ttctcctgcc    15180
tcagcctccc gagtagctgg gactacaggc acatgccacc atgtccggct agttttttgt    15240
attttttttt tagtagaaac gtggtttcac cacgttagcc aggatggtct cgatctcctg    15300
accttgtgat gtgcccacct cggcctccca aagtgctggg attacaggcg tgaaccacag    15360
agcaaggttt tgagctgaga tgagactcat atacttatcc ctgatggttg gggaagggat    15420
agggtccaca gacctcccaa aatgaaaagg caaattcatg tgtttgtaag ttccataaag    15480
gtaagatctc tgtcatctca cttgttttcc actatgtctt gtgttaccct taattaattc    15540
attaagttcc aaacatggga cttaatgagc aaataaatgg cttcttttcc cttttgaagg    15600
gtctgtgaca tcccttctct ctcccataaa agcttaacaa ctactgatga actaatccta    15660
ggaggtagtc acataagtca cagaaattgg cctctcaatg gaagagatag gttttgagct    15720
gggctgtgaa gagagtagaa tttgaataaa gggaataagc agcccaaata atgtgctcta    15780
```

```
gtagtaggat tgcaatcatt gggaaaccct gggtagattt aagagtatat atgtcactgg   15840
aagtgagacc gctaggtagg atgtaatcca aatgtggtaa gcactgaaag ccattggcat   15900
ttccttttaa agtattaagg tttattaagg tatgatataa atacaataaa attcactctt   15960
tctatatacc atttccatgc tttatgacaa gtgtgtgtaa gttctataac tactaccaca   16020
gttgagactt aaaatttcta ctatctcaaa aagtttcctt agccacttca gtcaacatct   16080
cccctcctta agcccatca ctgatgtgat ttctgtccct acagttttcc cttttccaga    16140
gtgcattgac aagttttaa gcagagcagt gactcaattt taggaagcat ggcctagcat    16200
cttacctcag gttggattgg aagggcaagg agaccaataa actgcagtaa tgggaggcct   16260
gggatgaaat ccaggctggg ctttaactag ccctagtgat ctgtgtttac caactatagg   16320
aggtagaaga ggatgatcca gtgcctgaga tccgtcgaga tcactttgaa gaagccatgc   16380
gctttgcgcg ccgttctgtc agtgacaatg acattcggaa gtatgagatg tttgcccaga   16440
cccttcagca gagtcgggc tttggcagct tcaggtaagt tggttgggag cattagacag     16500
tgcttaagtt actttgggga cctacaccaa aagggatggg agtcctaagg aagctagagg    16560
ggtagttgtg gaaatcttac acaggccctg tcctaaccct cttttttggc tttgctcttg    16620
tacacagatt cccttcaggg aaccagggtg gagctggccc cagtcagggc agtggaggcg    16680
gcacaggtgg cagtgtatac acagaagaca atgatgatga cctgtatggc taagtggtgg    16740
tggccagcgt gcagtgagct ggcctgcctg gaccttgttc cctggggtg ggggcgcttg     16800 cccaggagag ggaccagggg tgcgcccaca gcctgctcca ttctccagtc tgaacagttc    16860
agctacagtc tgactctgga cagggggttt ctgttgcaaa aatacaaaac aaaagcgata    16920
aaataaaagc gattttcatt tggtaggcgg agagtgaatt accaacaggg aattgggcct    16980
tgggcctatg ccatttctgt tgtagtttgg ggcagtgcag gggacctgtg tggggtgtga    17040
accaaggcac tactgccacc tgccacagta aagcatctgc acttgactca atgctgcccg    17100
agccctccct tccccctatc caacctgggt aggtgggtag gggccacagt tgctggatgt    17160
ttatatagag agtaggttga tttatttttac atgcttttga gttaatgttg gaaaactaat   17220
cacaagcagt ttctaaacca aaaaatgaca tgttgtaaaa ggacaataaa cgttgggtca    17280
aaatggagcc tgagtcctgg gccctgtgcc tgcttctttt cctgggaaca gccttgggct    17340
acccaccact cccaaggcat tcttccaaat gtgaaatcct ggaagtaaga ttgcaccttc    17400
ttcctctcct gatcaacatc ggtatgatgt ctcctgttgc ctcacccttt gtctgcagta    17460
tcactggata ggactggtgg aaagggagca gcctgacaga gctccaaatg tggagaatat    17520
ggcatccctc cacctatatt tgatgtggac ggtaaggcta ggcctgcagg atcccttatc    17580
ctgaccaaag actgtgttgg ggtgccattt gaaaatcgca gggttgcaaa agaatacaat    17640
cttacttgca ggtggatatt ctctatactc tcttttaatg catctaaaaa tcccaaacat    17700
cccctggttg gtgatcactt acagttgtgt ccacctttat tttatgtact ttgattaaaa    17760
aaaaaaaact ttttgttaat ataaaatttt agtattgaat ttttttttt tccaaacaga     17820 aaatagacta tcctcttcaa cagtaatcac ttagtgcttc tagggtcagt acagtgatgc    17880
cttacccaga gagagagtag tgcagagaaa ataaattact aaattaaata tatgttgatt    17940
ggctttggga cataatctca aaagacagtc ctgaacaccg taattttgaa taaaatactg    18000
taatctccaa agatcaaaat ccctaaagtc taaaattctg aaaatcacaa tcccaaaagg    18060
tcaaaatccc aaaatacaat tctggaagaa atactaaaca ttcttcgaaa atttacttac    18120
```

| | | | | | |
|---|---|---|---|---|---|
| atttttaaaa | gcgtatttat | ttgagaaaca | acacaacaga | acgtttcata | ggccactaca | 18180 |
| cgataaaata | gggaatagta | acattttgc | aagataaaca | ctcaggtata | ccaatgacag | 18240 |
| ttgcacggat | ataacggtga | tgagcagatg | aaacattcat | aaagaaatag | gtcaaaaagt | 18300 |
| gaaatgtata | aatgctttgt | cactatgctt | ggtaattgtg | ggcacctagc | tttatataac | 18360 |
| tggtcatctg | taatactgtg | acagaa | | | | 18386 |

<210> SEQ ID NO 8
<211> LENGTH: 18386
<212> TYPE: RNA
<213> ORGANISM: Homo sapiens

<400> SEQUENCE: 8

| | | | | | |
|---|---|---|---|---|---|
| uuucauauuu | aucucgucug | ccuacuacau | auacuugcgu | gggaaggcuu | gugaccgucu | 60 |
| aguugagugc | uaguugucua | ugaugcccuu | uccugacauc | gucuaccuua | ugaacuugaa | 120 |
| gucuggguau | gaggaaaggg | cuacaggaau | ccucacuuug | gaggcagugg | cuuuagaccu | 180 |
| ucacauugcc | ugaaugcaga | gccccaaagc | ccaggacagu | gacaaugagu | ggaguugggu | 240 |
| cugaagggug | gucuagauag | gccucucagg | acaagggcag | guaccuguua | cuuagagaca | 300 |
| ggcagguuuc | ucucagagua | acucuucacu | cccuuccuaa | uuccaaauuc | uagaaauucg | 360 |
| acucgucuua | gucaaaugug | ucugugugg | uacaggguga | aaggugaauu | gagucagcau | 420 |
| aucaccaaca | gcugccuguu | gacuacuaac | agggaccccu | guuauuuggg | gcccaaggau | 480 |
| uuucaagucc | cagcauaugc | aguuuucuug | cuaauuuggg | uucacugaa | uuggcugugu | 540 |
| guucugugug | ugcccuuuga | cuucucugga | uuugagugcc | uuauuauaag | guauuaauau | 600 |
| uaaugacggg | aggaagaaag | gcacaagcgc | ugagaaacug | caaaggcugu | gggauugggg | 660 |
| uuaccagagg | gugcagugac | aaugggguag | gaguggggug | cuagucagaa | aguucagagu | 720 |
| aggggugguu | ggaggcagcg | uugagaagga | gcaagaagug | ucaggugguu | gaugggucu | 780 |
| uagaagaucu | ccagguuuug | ggagaagaug | ggugauaggg | uuaccacaau | aggacuagac | 840 |
| uaauacaagg | guucaguucua | uugugccacg | uucuuccagg | aggauaaacu | ccggagccaa | 900 |
| ugaacuggag | ccaaguggga | gauccgccu | cuaagggauu | aaaggucuc | cuuucacuaa | 960 |
| ucgaucucgc | ccuauuccuu | ucguugauug | gcugagaauu | ccaauccguc | gaggaagcgu | 1020 |
| agcguugcgg | ccaauugacg | uggcguuacu | aggcgugucg | caucacugag | gcgggagcca | 1080 |
| ggccgcaagc | gaauuuccug | auuggcugug | aucgcgggu | ugcugggag | aggcgcggag | 1140 |
| aggcgggcga | gaguccgcag | ggcaggcgcu | gauuggcuga | gguggagca | gcuucccuuc | 1200 |
| cgaugauucg | gcucuucucg | gcucagucuc | agcgaagcgu | cugcgaccgu | cguuugaguc | 1260 |
| gucgcugccg | cugccgcugc | cacugccacu | gccaccucgc | ggaucaggag | ccagcguugu | 1320 |
| ucgcccgacg | ccucgcugcc | ggugggagga | agcgagaggg | aagccgcuug | cgggguugc | 1380 |
| gccgcugcuc | gccccaccgcc | uggaagagcc | gagccccggc | ccagucgguc | gcuugccacc | 1440 |
| gcucguagcc | guuacccgcg | ggccgccaca | gccgccggcc | gggagaggcg | cgcgccaugg | 1500 |
| cuucuggagc | cgagugagug | ugcgcgcgcc | guucgcuugc | ugcggcggcg | cgcaccggga | 1560 |
| ccagccgcgc | aggguaggcc | cggcggggcc | uggccguggg | cgcgucagag | agguggagac | 1620 |
| caggaaagag | ggaagggaag | cuaggggggcg | aguagggggc | cguggacccg | gcaggcccgg | 1680 |
| cuggggccag | cugcgcaccc | gcgccccccc | uagcggggc | uugcguuggg | uccgggucgg | 1740 |
| agccuggggcc | ggaucgugcu | gugucaugca | ggccccggcc | cgcccgauug | gcucccuuag | 1800 |
| aacggacguc | uggccuggc | caggucuucc | ggcccacucc | gccggcgcgg | cgccccgggg | 1860 |

```
cuuuggggcg ccagucugcc guccggccua ccacccgccg aaagccuuug guccccggag    1920
agagcaggcc ccgcgagccc gaggcccag  ccgggcccgg ugggcgugga cuuugcgcca    1980
ugugaaggcc ucaggagcuc ugccaccgag gcggagcccg ggucgggga  aggcccgccg    2040 agcucaggga agcucacagc cgccuuuuug gagccgdgguc ggcggggccg gagugggca    2100 uccucugugu gugaccugag ucgugaagga cuguuaggga gagggcgagc ccuaccuuuc    2160
gcuucggguc uucuuacuuu aggcuguug  uucauacuag aaaguuugag ccaguuuucc    2220
uuaauguuau gacucguggg uggggagaaa ggaauuuuuc uuuaacauuu uagguucuug    2280
cuaaaguugg aaucucaguu cguguuugu  gcgccuuucc agauuccag  guuucguggu    2340 gugcaguuua gaguugcacu aacucuucaa aaacacaaac gugcgcgcac uccuuucccc    2400
aaccagcuau auugagaaau uacccgggcu cugggggcuuu cugaccccac cuccauccuu    2460
aggaaagcgu uagauaaaac uuggcuaccu cagcccauuc aauuuagaau agagagcuuu    2520
uagaggcaaa aaaaaaaaa  aaaaaaaaaa aaaaaacaca gccagcccaa ggaaacucua    2580
ugcaaauuac cuuccuuccu ugaagagauu aguuuuuga  ggugguguucc uuuuucucaa    2640 guuucugaau ucggauaaag uauuacucag uugcuuauuu aaaagaguca cuuauucuga    2700
aaguauucuu uugguuuaua gcagucagc  ucuuauuuu  caaaaguaaa aaucuaaaau    2760
ucuuggaacc uggcaucauc agcuguuucu aaccccuugg ucaccuugau gacucuuagc    2820
ugaaacccuu ccaaguccg  uggagucccc ugugcaguuc uggaaaggga uugacuuaua    2880
cagaagacaa uggaggauug ccccaaagag uguccagaac ugcuguuggc ccauggucag    2940
gccaaauuca gucuuuuaga gauuaccaca ucugaucuca guagguagau ggggaauuag    3000
aggcuuuacc uuaagaaaag ggcauaccac ucaucuccag agccagaguc cgggaugg ua   3060 ggcagaaugg agguuuuccu aggauacagc uuugagauua aaaucaaac  uauugaccgg    3120 gcacagugge ucaggccugu aaucccagca uuuuggagg  ccgaggcagg cagaucacuu    3180
gaggucagga guuugagacc agcccgggca acauggagaa accccaucuc uauuaaaaug    3240
caaaaaguag ccaggcaugg ugauggugca caccuguagu cccagccacu cuggaggcug    3300
agacaggaga aucacuugaa cccagggagg cagagauugc agugagggag aucgcgccac    3360
ugcacuccag ccugggcaac agagggagac uccguuucaa aaauaaaaa  acuaugguga    3420 cuagaggcau cuggcguuuu auuuucucc  aguccccaguu cuauaaguca agcaagaaga    3480 ugggcaguce cuggaagagu auuuugaugg gacaggagug ggagagcucg uggguuuaca    3540
uugcucucaa cugucacauu gagcaugcuu ggcucuagu  uguugauaa  gcauggaag     3600 agucugccua cucagcagca uugugccugg aguggcagac uuuuggaaug ggggaagcaa    3660
auuugagcag aggaaacugu cguuagaaac uaguuuagag gcagugguua aaaaugcagc    3720
cuauguguga gggguuagcag aaggccuacc auuuuguuag augaauggggg uuuguuuuuc    3780 ucuuggguguu aucaggaccc aaagauguaa gaaccccaug gcuuccuagc ugagcacagc    3840
auuuuucuuu gucucuugca aauugugagg auauuccaa  ugggaauacu auuuugucuu    3900
guuuguuuga cuucaguauc cccagcccuu agaacaaugc cugguacaua auagagacuc    3960
augaauuugu ugaaugaaga aauucguuuu aaaaauuuau uuucuuugcu uccuucauug    4020
ucuggccuuc cuacuuuggu uaaugcuuau guuuuccuga gccuuacuaa cacgaggccg    4080
cucuuaaaaa agagagagcg cuggugucug uggcucacgc cuguaauccc aguacuuugg    4140
gaggccgagg ugggcagauc accugaggue aggaguucga gaccagccug accaccaugg    4200
```

```
ugaaacccca ucucuaguaa aaaugcaaaa uuagccaggu gguggcgc augccuguaa      4260 ucccagcuac ucgggaggcu gaggcaggag aaucacuuga acccgggagg uggagguugc    4320
aguuagcuga gaucgcagca uugcauucca gccuggacaa caaaagcgaa acuccaucuc    4380
aaaaaaaaaa aaaaaaaaaa aaaaagggag agggagcuug cugagucuag aagugacag     4440 cuggaaacgg gcuagguaau aaguuggugu cacugucugg ugaaugaucc uagcuucuag    4500
gaaauaacac ugaguguaga cccagucgac uuugauuugg gugagaggga uuuggauuug    4560
ccccaugucu cagcauuucu ugguuuugau uuuugagcc aacuuuaugg aauuguguac    4620
uuuugcagau auuacuguga aguuccuuuu gaccuugagc cucuuucugg cgguuugaug    4680
ucuguuagug uuuuuuccaa auaugauggu cuuuaugcuu ggcauuccuu ugguacuaug    4740
gaaugcccug gcaucaguag guuuagccua uaaggagggu agcaccaaug auucugcuuc    4800
guugucccca ggcuugcuug guagaacuua aggcccccu gagccucaag ggagguuguc     4860
uggcuuacuu aauucccugg aaaguuagcu uaugcuuuac ucauaucugu uaaucauggu    4920
gaccauuaau accaugugcc agguauuaug uuaagcauuu acauucauu aucucccuua     4980 agacaauaag ccucgagau aaguauuaua uccuucuuu uauagaggag gacaucaaag      5040
uucagagguu agguaacuug cccaagauca caauuaagca guggcauaau uggaauucag    5100
acccaauggg ucugacuaua gaguccugc ucuuaaccac ucuucuguaa gucuaagacu     5160 auuuuauuu ucuaacaac uauucagccu ccauuucuau uaugucuucu cuuaggcca      5220 uuauuuucug acccugggc aggaucacuc acuuggggcc uuauagcugg gacacugacg     5280
cucaaaauac caggagcugc uggaaugggu auuguaauau guagguaga acugcuccu      5340 cgugaccuug gcugccuuuc cuucaucuga gcuuucuggu cuagggacag cuucaucuau    5400
ucacuguuuc uuuccuaagu augaguuuua gagacuggcg aggcgcuugg ggcaggagua    5460
ucuacugacu ccauuccuc cuucuaguuc aaaggugau gaccaucaa cagccauucu       5520 caaacagaag aaccgucccc aucgguuaau guugaugaa ccaucaaug aggacaacag      5580 uguggugucc uugucccagg uaagcugugg ccacagacua gucuuuccuu acugcacuua    5640
cuugagggau uuucccaggu uucuuuucuc auuuuucuug cagugacugc agauagagug    5700
ggguuuacug ggaaucccaa ucuccagggc ugcugcuuac uccccgucag cccaaugacc    5760
caaaggccuu aacuucuuuu ccucagccca agauggauga auugcaguug uuccgaggug    5820 acacagguguu gcugaaagga aagaagagac gagaagcugu uugcaucguc cuuucugaug   5880
auacuuguuc ugaugagaag auucggauga auagagugu ucggaauaac cuucguguac    5940
gccuagggga ugucaucagg ugugugggg guuuuuggcu ucacagggau gggaggccag    6000
agauagccug cauucaggc aggacccaug uauuacaggc aggaccaagu ucuuggcacc     6060
ugucgaugca ggaagccucc uggucauggg aagacuuaug cuucaggguu gucuuuaggu    6120
uuugguucug ccucccuggg acuucaaaau ccauuucugc aggucccuug agacaaauug    6180 gcguccugu aacuuucuug auggcuuuau uuuuccuac uagaggugua auuuaucaua     6240
cuuauauccu ggcuuaggau accacucgag ggugugaug uauaugccaa auaaucccuu     6300
cacuacucuc acuaguaugu cuaauugaug gcuuguguug ggguuggaau gaggugggg     6360 uaugggcaug gaaggugagc ugcuagcagg ucuuuuaagc cccuaaguua acccgggaga    6420
gaggaauagu uggagccaga ccugggauag cucucaaugu gagugauuuu gcuguucuau    6480
gcauaauuuu aggcaagagg uuaccccauc uuggagucau cucuagccac uccuacccaa    6540
ccaaccauca ccuggccagg aucaucucag gcuuuugauu cuuuugaaug gagucuaagu    6600
```

| | |
|---|---|
| uucauguagc uuucuucuug ggagugcuua gucacuuccu caagguguuc ugaccaccug | 6660 |
| gcugagauaa uuuuguuuuu uucacuucug uuucacugac ccugacaauu guuagcuuaa | 6720 |
| gaccuucccu uguaauauug ggucaccagu auuagcuaga aggggaucau ccuuggauau | 6780 |
| cucccugaag acccugcaug ucuuuguggg guuucuaaau guguggcucu ugauuuuggc | 6840 |
| ucacugauua ggagugagug gggcuguucc uucgcccuca cuuccacccu guucuccuuc | 6900 |
| cucucuucgc cuaaagccau ccugccuuuu cuuuuucacu acuaucagc uaucugugcc | 6960 |
| aggcccuuuu ggacacccag ugcuugggcc cgaagugugg uugguaauau ggagucugcu | 7020 |
| ugucauccuc agcauccagc caugcccuga ugugaaguac ggcaaacgua ccaugugcu | 7080 |
| gcccauugau gacacagugg aaggcauuac ugguaaucuc uucgagguau accuuaagcc | 7140 |
| guacuuccug gaagcguauc gacccauccg gaaaggugag agcuaauucu gagcuuaagg | 7200 |
| auuauugacu uagggaaua aaccuuggaa caucuuuauc ucauuucuu uuucuuuuuu | 7260 |
| uuuuuuaaa ucuuuuaugc uuuucccug uauuuauuua uucauuuuuu aagagauggg | 7320 |
| gucagcuggg caccguggcu cacaccuaua aucccagcaa uuugggaggc ugaggcgggu | 7380 |
| ggaucacuug aggccaggag uuugagacca gccuggccaa cauggcgaaa ccccaucgug | 7440 |
| ggcaccugua aucccagcua ccugggaggc ugaggcauga gaauugcuug aacccaagag | 7500 |
| guggagguug cagugagcca agauugggcc acaguacgc agccgggug acagagcaag | 7560 |
| acucugucuc aaaaaaaaaa aaaagagac aggguucac uaugaugccc aggcuggucu | 7620 |
| caaacgcug ggcucaagug auccaucugc cauggccucc caagugcug ggauuacagg | 7680 |
| caugagccau caagccuagu ucauuuucu uucuuuuuu uuugagaca gagucgcg | 7740 |
| cugucccca ggcuggagcg caguggugca aucgggcuc acugaaccu ccgccuccug | 7800 |
| gguucaagca auucccugc cucagccuc caaguagcug ggauuacagg cgucugccac | 7860 |
| cacgccggc uaauuuugu guuuuagua gagacggggu uucaccaugu uggcaggcu | 7920 |
| cgucgcgaac ucuugaccuc aggugagcca cugugccgg ccgcuagacu cauuucaua | 7980 |
| uauuuguaua cacacacaug caaacccugc acacauauuc auaugucuua cccucuuuu | 8040 |
| uuccuccauc cuuccuuugc uccaucucuc cccuucucug uuccaggaga guaagcuauc | 8100 |
| uuuauggauc ucugaaggag aaagugguc auuuuggcug ggucagggc cagagugcac | 8160 |
| aguucuacca uugguggug uagugaaaac uugggcuacc uauauggcag aagucagaac | 8220 |
| uugaugggcu ucugacaugu cagguuuugu ucacugaccu cuugucagag ggacucuuca | 8280 |
| caguuuaccu uucucaucuu gccugcugcu uauuaagaca ggugggugg aguuggggag | 8340 |
| agguagggca auaucuaaug aagggcacua ucuaaugagc uuggcauuu gaccccaggg | 8400 |
| ucugaugagu ucucacuuug ucuuuaguu gacaccucua acugcuug uacguuugc | 8460 |
| ucucgcagga gacauuuuc uugucgugg ugggaugcgu gcuggagagu ucaaaguggu | 8520 |
| ggaaacagau ccuagcccuu auugcauugu ugcccagac acagaucc acugcgaagg | 8580 |
| ggagccuauc aaacgagagg ugaguuucu ccugauucc aguauccgau uuuaugauua | 8640 |
| cucagugugg caucaugugg uaacugucag gacuggugc ucggccggcu gcggugccug | 8700 |
| acaccuguaa ucccaguacu uugggagacu gagaugggca gaucacuuga ggucaggugu | 8760 |
| ucaagaccag ccugggcaac auggugaaau cccaucucua cuaaaaauac aaaaauuagc | 8820 |
| caggcauggu gguacacauc uguaauccca gcuacucagg aggcugaggc aggagaaucg | 8880 |
| guugaaccca ggagucggag guugcaguga gcugagauug ugccacugca cuccagccug | 8940 |

```
ggugacagag ugagacucug ucucaaaaaa gaaaaagacu ggguguucuu uggagaacua    9000
accaucuuuc agggaugaga aaccugccag cuauucauuu cugggccuaa uuguuucuug    9060
gauuuaccua augccaggaa uuucaaaaaa cuagacugaa cccaaaauau auaagugauu    9120
gaaaucauuu uugaaguaaa gcugauggug gcuucaggcc ucugcccauu cccagggucu    9180
ccagcuucag auuuuagaga ccccuucuca guaagacuac gaguaaugug agaggcaagg    9240
acugugcuag aaaucuuugc cugggauuuu uguaguugu ucuuugaggc cggaucccuu     9300
uagaggagaa ucuuuuuaa auuuaauuua auuuuaaug agauggaguc uugcuguauu      9360
gcccaggaac uccuggacuc aagcauuccu cccaccucug ccucccaaag ugcugggauu    9420
acagauguga gccaccaugc cgggugaga aucuucuuau acgguagguu uuugcacacu     9480
agguagugga augauuuaga gaaacucagc uuuugcugau auaauauucu ugccuucucc    9540
uuucuuuauc uccccauau ucaggaugag gaagagccu ugaaugaagu aggguaugau      9600
gacauuggug gcugcaggaa gcagcuagcu cagauaaagg agauggugga acugccccug    9660
agacauccug cccucuuuaa ggcaauuggu gugaagguga gcauccuggg cucuggaauc    9720
aagucuaaag uggugccaau gucuaauccu gcccaaugu cuaauccugg gacuguuuuc     9780
augcauggcu ucauuauug ccuuggauua gaggggcaau aacguauccu uuaguuuacc     9840
uaaggcucua aauucauuag agcgauggu cuaaaccag aguaggcuaa ucaaauuguc      9900
uguugugugc gugugcgcac aaaacacaca cacauauaua uaugggucuu ucuuuacaac    9960
ucuuagaaua uaaaagccau ucuuguauca auggacccug uaaaaacaaa ucucaccaua   10020
guuugccagc cugucuagag caaugucacc caguagaagu aaggaaguua aggaaauuuu   10080
cagaguguua aagguucug agucuaaaac auuugagaac uauuggucua gaguguagcu    10140
ucucaaucuu uuccuagugg gaagguguuu ccauggaaca cacugaagau gaaguuacuc   10200 auuuccuag ugggucgcac acaaauaauu ucauuucua ugggacaguu uuacauguuc     10260
ugcuugggaa ugaggccaua gaaagggauag uguugaagaa gaaaaaugau gauuguaagg   10320
aacagcauuc caguaugaau aauucuggag ggcaugauua cuggagugag ugauccucug   10380
gcaaugaaga aaauagaccc ugcucucuua aauggcuuag cuagucuuug gcccuuggcu   10440
ugucuaaaau ugaacccuua guguaauggc ucuugccuu ucccuaguca uguaucuuca    10500
aacgcauuug gacuacaguu ucucugcccu uagucuccua ugcaaguugc aaucauaaau   10560
guugcccacu uucuagcagu auuuucccug cuaguaauag aaaugagugu ggccuaaagu   10620
aauugcuuuc uuagcauuuu cugcggaggg cuuauucuua auauugucag gguugaagcc   10680
ugauucucac ccucucugga gcgcuaguca agccauuuua ggguuggga aagguggga     10740 accuaaucac acucugcauu ggccacagc cuccuagagg aauccugcuu uacggaccuc    10800
cuggaacagg aaagacccug auugcucgag cuguagcaaa ugagacugga gccuucuucu   10860
ucuugaucaa uggugagaua uuugguucau cuuaugucua gcagaccca auuuugaacu    10920 gggcuuauga gcuggagcac uuaugaacac auccuuuuug cacccaugcc cucccuucaug  10980 uuuauagcau auucuuaug cugggguaug uuacagacag aagagcaaua aagggaagau    11040
auuuuacauu ggugcucccu guccugcccc cuuuagaaaa gauugugac agacugcaga    11100 gcgggagcaa gcuagaauga gaaaucaaag ggugaauggu uagugauuug agagggucuug  11160 gggcaaauga acuuugauca cuggcucuug gagaaugcug uuuagggug ugccaucugg    11220 ugugccaucu cucuugcucu agccagaggu ccuagagcau uugcugucac cuuuacaguu   11280
caacugugag aagaguauag ugagucccug ggcuucucuc cagccuugcc ugguggcugu   11340
```

```
ccugggauaa uggcugguag aggaugugag aaguaggcag agguuaccac cuucucaccc    11400
aggaccuguc ucugggccaa acaagcaaga uaacugauuu uuggaggaa uugggaaaga    11460 cuaucauuuu guuauugucu ccauucugua uccuuucagg uccugagauc augagcaaau    11520
uggcugguga gucugagagc aaccuucgua aagccuuuga ggaggcugag aagaaugcuc    11580
cugccaucau cuucauugau gagcuagaug ccaucgcucc caaaagagag aaaguaggag    11640
cuuaccugag gggauagagg ggguugaaa ggcccugacu ucacuucuga ccagacaucc    11700
uguucuggca gacucauggc gaggugagc ggcgcauugu aucacaguug uugacccuca    11760
uggauggccu aaagcagagg gcacauguga uuguuauggc agcaaccaac agacccaaca    11820
gcauugaccc agcucuacgg cgauuggua aggacuccag auacuuuuga ccccguccuu    11880
gcuuaggucc uacuucucuc cuucaucuaa gucaccuaau ccucuugaag cccuucacag    11940
ugauuggguc caggggucuu uuccuuuac ccuacgccu gucuagagug accaaccacc    12000
cugguuuucc ugagacugaa agguuuccca gagcuugaga cuuuuuagu gcuggcauua    12060 ggacaauccu gugcuggcug agauggguugg ucacccuagg ccugucucuu accucuggac    12120
uagagaugag cccuguuuau guuuguguac uguccacag gucgcuuuga cagggaggua    12180
gauauuggaa uuccugaugc uacaggacgc uuagagauuc uucagaucca uaccaagaac    12240
augaagcugg cagaugaugu ggaccuggaa caggugaagu gaugaugaug gcugaccagg    12300
cguuacagug ucucuaggca guugcuggga acuggcuaga gacauaaggu uaagauguga    12360
ggagaugggu uuugauuucu ggacaggga aaggaaguaa ucugagauug aauccaggaa    12420
augggaguug gcauuuuuca uaguugacgc ugcauuuaga guaaaucaga auuguuggag    12480
cagccuuauu ucuaggucc aaguccagaa uuaaguacuu aaaacccagc ccauaaaggu    12540
auugauagua uauauucaag gaaaugagag gacccaggga uagcagucag gggaaggauu    12600
cuauugucuc ugagccuccu gcagcagcug ggucuuugag gcagcauagu aaguagaucu    12660
uucucugcag guagccaaug agacucacgg gcaugugggu gcugacuuag cagcccugug    12720
cucagaggcu gcucucaag ccauccgcaa gaagauggau cucauugacc uagaggauga    12780
gaccauugau gccgagguca ugaacucucu agcaguuacu auggaugacu uccggguaag    12840
gaccacaccc gugccucagg uacacacaua cgugcuuuga ccccuccccuu gauaagcucuc    12900 auccccaguu uucccuccuu uucuagggg ccuugagcca gaguaaaccca ucagcacugc    12960 gggaaaccgu gguagaggug ccacagguaa ccugggaaga caucggggc cuagaggaug    13020 ucaaacguga gcuacaggag cugguccagg uagggcaacu gguccagggg ugagucacug    13080
ucucaguaca uguaauuga ucggguggau ucaggggugu caacacauuu gcugcaagag    13140
uugugagagc acgacuuagg aaccacugu ucuuagguuu gaggcacuaa ggagucuucu    13200
ucuagagaac cuggaucuga uaccauggg uacaccauga aauaauggag gggaugcuuc    13260
uguuuaguua gguucuuuc aaaaugugga ggguagccuug aacccucuuu ccuuuuccuc    13320
cuaguauccu guggagcacc cagacaaauu ccugaaguuu ggcaugacac cuuccaaggg    13380
aguucuguuc uauggaccuc cuggcugugg gaaaacuuug uuggccaaag ccauugcuaa    13440
ugaaugccag gccaacuuca ucuccaucaa gggucccugag cugcucacca ugugguuggg    13500
ggagucugag gccaaugguc agaaaaucuu ugacaagguug agcuacaaua ggcugaacua    13560
uguauugauu ugccgaggg caaggaauag aggcuguuuu ucuuuaagag gguugaaaua    13620
uucuuagugc uggcugcuca acugcacagu aaagucacuug auuucuuuc ugaggucuga    13680
```

```
gagaccuagu guuauuuuuu uuuucucucu cucucucuug agacaggguc uggcucuguu    13740
gcccagguug gagggcagug guacagucau ggcucacugu aaccuugaaa ccugggcuua    13800
agcaauucuc cuacuucagc cuccugagua gcugggacua uaggcaugcg ucaccacauc    13860
uggcuaauuu uuuauuuuuu guagagacaa agucucagua uguugcccau gcugguuucg    13920
gauuucuggc cucaagugau ccucccaccu uggccuccca aagugcuggg aauacaggug    13980
ugagccacca cguuugccua gagacaucua guuuguuuag ugcuugaauc aaccauucc     14040 uccuacaggc ccgccaagcu gcccccugug ugcuauucuu gaugagcug gauucgauug     14100 ccaaggcucg uggagguaac auuggagaug gugguggggc ugcugaccga gucaucaacc    14160
agauccugac agaaauggau ggcaugucca caaaaaaaaa uguguucauc auuggcgcua    14220
ccaaccggcc ugacaucauu gauccugcca uccucagacc uggccgucuu gaucagcuca    14280
ucuacauccc acuccugau gagaagucccc guguugccau ccucaaggcu aaccugcgca    14340
aguccccagu ugccaaggca ggugcaagau caugggcugu gggagacuug caugaguccu    14400 caggcugguua cggagugcuc uuuaguuucu ggacaagauu ccacugggu uaggguuggu    14460 cuaaagggaa gguagaauuu uugaggauau caagauaauc uagaaucagg aauaaaaugg    14520
gguggccaaa aagggcaa acuguaguug ggagugcucg gguagcccaa agaucugcgu      14580
aucucgagag gagaggcuaa augcuaaggu accucugcug cugcuuuuag gauguggacu    14640
uggaguuccu ggcuaaaaug acuaauggcu ucucuggagc ugaccugaca gagauuugcc    14700
agcgugcuug caagcuggcc auccgugaau ccaucgagag ugagauuagg cgagaacgag    14760
agaggcagac aaacccauca gccauggua gucugcaucc uuuccccaga ugugccaauc    14820
auggagagcc aggcagcagc caccaccaug cccuggaguu gagaguagaa gcuguggaa    14880 agaucaucua acugaagaga uuuuaauag ggcaucaaag auaaagaaug cugaggugaa     14940
uccauucaau uuggaauaag gccgagaaga gauggucagg cuccauucuc agucugaacc    15000
aagcuccaug agggaaauca aaguaugaga gugcagcaaa cacagcaagg uuuuuuuugu    15060
uuuuuguuuu uuguuuuuuu uuugagacga agucucacuc uguugccag acuggagugc    15120 aguggcacga ucuuggcuca cugcaacuuc ugccucccag guucaagcga uucuccugcc    15180
ucagccuccc gaguagcugg gacuacaggc acaugccacc auguccggcu aguuuuugu     15240 auuuuuuuuu uagaagaaac gugguuucac cacguuagcc aggauggucu cgaucuccug    15300
accuugugau gugcccaccu cggccucca aagugcuggg auuacaggcg ugaaccacag     15360
agcaagguuu ugagcugaga ugagacacau auacuuaucc cugauggug gggaagggau     15420 agggucccaca gaccucccaa aaugaaaagg caaauucaug uguuuguaag uuccauaaag   15480
guaagaucuc ugucaucuca cuuguuuucc acuaugucuu guguacccu uaauuaauuc     15540 auuaaguucc aaacauggga cuuaaugagc aaauaaaugg cuucuuucc cuuuugaagg     15600 gucugugaca ucccuucucu cucccauaaa agcuuaacaa cuacgauga acuaauccua     15660 ggagguaguc acauaaguca cagaaauugg ccucucaaug gaagagauag guuuugagcu    15720
gggcugugaa gagaguagaa uuugaauaaa gggaauaagc agcccaaaua augugcucua    15780 guauaggau ugcaaucauu gggaaacccu gguagauuu aagaguauau augucacugg      15840
aagugagacc gcuagguagg auguaauccaa aaugugguaa gcacugaaag ccauuggcau   15900 uccuuuuaa aguauuaagg uuuauuaagg uaugauauaa auacaauaaa auucacucuu     15960
ucuauauacc auuccaugc uuuaugacaa gugugugugua guucuauaac uacuaccaca    16020
guugagacuu aaaauuucua cuaucucaaa aaguuuccuu agccacuuca gucaacaucu    16080
```

```
ccccuccuua agccccauca cugaugugau uucugucccu acaguuuucc cuuuuccaga    16140
gugcauugac aaguuuuaa gcagagcagu gacucaauuu uaggaagcau ggccuagcau    16200
cuuaccucag guuggauugg aagggcaagg agaccaauaa acugcaguaa ugggaggccu    16260
gggaugaaau ccaggcuggg cuuuaacuag cccuagugau cuguguuuac caacauaugg    16320
agguagaaga ggaugaucca gugccugaga ccgucgaga ucacuugaa gaagccaugc    16380 gcuugcgcg ccguucuguc agugacaaug acauucggaa gaugagaug uuugcccaga    16440 cccuucagca gagucgggc uuuggcagcu ucagguaagu gguugggag cauuagacag    16500 ugcuuaaguu acuuuggga ccuacaccaa aagggauggg aguccuaagg aagcuagagg    16560
gguaguugug gaaaucuuac acaggcccug uccuaacccu cuuuuuggc uuugcucuug    16620 uacacagauu cccuucaggg aaccagggug gagcuggccc cagucagggc aguggaggcg    16680
gcacaggugg caguguauac acagaagaca augaugauga ccuguauggc uaagugugg    16740 uggccagcgu gcagugagcu ggccugccug gaccuuguuc ccgggggug ggggcgcuug    16800 cccaggagag ggaccagggg ugcgcccaca gccugcucca uucuccaguc ugaacaguuc    16860
agcuacaguc ugacucugga cagggggguuu cuguugcaaa aauacaaaac aaaagcgaua    16920
aaauaaaagc gauuucauu ugguaggcgg agagugaauu accaacaggg aauugggccu    16980
ugggccauag ccauuucugu guaguuugg ggcagcagg gggaccugug uggggugugua    17040 accaaggcac uacugccacc ugccacagua aagcaucugc acuugacuca augcugcccg    17100 agccccccu uccccuauc caaccugggu aggugguag gggccacagu ugcuggaugu    17160
uuauauagag aguagguuga uuuauuuuac augcuuuuga guuaauguug gaaaacuaau    17220
cacaagcagu uucuaaacca aaaaaugaca uguguaaaa ggacaauaaa cguuggguca    17280
aaauggagcc ugauccuugg gcccugugcc ugcuucuuuu ccugggaaca gccuuggggcu    17340 acccaccacu cccaaggcau ucuuccaaau gugaaauccu ggaaguaaga uugcaccuuc    17400
uuccucuccu gaucaacauc gguaugaugu cuccuguugc cucacccuuu gucugcagua    17460
ucacuggaua ggacuggugg aaagggagca gccugacaga gcccaaaug uggagaauau    17520 ggcaucccuc caccuauauu ugauguggac gguaaggcua ggccugcagg aucccuuauc    17580
cugaccaaag acuguguugg ggugccauuu gaaaaucgca ggguugcaaa agaauacaau    17640
cuuacuugca ggggauauu cucuauacuc ucuuuuaaug caucuaaaaa ucccaaaacau    17700 ccccugguug gugaucacuu acaguugugu ccaccuuuau uuuauguacu uugauuaaaa    17760 aaaaaaacu uuuguuaau auaaaauuuu aguauugaau uuuuuuuu uccaaacaga    17820 aaauagacua uccucuucaa caguaaucac uuagugcuuc uagggucagu acagugaugc    17880
cuuacccaga gagagauag ugcagagaaa auaaauuacu aaauuaaaua auguugauu    17940 ggcuuuggga cauaaucuca aaagacaguc cugaacaccg uaauuugaa uaaaauacug    18000 uaaucuccaa agaucaaaau cccuaaaguc uaaaauucug aaaaucacaa ucccaaaagg    18060 ucaaaaucc aaaauacaau ucuggaagaa auacuaaaca uucuucgaaa auuuacuuac    18120
auuuuuaaaa gcguauuuau uugagaaaca acacaacaga acguuucaua ggccacuaca    18180
cgauaaaaua gggaauagua acauuuuugc aagauaaaca cucagguaua ccaaugacag    18240
uugcacggau auaacgguga ugagcagaug aaacauucau aaagaaauag gucaaaaagu    18300 gaaaugauaua aaugcuuugu cacuaugcuu gguaauugug ggcaccuagc uuuauauaac    18360
uggucaucug uaauacugug acagaa                                         18386
```

<210> SEQ ID NO 9
<211> LENGTH: 806
<212> TYPE: PRT
<213> ORGANISM: Homo sapiens

<400> SEQUENCE: 9

Met Ala Ser Gly Ala Asp Ser Lys Gly Asp Asp Leu Ser Thr Ala Ile
1               5                   10                  15

Leu Lys Gln Lys Asn Arg Pro Asn Arg Leu Ile Val Asp Glu Ala Ile
            20                  25                  30

Asn Glu Asp Asn Ser Val Val Ser Leu Ser Gln Pro Lys Met Asp Glu
        35                  40                  45

Leu Gln Leu Phe Arg Gly Asp Thr Val Leu Leu Lys Gly Lys Lys Arg
    50                  55                  60

Arg Glu Ala Val Cys Ile Val Leu Ser Asp Asp Thr Cys Ser Asp Glu
65                  70                  75                  80

Lys Ile Arg Met Asn Arg Val Val Arg Asn Asn Leu Arg Val Arg Leu
                85                  90                  95

Gly Asp Val Ile Ser Ile Gln Pro Cys Pro Asp Val Lys Tyr Gly Lys
            100                 105                 110

Arg Ile His Val Leu Pro Ile Asp Asp Thr Val Glu Gly Ile Thr Gly
        115                 120                 125

Asn Leu Phe Glu Val Tyr Leu Lys Pro Tyr Phe Leu Glu Ala Tyr Arg
    130                 135                 140

Pro Ile Arg Lys Gly Asp Ile Phe Leu Val Arg Gly Gly Met Arg Ala
145                 150                 155                 160

Val Glu Phe Lys Val Val Glu Thr Asp Pro Ser Pro Tyr Cys Ile Val
                165                 170                 175

Ala Pro Asp Thr Val Ile His Cys Glu Gly Glu Pro Ile Lys Arg Glu
            180                 185                 190

Asp Glu Glu Glu Ser Leu Asn Glu Val Gly Tyr Asp Asp Ile Gly Gly
        195                 200                 205

Cys Arg Lys Gln Leu Ala Gln Ile Lys Glu Met Val Glu Leu Pro Leu
    210                 215                 220

Arg His Pro Ala Leu Phe Lys Ala Ile Gly Val Lys Pro Pro Arg Gly
225                 230                 235                 240

Ile Leu Leu Tyr Gly Pro Pro Gly Thr Gly Lys Thr Leu Ile Ala Arg
                245                 250                 255

Ala Val Ala Asn Glu Thr Gly Ala Phe Phe Phe Leu Ile Asn Gly Pro
            260                 265                 270

Glu Ile Met Ser Lys Leu Ala Gly Glu Ser Glu Ser Asn Leu Arg Lys
        275                 280                 285

Ala Phe Glu Glu Ala Glu Lys Asn Ala Pro Ala Ile Ile Phe Ile Asp
    290                 295                 300

Glu Leu Asp Ala Ile Ala Pro Lys Arg Glu Lys Thr His Gly Glu Val
305                 310                 315                 320

Glu Arg Arg Ile Val Ser Gln Leu Leu Thr Leu Met Asp Gly Leu Lys
                325                 330                 335

Gln Arg Ala His Val Ile Val Met Ala Ala Thr Asn Arg Pro Asn Ser
            340                 345                 350

Ile Asp Pro Ala Leu Arg Arg Phe Gly Arg Phe Asp Arg Glu Val Asp
        355                 360                 365

Ile Gly Ile Pro Asp Ala Thr Gly Arg Leu Glu Ile Leu Gln Ile His
    370                 375                 380

-continued

Thr Lys Asn Met Lys Leu Ala Asp Asp Val Asp Leu Glu Gln Val Ala
385                 390                 395                 400

Asn Glu Thr His Gly His Val Gly Ala Asp Leu Ala Ala Leu Cys Ser
            405                 410                 415

Glu Ala Ala Leu Gln Ala Ile Arg Lys Lys Met Asp Leu Ile Asp Leu
        420                 425                 430

Glu Asp Glu Thr Ile Asp Ala Glu Val Met Asn Ser Leu Ala Val Thr
    435                 440                 445

Met Asp Asp Phe Arg Trp Ala Leu Ser Gln Ser Asn Pro Ser Ala Leu
450                 455                 460

Arg Glu Thr Val Val Glu Val Pro Gln Val Thr Trp Glu Asp Ile Gly
465                 470                 475                 480

Gly Leu Glu Asp Val Lys Arg Glu Leu Gln Glu Leu Val Gln Tyr Pro
                485                 490                 495

Val Glu His Pro Asp Lys Phe Leu Lys Phe Gly Met Thr Pro Ser Lys
            500                 505                 510

Gly Val Leu Phe Tyr Gly Pro Pro Gly Cys Gly Lys Thr Leu Leu Ala
        515                 520                 525

Lys Ala Ile Ala Asn Glu Cys Gln Ala Asn Phe Ile Ser Ile Lys Gly
530                 535                 540

Pro Glu Leu Leu Thr Met Trp Phe Gly Glu Ser Glu Ala Asn Val Arg
545                 550                 555                 560

Glu Ile Phe Asp Lys Ala Arg Gln Ala Ala Pro Cys Val Leu Phe Phe
                565                 570                 575

Asp Glu Leu Asp Ser Ile Ala Lys Ala Arg Gly Gly Asn Ile Gly Asp
            580                 585                 590

Gly Gly Gly Ala Ala Asp Arg Val Ile Asn Gln Ile Leu Thr Glu Met
        595                 600                 605

Asp Gly Met Ser Thr Lys Lys Asn Val Phe Ile Ile Gly Ala Thr Asn
    610                 615                 620

Arg Pro Asp Ile Ile Asp Pro Ala Ile Leu Arg Pro Gly Arg Leu Asp
625                 630                 635                 640

Gln Leu Ile Tyr Ile Pro Leu Pro Asp Glu Lys Ser Arg Val Ala Ile
                645                 650                 655

Leu Lys Ala Asn Leu Arg Lys Ser Pro Val Ala Lys Asp Val Asp Leu
            660                 665                 670

Glu Phe Leu Ala Lys Met Thr Asn Gly Phe Ser Gly Ala Asp Leu Thr
        675                 680                 685

Glu Ile Cys Gln Arg Ala Cys Lys Leu Ala Ile Arg Glu Ser Ile Glu
    690                 695                 700

Ser Glu Ile Arg Arg Glu Arg Glu Arg Gln Thr Asn Pro Ser Ala Met
705                 710                 715                 720

Glu Val Glu Glu Asp Asp Pro Val Pro Glu Ile Arg Arg Asp His Phe
                725                 730                 735

Glu Glu Ala Met Arg Phe Ala Arg Arg Ser Val Ser Asp Asn Asp Ile
            740                 745                 750

Arg Lys Tyr Glu Met Phe Ala Gln Thr Leu Gln Gln Ser Arg Gly Phe
        755                 760                 765

Gly Ser Phe Arg Phe Pro Ser Gly Asn Gln Gly Ala Gly Pro Ser
    770                 775                 780

Gln Gly Ser Gly Gly Gly Thr Gly Gly Ser Val Tyr Thr Glu Asp Asn
785                 790                 795                 800

Asp Asp Asp Leu Tyr Gly
            805

<210> SEQ ID NO 10
<211> LENGTH: 1567
<212> TYPE: DNA
<213> ORGANISM: Homo sapiens

<400> SEQUENCE: 10

| | | | | | |
|---|---|---|---|---|---|
| catccagcca | tgccctgatg | tgaagtacgg | caaacgtatc | catgtgctgc | ccattgatga | 60 |
| cacagtggaa | ggcattactg | gtaatctctt | cgaggtatac | cttaagccgt | acttcctgga | 120 |
| agcgtatcga | cccatccgga | aaggtgagag | ctaattctga | gcttaaggat | tattgactgt | 180 |
| agggaataaa | ccttggaaca | tctttatctc | attttctttt | tctttttttt | ttttaaatc | 240 |
| ttttatgctt | ttcccctgta | tttatttatt | catttttttaa | gagatggggt | cagctgggca | 300 |
| ccgtggctca | cacctataat | cccagcaatt | tgggaggctg | aggcgggtgg | atcacttgag | 360 |
| gccaggagtt | tgagaccagc | ctggccaaca | tggcgaaacc | ccatcgtggg | cacctgtaat | 420 |
| cccagctacc | tgggaggctg | aggcatgaga | attgcttgaa | cccaagaggt | ggaggttgca | 480 |
| gtgagccaag | attgggccac | agtactgcag | cctgggtgac | agagcaagac | tctgtctcaa | 540 |
| aaaaaaaaa | aaagagacag | ggtctcacta | tgatgcccag | gctggtctca | aactgctggg | 600 |
| ctcaagtgat | ccatctgcca | tggcctccca | aagtgctggg | attacaggca | tgagccatca | 660 |
| agcctagtct | cattttcttt | tctttttttt | ttgagacaga | gtgtcgcgct | gtccccagg | 720 |
| ctggagcgca | gtggtgcaat | ctcggctcac | tgcaacctcc | gcctcctggg | ttcaagcaat | 780 |
| tctcctgcct | cagcctccca | agtagctggg | attacaggcg | tctgccacca | cgcccggcta | 840 |
| attttttgtgt | ttttagtaga | dacggggttt | caccatgttg | gtcaggctcg | tctcgaactc | 900 |
| ttgacctcag | gtgagccact | gtgcccggcc | gctagactca | ttttcatata | tttgtataca | 960 |
| cacacatgca | aaccctgcac | acatattcat | atgtcttacc | ctctttttttt | cctccatcct | 1020 |
| tcctttgctc | catctctccc | cttctctgtt | ccaggagagt | aagctatctt | tatggatctc | 1080 |
| tgaaggagaa | agtggtccat | tttggctggg | tcagggtcca | gagtgcacag | ttctaccatt | 1140 |
| ggtggttgta | gtgaaaactt | gggctaccta | tatggcagaa | gtcagaactt | gatgggcttc | 1200 |
| tgacatgtca | ggttttgttc | actgacctct | tgtcagaggg | actcttcaca | gtttaccttt | 1260 |
| ctcatcttgc | ctgctgctta | ttaagacagg | tggggtggag | ttggggagag | gtagggcaat | 1320 |
| atctaatgaa | gggcactatc | taatgagctt | ggcattttga | ccccagggtc | tgatgagttc | 1380 |
| tcactttgtc | ttgtagttga | cacctctaac | tgtgcttgta | ctgtttgctc | tcgcaggaga | 1440 |
| catttttctt | gtccgtggtg | ggatgcgtgc | tgtggagttc | aaagtggtgg | aaacagatcc | 1500 |
| tagcccttat | tgcattgttg | ctccagacac | agtgatccac | tgcgaagggg | agcctatcaa | 1560 |
| acgagag | | | | | 1567 |

What is claimed is:

1. A method of treating valosin-containing protein (VCP)-associated inclusion body myopathy (IBM) in a subject in need thereof, the method comprising administering to said subject a therapeutically effective amount of an antisense VCP exon 4 nucleic acid or an antisense VCP exon 5 nucleic acid.

2. The method of claim 1, wherein said antisense VCP exon 4 nucleic acid or said antisense VCP exon 5 nucleic acid effects exon skipping of VCP exon 4 or VCP exon 5 in said subject, respectively.

3. The method of claim 1, wherein said antisense VCP exon 4 nucleic acid or an antisense VCP exon 5 nucleic acid binds to an acceptor or donor splice site of VCP exon 4 or an acceptor or donor splice site of VCP exon 5 in said subject, respectively.

4. The method of claim 1, wherein said antisense VCP exon 4 nucleic acid or said antisense VCP exon 5 nucleic acid binds to an intronic sequence flanking VCP exon 4 or an intronic sequence flanking VCP exon 5, respectively.

5. The method of claim 1, wherein said antisense VCP exon 4 nucleic acid or said antisense VCP exon 5 nucleic acid binds to a VCP exon 4 splice enhancer sequence or a VCP exon 5 splice enhancer sequence, respectively.

6. The method of claim 1 comprising administering an antisense VCP exon 5 nucleic acid.

7. The method of claim 1, wherein said antisense VCP exon 5 nucleic acid binds to a VCP Exon 5A sequence.

8. The method of claim 7, wherein said antisense VCP exon 5 nucleic acid comprises a sequence of SEQ ID NO:1, SEQ ID NO:2, SEQ ID NO:3, SEQ ID NO:4, SEQ ID NO:5 or SEQ ID NO:6.

9. The method of claim 1, wherein said subject has an R155H mutation in VCP exon 5.

10. The method of claim 9, wherein said antisense VCP exon 5 nucleic acid binds to a VCP exon 5 sequence comprising the R155H mutation.

11. The method of claim 1, wherein said antisense VCP exon 4 nucleic acid and said antisense VCP exon 5 nucleic acid are modified nucleic acids.

12. The method of claim 11, wherein said modified nucleic acids are phosphorodiamidate morpholino oligomers (PMO), peptide nucleic acids (PNA), locked nucleic acids (LNA), ethylene bridged nucleic acids (ENA) or 2'-O-methyl modified nucleic acids.

13. The method of claim 11, wherein said modified nucleic acids are phosphorodiamidate morpholino oligomers (PMO).

14. The method of claim 13, wherein said modified nucleic acids comprise a phosphodiester backbone, phosphorothioate backbone, phosphorodithioate backbone or boranophosphate backbone.

15. The method of claim 14, wherein said modified nucleic acids are 2'-O-methyl modified nucleic acids comprising a phosphorothioate backbone.

16. The method of claim 1, wherein said antisense VCP exon 4 nucleic acid and said antisense VCP exon 5 nucleic acid are administered systemically as cationic lipoplexes.

17. The method of claim 1, wherein said VCP-associated IBM is IBM associated with Paget's disease of the bone and Frontotemporal Dementia (IBMPFD).

* * * * *